United States Patent
Fairman et al.

(10) Patent No.: US 9,089,537 B2
(45) Date of Patent: Jul. 28, 2015

(54) SUBUNIT VACCINES FOR HERPES VIRUSES AND METHODS OF USE

(75) Inventors: Jeffery Fairman, Mountain View, CA (US); Gary H. Cohen, Havertown, PA (US); Roselyn J. Eisenberg, Haddonfield, NJ (US)

(73) Assignees: The Trustees of the University of Pennsylvania, Philadelphia, PA (US); Juvaris Biotherapeutics, Inc., Burlingame, CA (US)

( * ) Notice: Subject to any disclaimer, the term of this patent is extended or adjusted under 35 U.S.C. 154(b) by 0 days.

(21) Appl. No.: 13/578,976

(22) PCT Filed: Feb. 25, 2011

(86) PCT No.: PCT/US2011/026188
§ 371 (c)(1),
(2), (4) Date: Mar. 25, 2013

(87) PCT Pub. No.: WO2011/106607
PCT Pub. Date: Sep. 1, 2011

(65) Prior Publication Data
US 2013/0171234 A1 Jul. 4, 2013

Related U.S. Application Data

(60) Provisional application No. 61/308,856, filed on Feb. 26, 2010.

(51) Int. Cl.
*A61K 39/12* (2006.01)
*A61K 39/245* (2006.01)
*C07K 14/005* (2006.01)
*A61K 39/00* (2006.01)

(52) U.S. Cl.
CPC ............ *A61K 39/245* (2013.01); *A61K 39/12* (2013.01); *C07K 14/005* (2013.01); *A61K 2039/5252* (2013.01); *A61K 2039/53* (2013.01); *A61K 2039/55505* (2013.01); *A61K 2039/55555* (2013.01); *A61K 2039/55572* (2013.01); *A61K 2039/70* (2013.01); *C12N 2710/16622* (2013.01); *C12N 2710/16634* (2013.01)

(58) Field of Classification Search
CPC ............ A61K 2300/00; A61K 39/12; A61K 2039/55555; A61K 35/763; A61K 38/162; A61K 2039/525; A61K 2039/6075; A61K 9/127; C07K 14/005; C07K 16/081; C12N 2710/00011; C12N 2710/16011
See application file for complete search history.

(56) References Cited

U.S. PATENT DOCUMENTS

| | | | |
|---|---|---|---|
| 6,156,319 | A | 12/2000 | Cohen et al. |
| 6,693,086 | B1 | 2/2004 | Dow et al. |
| 2009/0263423 | A1* | 10/2009 | Fairman et al. ............ 424/209.1 |
| 2012/0121630 | A1* | 5/2012 | Bryan et al. ............... 424/186.1 |

OTHER PUBLICATIONS

Solodin I, Brown CS, Bruno MS, Chow CY, Jang EH, Debs RJ, Heath TD. A novel series of amphiphilic imidazolinium compounds for in vitro and in vivo gene delivery. Biochemistry. Oct. 17, 1995;34(41):13537-44.*
Atanasiu D, Whitbeck JC, de Leon MP, Lou H, Hannah BP, Cohen GH, Eisenberg RJ. Bimolecular complementation defines functional regions of Herpes simplex virus gB that are involved with gH/gL as a necessary step leading to cell fusion. J Virol. Apr. 2010;84(8):3825-34. doi: 10.1128/JVI.02687-09. Epub Feb. 3, 2010.*
Benmohamed et al., "Identification of novel immunodominant CD4+ Th1-type T cell peptide epitopes from herpes simplex glycoprotein D that confer protective immunity." 2003, J. Virol. 77: 9463-73.
Bettahi et al. "Protective immunity to genital herpes simplex virus type 1 and type 2 provided by self-adjuvanting lipopeptides that drive dendritic cell maturation and elicit a polarized Th1 immune response." 2006 Viral Immunol. 19(2):220-36.
Chang et al., "A novel vaccine adjuvant for recombinant flu antigens." 2009, Biologicals. 37(3): 141-147.
Fairman et al., "Enhanced in vivo immunogenicity of SIV vaccine candidates with cationic liposome-DNA complexes in a rhesus macaque pilot study." 2009, Hum. Vaccin. 5(3):141-50.
Krummenacher et al., "Structure of unliganded HSV gD reveals a mechanism for receptor-mediated activation of virus entry." 2005 EMBO Journal, 24:4144-4153.
Liu et al., "Factors influencing the efficiency of cationic liposome-mediated intravenous gene delivery." 1997, Nature Biotech., 15:167-173.
Peng, et al., "Thje gH-GL complex of herpes simplex virus (HSV) stimulates neutralizing antibody and protects mice against HSV type 1 challenge." 1998 J Virol 72(1):65-72.
Solodin et al., "A novel series of amphiphilic imidazolinium compounds for in vitro and in vivo gene delivery." 1995, Biochemistry, 34:13537-13544.
Stanberry et al., "Glycoprotein-D-adjuvant vaccine to prevent genital herpes." 2002, N Engl J Med. 347(21):1652-61.
Templeton et al., "Improved DNA: liposome complexes for increased systemic delivery and gene expression." 1997, Nature Biotech., 15:647-652.
Goncalves, et al., Biophys. J., vol. 86, pp. 1554-1563 (2004).
Nchinda, et al., BMC Biotech., vol. 2, pp. 2-12 (2002).
Felgner, et al., PNAS, vol. 84, pp. 7413-7417 (1987).
Han, et al., Nucl. Acids Res., vol. 24, pp. 4362-4363 (1996).
DOTAP, Avanti Polar Lipids product page, obtained Jan. 8, 2015.
DOTMA, Avanti Polar Lipids product page, obtained Jan. 8, 2015.
DDAB, Avanti Polar Lipids product page, obtained Jan. 8, 2015.

* cited by examiner

*Primary Examiner* — Benjamin P Blumel
*Assistant Examiner* — Rachel Gill
(74) *Attorney, Agent, or Firm* — Saul Ewing, LLP; Kathryn Doyle

(57) ABSTRACT

The present disclosure generally relates to vaccine compositions for Herpes Simplex Viruses (HSV) types 1 and/or 2. The vaccines comprise isolated antigens or glycoprotein subunits of the viruses, optionally with an adjuvant, such as a cationic liposome DNA complex (CLDC). Also the present disclosure contains methods of vaccinating a subject utilizing these compositions.

17 Claims, 33 Drawing Sheets

HSV-2 glycoprotein D (gD2; GI:156072227)

```
-25 mgrltsgvgt aallvvavgl rvvcakyala dpslkmadpn rfrgknlpvl drltdppgvk
 36 rvyhiqpsle dpfqppsipi tvyyavlera crsvllhaps eapqivrgas dearkhtynl
 96 tiawyrmgdn caipitvmey tecpynkslg vcpirtqprw syydsfsavs ednlgflmha
156 pafetagtyl rlvkindwte itqfilehra rasckyalpl rippaaclts kayqqgvtvd
216 sigmlprfip enqrtvalys lkiagwhgpk ppytstllpp elsdttnatq pelvpedped
276 salledpagt vssqippnwh ipsiqdvaph hapaapsnpg liigalagst lavlviggia
336 fwvrrraqma pkrlrlphir dddappshqp lfy
```

HSV-2 glycoprotein D nucleic acid (gD2; GI:156072226)

```
   1 atggggcgtt tgacctccgg cgtcgggacg gcggccctgc tagttgtcgc ggtgggactc
  61 cgcgtcgtct gcgccaaata cgccttagca gacccctcgc ttaagatggc cgatcccaat
 121 cgatttcgcg ggaagaacct tccggttttg gaccggctga ccgacccccc cggggtgaag
 181 cgtgtttacc acattcagcc gagcctggag gaccccgttcc agccccccag catcccgatc
 241 actgtgtact acgcagtgct ggaacgtgcc tgccgcagcg tgctcctaca tgccccatcg
 301 gaggcccccc agatcgtgcg cggggcttcg gacgaggccc gaaagcacac gtacaacctg
 361 accatcgcct ggtatcgcat gggagacaat tgcgctatcc ccatcacggt tatggaatac
 421 accgagtgcc cctacaacaa gtcgttgggg gtctgcccca tccgaacgca gccccgctgg
 481 agctactatg acagctttag cgccgtcagc gaggataacc tgggattcct gatgcacgcc
 541 cccgccttcg agaccgcggg tacgtacctg cggctagtga agataaacga ctggacggag
 601 atcacacaat ttatcctgga gcaccgggcc cgcgcctcct gcaagtacgc tctccccctg
 661 cgcatccccc cggcagcgtg cctcacctcg aaggcctacc aacagggcgt gacggtcgac
 721 agcatcggga tgctcccccg ctttatcccc gaaaaccagc gcaccgtcgc cctatacagc
 781 ttaaaaatcg ccgggtggca cggccccaag cccccgtaca ccagcaccct gctgccgccg
 841 gagctgtccg acaccaccaa cgccacgcaa cccgaactcg ttccggaaga ccccgaggac
 901 tcggccctct tagaggatcc cgccgggacg gtgtcttcgc agatcccccc aaactggcac
 961 atcccgtcga tccaggacgt cgcgccgcac cacgcccccg ccgcccccag caacccgggc
1021 ctgatcatcg gcgcgctggc cggcagtacc ctggcggtgc tggtcatcgg cggtattgcg
1081 ttttgggtac gccgccgcgc tcagatggcc cccaagcgcc tacgtctccc ccacatccgg
1141 gatgacgacg cgccccctc gcaccagcca ttgttttact ag
```

Figure 22

HSV-2 glycoprotein B (gB2; GI:295848592)

```
  1 mrggglvcal vvgalvaava saapaapras gdvaatvaan ggpasqpppv pspattkark
 61 rktkkppkrp eatpppdana tvaaghatlr ahlreikven adaqfyvcpp ptgatvvqfe
121 qprrcptrpe gqnytegiav vfkeniapyk fkatmyykdv tvsqvwfghr ysqfmgifed
181 rapvpfeevi dkinakgvcr stakyvrnnm ettafhrddh etdmelkpak vatrtsrgwh
241 ttdlkynpsr veafhrygtt vnciveevda rsvypydefv latgdfvyms pfygyregsh
301 tehtsyaadr fkqvdgfyar dlttkarats pttrnllttp kftvawdwvp krpavctmtk
361 wqevdemlra eyggsfrfss daisttfttn ltqyslsrvd lgdcigrdar eaidrmfark
421 ynathikvgq pqyylatggf liayqpllsn tlaelyvrey mreqdrkprn atpaplreap
481 sanasverik tssiefarl qftynhiqrh vndmlgriav awcelqnhel tlwnearkln
541 pnaiasatvg rrvsarmlgd vmavstcvpv apdnvivqns mrvssrpgtc ysrplvsfry
601 edqgpliegq lgennelrlt rdalepctvg hrryfifggg yvyfeeyays hqlsradvtt
661 vstfidlnit mledhefvpl evytrheikd sglldytevq rrnqlhdlrf adidtvirad
721 anaamfaglc affegmgdlg ravgkvvmgv vggvvsavsg vssfmsnpfg alavgllvla
781 glvaaffafr yvlqlqrnpm kalypltttke lktsdpggvg gegeegaegg gfdeaklaea
841 remirymalv samertehka rkkgtsalls skvtnmvlrk rnkarysplh nedeagdede
901 l
```

HSV-2 glycoprotein B nucleic acid (gB2; GI:295848591)

```
   1 atgcgcgggg ggggcttggt ttgcgcgctg gtcgtggggg cgctggtggc cgcggtggcg
  61 tcggcggccc cggcggcccc ccgcgcctcg ggcgacgtgg ccgcgaccgt cgcggcgaac
 121 gggggtcccg cctcccagcc gcccccgtc ccgagcccca cgaccaccaa ggcccggaag
 181 cggaaaacca aaaagccgcc caagcggccc gaggcgaccc cgcccccga cgccaacgcg
 241 accgtcgccg ccggccacgc cacgctgcgc cgcacctgc gggaaatcaa ggtcgagaac
 301 gccgatgccc agttttacgt gtgcccgccc ccgacgggcg ccacggtggt gcagtttgag
 361 cagccgcgcc gctgccgac gcgcccggag gggcagaact acacggaggg catcgcggtg
 421 gtcttcaagg agaacatcgc cccgtacaaa ttcaaggcca ccatgtacta caaagacgtg
 481 accgtgtcgc aggtgtggtt cggccaccgc tactcccagt ttatggggat attcgaggac
 541 cgcgcccccg ttccttcga ggaggtgatc gacaagatta acgccaaggg ggtctgccgc
 601 tccacggcca agtacgtgcg gaacaacatg gagaccaccg cgtttcaccg ggacgaccac
 661 gagaccgaca tggagctcaa gccggcgaag gtcgccacgc gcacgagccg ggggtggcac
 721 accaccgacc tcaagtacaa ccctcgcgg gtggaggcgt tccatcggta cggcacgacg
 781 gtcaactgca tcgtcgagga ggtggacgcg cggtcggtgt accgtacga tgagtttgtg
 841 ctggcgacgg gcgactttgt gtacatgtcc ccgttttacg gctaccggga ggggtcgcac
 901 accgagcaca ccagctacgc cgccgaccgc ttcaagcagg tcgacggctt ctacgcgcgc
 961 gacctcacca cgaaggcccg ggccacgtcg ccgacgaccc gcaacttgct gacgacccc
1021 aagttttaccg tggcctggga ctgggtgccg aagcgaccgg cggtctgcac catgaccaag
1081 tggcaggagg tggacgagat gctccgcgcc gagtacggcg gctccttccg cttctcctcc
1141 gacgccatct cgaccacctt caccaccaac ctgacccagt actcgctctc gcgcgtcgac
1201 ctggcgact gcatcggccg ggatgcccgc gaggccatcg accgcatgtt tgcgcgcaag
1261 tacaacgcca cgcacatcaa ggtgggccag ccgcagtact acctggccac ggggggcttc
1321 ctcatcgcgt accagcccct cctcagcaac acgctcgccg agctgtacgt gcgggagtac
1381 atgcgggagc aggaccgcaa gccccggaat gccacgcccg cgccactgcg ggaggcgccc
1441 agcgccaacg cgtccgtgga gcgcatcaag accacctcct cgatcgagtt cgcccggctg
```

Figure 23

```
1501 cagtttacgt ataaccacat acagcgccac gtgaacgaca tgctggggcg catcgccgtc
1561 gcgtggtgcg agctgcagaa ccacgagctg actctctgga acgaggcccg caagctcaac
1621 cccaacgcca tcgcctccgc caccgtcggc cggcgggtga gcgcgcgcat gctcggagac
1681 gtcatggccg tctccacgtg cgtgcccgtc gccccggaca acgtgatcgt gcagaactcg
1741 atgcgcgtca gctcgcggcc ggggacgtgc tacagccgcc cctggtcag ctttcggtac
1801 gaagaccagg gcccgctgat cgaggggcag ctgggcgaga caacgagct gcgcctcacc
1861 cgcgacgcgc tcgagccgtg caccgtgggc caccggcgct acttcatctt cggcggggc
1921 tacgtgtact tcgaggagta cgcgtactct caccagctga gtcgcgccga cgtcaccacc
1981 gtcagcacct tcatcgacct gaacatcacc atgctggagg accacgagtt tgtgcccctg
2041 gaggtctaca cgcgccacga gatcaaggac agcggcctgc tggactacac ggaggtccag
2101 cgccgcaacc agctgcacga cctgcgcttt gccgacatcg acacggtcat ccgcgccgac
2161 gccaacgccg ccatgttcgc ggggctgtgc gcgttcttcg aggggatggg ggacttgggg
2221 cgcgcggtcg gcaaggtcgt catgggagta gtgggggggcg tggtgtcggc cgtctcgggc
2281 gtgtcctcct ttatgtccaa cccttcggg gcgcttgccg tggggctgct ggtcctggcc
2341 ggcctggtcg cggccttctt cgccttccgc tacgtcctgc aactgcaacg caatcccatg
2401 aaggccctgt atccgctcac caccaaggaa ctcaagactt ccgaccccgg gggcgtgggc
2461 ggggagggg aggaaggcgc ggaggggggc gggtttgacg aggccaagtt ggccgaggcc
2521 cgagaaatga tccgatatat ggctttggtg tcggccatgg agcgcacgga acacaaggcc
2581 agaaagaagg gcacgagcgc cctgctcagc tccaaggtca ccaacatggt tctgcgcaag
2641 cgcaacaaag ccaggtactc tccgctccac aacgaggacg aggccggaga cgaagacgag
2701 ctctaa
```

Figure 23 cont'd.

HSV-2 glycoprotein H (gH2; GI:82013506)

```
  1 mgpglwvvmg vlvgvagghd tywteqidpw flhglglart ywrdtntgrl wlpntpdasd
 61 pqrgrlappg elnlttasvp mlrwyaerfc fvlvttaefp rdpgqllyip ktyllgrprn
121 aslpelpeag ptsrppaevt qlkglshnpg asallrsraw vtfaaapdre gltfprgddg
181 aterhpdgrr napppgppag tprhpttnls iahlhnasvt wlaargllrt pgryvylsps
241 astwpvgvwt tgglafgcda alvrarygkg fmglvismrd sppaeiivvp adktlarvgn
301 ptdenapavl pgppagpryr vfvlgaptpa dngsaldalr rvagypeest nyaqymsray
361 aeflgedpgs gtdarpslfw rlagllassg fafvnaahah dairlsdllg flahsrvlag
421 laargaagca adsvflnvsv ldpaarlrle arlghlvaai lereqslvah algyqlafvl
481 dspaaygava psaarlidal yaeflggral tapmvrralf yatavlrapf lagapsaeqr
541 erarrgllit talctsdvaa athadlraal artdhqknlf wlpdhfspca aslrfdlaeg
601 gfildalama trsdipadvm aqqtrgvasv ltrwahynal irafvpeath qcsgpshnae
661 prilvpithn asyvvthtpl prgigykltg vdvrrplfit yltatcegha reiepkrlvr
721 tenrrdlglv gavflrytpa gevmsvllvd tdatqqqlaq gpvagtpnvf ssdvpsvall
781 lfpngtvihl lafdtlpiat iapgflaasa lgvvmitaal agilrvvrtc vpflwrre
```

```
ATGGGCCCCGGTCTGTGGGTGGTGATGGGGGTCCTGGTGGGCGTTGCCGGGGGCCATGACACGTACTGGAC
GGAGCAAATCGACCCGTGGTTTTTGCACGGTCTGGGGTTGGCCCGCACGTACTGGCGCGACACAAACACCG
GGCGTCTGTGGTTGCCCAACACCCCCGACGCCAGCGACCCCCAGCGCGGACGCTTGGCGCCCCGGGCGAA
CTCAACCTGACTACGGCATCCGTGCCCATGCTTCGGTGGTACGCCGAGCGCTTTTGTTTCGTGTTGGTCAC
CACGGCCGAGTTTCCTCGGGACCCCGGGCAGCTGCTTTACATCCCAAAGACCTATCTGCTCGGCCGGCCTC
GGAACGCGAGCCTGCCCGAGCTCCCCGAGGCGGGGCCCACGTCCCGTCCCCCCGCCGAGGTGACCCAGCTC
AAGGGACTGTCGCACAACCCCGGCGCCTCCGCGCTGTTGCGGTCCCGGGCCTGGGTAACATTCGCGGCCGC
GCCGGACCGCGAGGGGCTTACGTTCCCGCGGGGAGACGACGGGGCGACCGAGAGGCACCCGGACGGCCGAC
GCAACGCGCCGCCCCGGGGCCGCCCGCGGGGACACCGAGGCATCCGACGACGAACCTGAGCATCGCGCAT
CTGCACAACGCATCCGTGACCTGGCTGGCCGCCAGGGGCCTGCTACGGACTCCGGGTCGGTACGTGTACCT
CTCCCCGTCGGCCTCGACGTGGCCCGTGGGCGTCTGGACGACGGGCGGGCTGGCGTTCGGGTGCGACGCCG
CGCTCGTGCGCGCGCGATACGGAAGGGCTTCATGGGGCTCGTGATATCGATGCGGGACAGCCCTCCGGCC
GAGATCATAGTGGTGCCTGCGGACAAGACCCTCGCTCGGGTCGGAAATCCGACCGACGAAAACGCCCCCGC
GGTGCTCCCCGGGCCTCCGGCCGGCCCCAGGTATCGCGTCTTTGTCCTGGGGGCCCCGACGCCCGCCGACA
ACGGCTCGGCGCTGGACGCCCTCCGGCGGGTGGCCGGCTACCCCGAGGAGAGCACGAACTACGCCCAGTAT
ATGTCGCGGGCCTATGCGGAGTTTTTGGGGGAGGACCCGGGCTCCGGCACGGACGCGCGTCCGTCCCTGTT
CTGGCGCCCTCGCGGGGCTGCTCGCCTCGTCGGGGTTTGCGTTCGTCAACGCGGCCCACGCCCACGACGCGA
TTCGCCTCTCCGACCTGCTGGGCTTTTTGGCCCACTCGCGCGTGCTGGCCGGCCTGGCCGCCCGGGGAGCA
GCGGGCTGCGCGGCCGACTCGGTGTTCCTGAACGTGTCCGTGTTGGACCCGGCGGCCCGCCTGCGGCTGGA
GGCGCGCCTCGGGCATCTGGTGGCCGCGATCCTCGAGCGAGAGCAGAGCCTGGTGGCGCACGCGCTGGGCT
ATCAGCTGGCGTTCGTGTTGGACAGCCCCGCGGCCTATGGCGCGGTGGCCCCGAGCGCGGCCCGCCTGATC
GACGCCCTGTACGCCGAGTTTCTCGGCGGCCGCGCGCTAACCGCCCCGATGGTCCGCCGAGCGCTGTTTTA
CGCCACGGCCGTCCTCCGGGCGCCGTTCCTGGCGGGCGCGCCCTCGGCCGAGCAGCGGGAACGCGCCCGCC
GGGGCCTCCTCATAACCACGGCCCTGTGTACGTCCGACGTCGCCGCGGCGACCCACGCCGATCTCCGGGCC
GCGCTAGCCAGGACCGACCACCAGAAAAACCTCTTCTGGCTCCCGGACCACTTTTCCCCATGCGCAGCTTC
CCTGCGCTTCGATCTCGCCGAGGGCGGGTTCATCCTGGACGCGCTGGCCATGGCCACCCGATCCGACATCC
CGGCGGACGTCATGGCACAACAGACCCGCGGCGTGGCCTCCGTTCTCACGCGCTGGGCGCACTACAACGCC
CTGATCCGCGCCTTCGTCCCGGAGGCCACCCACCAGTGTAGCGGCCCGTCGCACAACGCGGAGCCCCGGAT
CCTCGTGCCCATCACCCACAACGCCAGCTACGTCGTCACCCACACCCCCTTGCCCCGCGGGATCGGATACA
AGCTTACGGGCGTTGACGTCCGCCGCCCGCTGTTTATCACC
```

Figure 24

```
TATCTCACCGCCACCTGCGAAGGGCACGCGCGGGAGATTGAGCCGAAGCGGCTGGTGCGCACCGAAAACCG
GCGCGACCTCGGCCTCGTGGGGGCCGTGTTTCTGCGCTACACCCCGGCCGGGGAGGTCATGTCGGTGCTGC
TGGTGGACACGGATGCCACCCAACAGCAGCTGGCCCAGGGGCCGGTGGCGGGCACCCCGAACGTGTTTTCC
AGCGACGTGCCGTCCGTGGCCCTGTTGTTGTTCCCCAACGGAACTGTGATTCATCTGCTGGCCTTTGACAC
GCTGCCCATCGCCACCATCGCCCCCGGGTTTCTGGCCGCGTCCGCGCTGGGGGTCGTTATGATTACCGCGG
CCCTGGCGGGCATCCTTAGGGTGGTCCGAACGTGCGTCCCATTTTTGTGGAGACGCGAATAA
```

Figure 24 cont'd

HSV-2 glycoprotein L (gL2; Accession No. P28278; GI:136776)

```
  1 mgfvclfglv vmgawgawgg sqateyvlrs viakevgdil rvpcmrtpad dvswryeaps
 61 vidyaridgi flryhcpgld tflwdrhaqr aylvnpflfa agfledlshs vfpadtqett
121 trralykeir dalgsrkqav shapvragcv nfdysrtrrc vgrrdlrpan ttstweppvs
181 sddeassqsk platqppvla lsnapprrvs ptrgrrrhtr lrrn
```

```
ATGGGGTTCGTCTGTCTGTTTGGGCTTGTCGTTATGGGAGCCTGGGGGGCGTGGGGTGGGTCACAGGCAAC
CGAATATGTTCTTCGTAGTGTTATTGCCAAAGAGGTGGGGGACATACTAAGAGTGCCTTGCATGCGGACCC
CCGCGGACGATGTTTCTTGGCGCTACGAGGCCCCGTCCGTTATTGACTATGCCCGCATAGACGGAATATTT
CTTCGCTATCACTGCCCGGGGTTGGACACGTTTTTGTGGGATAGGCACGCCCAGAGGGCGTATCTGGTTAA
CCCCTTTCTCTTTGCGGCGGGATTTTTGGAGGACTTGAGTCACTCTGTGTTTCCGGCCGACACCCAGGAAA
CAACGACGCGCCGGGCCCTTTATAAAGAGATACGCGATGCGTTGGGCAGTCGAAAACAGGCCGTCAGCCAC
GCACCCGTCAGGGCCGGGTGTGTAAACTTTGACTACTCACGCACTCGCCGCTGCGTCGGGCGACGCGATTT
ACGGCCTGCCAACACCACGTCAACGTGGGAACCGCCTGTGTCGTCGGACGATGAAGCGAGCTCGCAGTCGA
AGCCCCTCGCCACCCAGCCGCCCGTCCTCGCCCTTTCGAACGCCCCCCCACGGCGGGTCTCCCCGACGCGA
GGTCGGCGCCGGCATACTCGCCTCCGACGCAACTAG
```

Figure 25

HSV-1 glycoprotein D (gD1; GI:330101)

```
 -25 mggtaarlga vilfvvivgl hgvrgkyala daslkmadpn rfrgkdlpvl dqltdppgvr
  36 rvyhiqaglp dpfqppslpi tvyyavlera crsvllnaps eapqivrgas edvrkqpynl
  96 tiawfrmggn caipitvmey tecsynkslg acpirtqprw nyydsfsavs ednlgflmha
 156 pafetagtyl rlvkindwte itqfilehra kgsckyalpl rippsaclsp qayqqgvtvd
 216 sigmlprfip enqrtvavys lkiagwhgpk apytstllpp elsetpnatq pelapedped
 276 salledpvgt vapqippnwh ipsiqdaatp yhppatpnnm gliagavggs llaalvicgi
 336 vywmhrrtrk apkrirlphi reddqpsshq plfy
```

HSV-1 glycoprotein D nucleic acid (gD1; GI:330100)

```
   1 gtggccccgg cccccaacaa aaatcacggt agcccggccg tgtgacacta tcgtccatac
  61 cgaccacacc gacgaacccc taagggggag gggccatttt acgaggagga ggggtataac
 121 aaagtctgtc tttaaaaagc aggggttagg gagttgttcg gtcataagct tcagcgcgaa
 181 cgaccaacta ccccgatcat cagttatcct taaggtctct tttgtgtggt gcgttccggt
 241 atggggggga ctgccgccag gttgggggcc gtgattttgt ttgtcgtcat agtgggcctc
 301 catggggtcc gcggcaaata tgccttggcg gatgcctctc tcaagatggc cgacccccaat
 361 cgctttcgcg gcaaagacct tccggtcctg gaccagctga ccgaccctcc gggggtccgg
 421 cgcgtgtacc acatccaggc gggcctaccg gacccgttcc agccccccag cctcccgatc
 481 acggtttact acgccgtgtt ggagcgcgcc tgccgcagcg tgctcctaaa cgcaccgtcg
 541 gaggcccccc agattgtccg cggggcctcc gaagacgtcc ggaaacaacc ctacaacctg
 601 accatcgctt ggtttcggat gggaggcaac tgtgctatcc ccatcacggt catggagtac
 661 accgaatgct cctacaacaa gtctctgggg gcctgtccca tccgaacgca gccccgctgg
 721 aactactatg acagcttcag cgccgtcagc gaggataacc tggggttcct gatgcacgcc
 781 cccgcgtttg agaccgccgg cacgtacctg cggctcgtga agataaacga ctggacggag
 841 attacacagt ttatcctgga gcaccgagcc aagggctcct gtaagtacgc cctcccgctg
 901 cgcatccccc cgtcagcctg cctctccccc caggcctacc agcagggggt gacggtggac
 961 agcatcggga tgctgccccg cttcatcccc gagaaccagc gcaccgtcgc cgtatacagc
1021 ttgaagatcg ccgggtggca cgggcccaag gccccataca cgagcaccct gctgcccccg
1081 gagctgtccg agacccccaa cgccacgcag ccagaactcg ccccggaaga ccccgaggat
1141 tcggccctct tggaggaccc cgtggggacg gtggcgccgc aaatcccacc aaactggcac
1201 atcccgtcga tccaggacgc cgcgacgcct taccatcccc cggccacccc gaacaacatg
1261 ggcctgatcg ccggcgcggt gggcggcagt ctcctggcag ccctggtcat ttgcggaatt
1321 gtgtactgga tgcaccgccg cactcggaaa gccccaaagc gcatacgcct cccccacatc
1381 cgggaagacg accagccgtc ctcgcaccag cccttgtttt actagatacc ccccttaat
1441 gggtgcgggg gggtcaggtc tgcggggttg ggatgggacc ttaactccat ataaagcgag
1501 tctggaaggg gggaaaggcg gacagtcgat aagtcggtag cgggggacgc gcacctgttc
1561 cgcctgtcgc acccacagct tttcgcgaa ccgtcccgtt ttcgggat
```

Figure 26

```
HSV-1 glycoprotein B (gB1; GI: 122831535)

1 pargcrwfvv wallgltlgv lvasaapssp gtpgvaaatq aanggpatpa ppapgpaptg
 61 dtkpkknkkp knppprpag dnatvaagha tlrehlrdik aentdanfyv cppptgatvv
121 qfeqprrcpt rpegqnyteg iavvfkenia pykfkatmyy kdvtvsqvwf ghrysqfmgi
181 fedrapvpfe evidkinakg vcrstakyvr nnlettafhr ddhetdmelk panaatrtsr
241 gwhttdlkyn psrveafhry gttvncivee vdarsvypyd efvlatgdfv ymspfygyre
301 gshtehtsya adrfkqvdgf yardlttkar atapttrnll ttpkftvawd wvpkrpsvct
361 mtkwqevdem lrseyggsfr fssdaisttf ttnlteypls rvdlgdcigk dardamdrif
421 arrynathik vgqpqyylan ggfliayqpl lsntlaelyv rehlreqsrk ppnptppppg
481 asanasveri kttssiefar lqftynhiqr hvndmlgrva iawcelqnhe ltlwnearkl
541 npnaiasatv grrvsarmlg dvmavstcvp vaadnvivqn smrissrpga cysrplvsfr
601 yedqgplveg qlgennelrl trdaiepctv ghrryftfgg gyvyfeeyay shqlsradit
661 tvstfidlni tmledhefvp levytrheik dsglldytev qrrnqlhdlr fadidtviha
721 danaamfagl gaffegmgdl gravgkvvmg ivggvvsavs gvssfmsnpf galavgllvl
781 aglaaaffaf ryvmrlqsnp mkalyplttk elknptspda sgegeeggdf deaklaeare
841 mirymalvsa mertehkakk kgtsallsak vtdmvmrkrr stnytqvpnk dgdadeddl HSV-1 glycoprotein B nucleic acid (gB1; GI: 122831534)

1 ccgcgcggg ggtgccggtg gttcgtcgta tgggcgctct tggggttgac gctggggtc
  61 ctggtggcgt cggcggctcc gagttccccc ggcacgcctg gggtcgcggc cgcgacccag
 121 gcggcgaacg ggggccctgc cactccggcg ccgccgccc ctggccccgc ccaacgggg
 181 gacacgaaac cgaagaagaa caaaaaaccg aaaaacccac cgccgccgcg ccccgccggc
 241 gacaacgcga ccgtcgccgc gggccacgcc accctgcgcg agcacctgcg ggacatcaag
 301 gcggagaaca ccgatgcgaa cttttacgtg tgcccaccc ccacgggcgc cacggtggtg
 361 cagttcgagc agccgcgccg ctgccgacc cggcccgagg gtcagaacta cacggagggc
 421 atcgcggtgg tcttcaagga gaacatcgcc ccgtacaagt tcaaggccac catgtactac
 481 aaagacgtca ccgtttcgca ggtgtggttc ggccaccgct actcccagtt tatggggatc
 541 tttgaggacc gcgccccgt cccccttgag gaggtggatc aaagatcaa cgccaagggg
 601 gtctgtcggt ccacgccaa gtacgtcgcg aacaacctgg agaccaccgc gtttcaccgg
 661 gacgaccacg agaccgacat ggagctgaaa ccggccaacg ccgcgacccg cacgagccgg
 721 ggctggcaca ccaccgacct caagtacaac ccctcgcggg tggaggcgtt ccaccggtac
 781 gggacgacgg taaactgcat cgtcgaggag gtggacgcgc gctcggtgta cccgtacgac
 841 gagtttgtgc tggcgactgg cgactttgtg tacatgtccc cgttttacgg ctaccgggag
 901 gggtcgcaca ccgaacacac cagctacgcc gccgaccgct tcaagcaggt cgacggcttc
 961 tacgcgcgcg acctcaccac caaggcccgg ccacggcgc cgaccacccg gaacctgctc
1021 acgaccccca gttcaccgt ggcctggac tgggtgccaa agcgccgtc ggtctgcacc
1081 atgaccaagt ggcaggaggt ggacgagatg ctgcgctccg agtacggcgg ctccttccga
1141 ttctctcccg acgccatatc caccaccttc accaccaacc tgaccgagta cccgctctcg
1201 cgcgtggacc tgggggactg catcggcaag gacgcccgcg acgccatgga ccgcatcttc
1261 gcccgcaggt acaacgcgac gcacatcaag gtgggccagc cgcagtacta cctggccaat
1321 gggggctttc tgatcgcgta ccagcccctt ctcagcaaca cgctcgcgga gctgtacgtg
1381 cgggaacacc tccgagagca gagccgcaag ccccaaacc ccacgcccc ccgcccgggg
1441 gccagcgcca acgcgtccgt ggagcgcatc aagaccacct cctccatcga gttcgcccgg
```

Figure 27

```
1501 ctgcagttta cgtacaacca catacagcgc catgtcaacg atatgttggg ccgcgttgcc
1561 atcgcgtggt gcgagctgca gaatcacgag ctgaccctgt ggaacgaggc ccgcaagctg
1621 aaccccaacg ccatcgcctc ggccaccgtg ggccggcggg tgagcgcgcg gatgctcggc
1681 gacgtgatgg ccgtctccac gtgcgtgccg gtcgccgcgg acaacgtgat cgtccaaaac
1741 tcgatgcgca tcagctcgcg gcccggggcc tgctacagcc gccccctggt cagctttcgg
1801 tacgaagacc agggcccgtt ggtcgagggg cagctggggg agaacaacga gctgcggctg
1861 acgcgcgatg cgatcgagcc gtgcaccgtg ggacaccggc gctacttcac cttcggtggg
1921 ggctacgtgt acttcgagga gtacgcgtac tcccaccagc tgagccgcgc cgacatcacc
1981 accgtcagca ccttcatcga cctcaacatc accatgctgg aggatcacga gtttgtcccc
2041 ctggaggtgt acacccgcca cgagatcaag gacagcggcc tgctggacta cacggaggtc
2101 cagcgccgca accagctgca cgacctgcgc tttgccgaca tcgacacggt catccacgcc
2161 gacgccaacg ccgccatgtt cgcgggcctg ggtgcgtttt tcgaggggat gggcgacctg
2221 gggcgcgcgg tcggcaaggt ggtgatgggc atcgtgggcg gcgtggtatc ggccgtgtcg
2281 ggcgtgtcct ccttcatgtc caacccctt ggggcgctgg ccgtgggtct gttggtcctg
2341 gccggcctgg cggcggcctt cttcgccttt cgctacgtca tgcggctgca gagcaacccc
2401 atgaaggccc tgtacccgct aaccaccaag gagctcaaga cccccaccag cccggacgcg
2461 tccggggagg gcgaggaggg cggcgacttt gacgaggcca agctagccga ggcccgggag
2521 atgatacggt acatggccct ggtgtcggcc atggagcgca cggaacacaa ggccaagaag
2581 aagggcacga gcgcgctgct cagcgccaag gtcaccgaca tggtcatgcg caagcgccgc
2641 agcaccaact acacccaagt tcccaacaaa gacggtgacg ccgacgagga cgacctgtga
```

Figure 27 cont'd.

HSV-1 glycoprotein H (gH1; GI: 290766017)

```
  1 mgnglwfvgv iilgvawgqv hdwteqtdpw fldglgmdrm ywrdtntgrl wlpntpdpqk
 61 pprgflappd elnlttaslp llrwyeerfc fvlvttaefp rdpgqllyip ktyllgrppn
121 aslpapttve ptaqpppsva plkgllynpv asvllrsraw vtfsavpdpe altfprgdnv
181 atashpsgpr dtppprppvg arrhptteld ithlhnastt wlatrgllrs pgryvyfsps
241 astwpvgiwt tgelvlgcda alvrarygre fmglvismhd sppvevmvvp agqtldrvgd
301 padenppgal pgppggpryr vfvlgsltra dngsaldalr rvggypeegt nyaqflsray
361 aeffsgdaga eqgprpplfw rltgllatsg fafvnaahan gavclsdllg flahsralag
421 laargaagca adsvffnvsv ldptarlqle arlqhlvaei lereqslalh algyqlafvl
481 dspsaydava psaahlidal yaeflggrvl ttpvvhralf yasavlrqpf lagvpsavqr
541 erarrsllia salctsdvaa atnadlrtal aradhqktlf wlpdhfspca aslrfdldes
601 vfildalaqa trsetpvevl aqqthglast ltrwahynal irafvpeash rcggqsanve
661 prilvpithn asyvvthspl prgigykltg vdvrrplflt yltatcegst rdieskrlvr
721 tqnqrdlglv gavfmrytpa gevmsvllvd tdntqqqiaa gptegapsvf ssdvpstall
781 lfpngtvihl lafdtqpvaa iapgflaasa lgvvmitaal agilkvlrts vpffwrre
```

HSV-1 glycoprotein H nucleic acid(gH1; GI: 290766003)

```
   1 ttattcgcgt ctccaaaaaa acgggacact tgtccggaga acctttagga tgccagccag
  61 ggcggcggta atcataacca cgcccagcgc agaggcggcc agaaacccgg gcgcaattgc
 121 ggccacgggc tgcgtgtcaa aggctagcaa atgaatgacg gttccgtttg gaaatagcaa
 181 caaggccgtg gacggcacgt cgctcgaaaa cacgctcggg gcgccctccg tcggccccggc
 241 ggcgatttgc tgctgtgtgt tgtccgtatc caccagcaac acagacatga cctccccggc
 301 tggggtgtag cgcataaaca cggcccccac gagccccagg tcgcgctggt tttgggtgcg
 361 caccagccgc ttggactcga tatcccgggt ggagccttcg catgtcgcgg tgaggtaggt
 421 taggaacagt gggcgtcgga cgtcgacgcc ggtgagcttg tagccgatcc cccggggcag
 481 aggggagtgg gtgacgacgt agctggcgtt gtgggtgatg ggtaccagga tccgtggctc
 541 gacgttggca gactgccccc cgcaccgatg tgaggcctca gggacgaagg cgcggatcag
 601 ggcgttgtag tgtgcccagc gcgtcagggt cgaggcgagg ccgtgggtct gctgggccag
 661 gacttcgacc ggggtctcgg atcgggtggc ttgagccagc gcgtccagga taaacacgct
 721 ctcgtctaga tcaaagcgca gggaggccgc gcatggcgaa aagtggtccg gaagccaaaa
 781 gagggttttc tggtggtcgg cccgggccag cgcggtccgg aggtcggcgt tggtcgctgc
 841 ggcgacgtcg gacgtacaca gggccgatgc tatcagaagg ctccggcggg cgcgttcccg
 901 ctgcaccgcc gaggggacgc ccgccaagaa cggctgccgg aggacagccg aggcgtaaaa
 961 tagcgcccgg tggacgaccg ggtggtcag cacgcggccc cctagaaact cggcatacag
1021 ggcgtcgatg agatgggctg cgctgggcgc cactgcgtcg tacgccgagg ggctatccag
1081 cacgaaggcc agctgatagc ccagcgcgtg taatgccaag ctctgttcgc gctccagaat
1141 ctcggccacc aggtgctgga gccgagcctc tagctgcagg cgggccgtgg gatccaagac
1201 tgacacatta aaaaacacag aatccgcggc acagcccgcg gccccgcggg cggccaaccc
1261 ggcaagcgcg cgcgagtggg ccaaaaagcc tagcaggtcg gagaggcaga ccgcgccgtt
1321 tgcgtgggcg gcgttcacga aagcaaaacc cgacgtcgcg agcagccccg ttaggcgcca
1381 gaagagaggg gggcgcgggc cctgctcggc gcccgcgtcc cccgagaaaa actccgcgta
1441 tgcccgcgac aggaactggg cgtagttcgt gccctcctcc gggtagccgc ccacgcggcg
1501 gagggcgtcc agcgcggagc cgttgtcggc ccgcgtcagg gaccctagga caaagacccg
1561 ataccggggg ccgcccgggg gcccgggaag agcccccggg gggttttcgt ccgcggggtc
1621 cccgacccga tctagcgtct ggcccgcggg gaccaccatc acttccaccg gagggctgtc
1681 gtgcatggat atcacgagcc ccatgaattc ccgcccgtag cgcgcgcgca ccagcgcggc
```

Figure 28

```
1741 atcgcacccg agcaccagct cccccgtcgt ccagatgccc acgggccacg tcgaggccga
1801 cggggagaaa tacacgtacc tacctgggga tctcaacagg ccccgggtgg ccaaccaggt
1861 cgtggacgcg ttgtgcaggt gcgtgatgtc cagctccgtc gtcgggtgcc gccgggcccc
1921 aaccggcggt cggggggggcg gtgtatcacg cggcccgctt gggtggctcg ccgtcgccac
1981 gttgtctccc cgcgggaacg tcagggcctc ggggtcaggg acggccgaaa acgttaccca
2041 ggcccgggaa cgcagcaaca cggaggcgac tggattgtac aagagaccct taagggggggc
2101 gaccgagggg ggaggctggg cggtcggctc gaccgtggtg ggggcgggca ggctcgcgtt
2161 cgggggccgg ccgagcaggt aggtcttcgg gatgtaaagc agctggccgg ggtcccgcgg
2221 aaactcggcc gtggtgacca atacaaaaca aaagcgctcc tcgtaccagc gaagaagggg
2281 cagagatgcc gtagtcaggt ttagttcgtc cggcggcgcc agaaatccgc gcggtggttt
2341 ttgggggtcg ggggtgtttg gcagccacag acgcccggtg ttcgtgtcgc gccagtacat
2401 gcggtccatg cccaggccat ccaaaaacca tgggtctgtc tgctcagtcc agtcgtggac
2461 ctgaccccac gcaacgccca aataataac ccccacgaac cataaaccat tccccat
```

Figure 28 cont'd.

HSV-1 glycoprotein L (gL1; GI: 32344856)

```
  1 mgilgwvgli avgilcvrgg lpsteyvirs rvarevgdil kvpcvplpsd dldwryetps
 61 ainyalidgi flryhcpgld tvlwdrhaqr aywvnpflfg agfledlshp afpadtqete
121 trlalykeir qaldsrkqaa shtpvkagcv nfdysrtrrc vgrqdlgltn rtsgrtpvlp
181 sddeaglqpk plttpspiia tsdptprrda atksrrrrph frgl
```

HSV-1 glycoprotein L nucleic acid (gL1; GI: GI: 32344855)

```
  1 atggggattt tgggttgggt cgggcttatt gccgttggga ttttgtgtgt gcggggggc
 61 ttgccttcaa ccgaatatgt tattcggagt cgggtggctc gagaggtggg ggatatatta
121 aaggtgcctt gtgtgccgct cccgtctgac gatcttgatt ggcgctacga gacccctcg
181 gctataaact atgctttgat agacggtata tttttgcgtt atcactgtcc cggattggac
241 acggtcttgt gggataggca cgcccagagg gcgtattggg ttaacccctt tttgtttggg
301 gcgggttttt tggaggactt gagtcatccc gcgtttcctg ccgacaccca ggaaacagaa
361 acgcgcttgg ccctttataa agagatacgc caggcgctgg acagtcgcaa gcaggccgcc
421 agccacacac ctgtgaaggc tgggtgtgtg aactttgact attcgcgcac ccgccgctgt
481 gtagggcgcc aggatttggg acttaccaac agaacgtctg gacggacccc ggttctgccg
541 tcggacgatg aagcgggcct gcagccgaag cccctcacca cgccgtcgcc catcatcgcc
601 acgtcggacc ccacccgcg acgggacgcc gccacaaaaa gcagacgccg acgaccccac
661 ttccggggcc tttaa
```

Figure 29

SUBUNIT VACCINES FOR HERPES VIRUSES AND METHODS OF USE

CROSS-REFERENCE TO RELATED APPLICATIONS

This application is the U.S. national phase application filed under 35 U.S.C. §371 claiming benefit to International Patent Application No. PCT/US2011/026188, filed on Feb. 25, 2011, which is entitled to priority under 35 U.S.C. §119(e) to U.S. Provisional Patent Application No. 61/308,856, filed Feb. 26, 2010, each of which application is hereby incorporated herein by reference in its entirety.

RELATED APPLICATIONS

This application claims benefit of priority from U.S. Provisional Application Ser. No. 61/308,856, filed Feb. 26, 2010, currently pending, the entire content of which is incorporated by reference as if fully set forth.

BACKGROUND OF THE INVENTION

1. Field of the Invention

The invention relates generally to herpes simplex virus (HSV) vaccines, and more specifically to vaccine compositions of single and multi-antigen HSV subunit proteins, with or without an adjuvant, such as a cationic liposome delivery vehicle, and the uses of these compositions to immunize against herpes simplex virus types.

2. Background Information

Herpes simplex viruses (HSVs) cause human diseases, including, for example, cold sores, eye and genital infections, neonatal infections and encephalitis. There are two serotypes of the virus, the oral form, termed HSV-1 and the genital form, termed HSV-2. HSV-2 infections are the leading cause of genital herpes and the incidence of HSV-2 infection has increased substantially during the past 30 years. It is estimated that in the USA, for example, from 40 to 60 million people are HSV-2 infected, with an incidence of 1-2 million infections and 600,000-800,000 clinical cases per year. Prevalence in the 30-40 year old population is about 30%. Overall prevalence is higher in women than men, especially among the younger population. Moreover, there is increasing evidence that HSV-2 infections contribute to the spread of HIV.

Herpes simplex viruses establish lifelong latent infections within sensory ganglia and therefore recurrent infections are common. Reactivation of virus, i.e. release from latency, occurs periodically over the lifetime of the individual and may result in recurrent infection but always involves virus shedding.

The structure of herpes viruses consists of a relatively large double-stranded, linear DNA genome encased within an icoshedral protein cage called the capsid, which is wrapped in a lipid bilayer called the envelope. The HSV envelope harbors 12 surface proteins and glycoproteins. To deliver the capsid containing the double-stranded DNA genome into the host cell, the virus fuses its envelope with the host's cellular membrane, either at the cell surface or within an endocytic vesicle, depending on the cell type. Among the envelope glycoproteins, gC, gB, gD, gH, and gL participate in viral-cell binding and entry.

HSV remains a significant human pathogen in spite of effective anti-viral therapy. Anti-viral drugs, such as acyclovir, used to treat HSV infections and recurrences, target DNA replication. However, these drugs are administered only when clinical signs appear, but virus shedding occurs even in the absence of clinical signs and is a major source of spread in the human population. Thus, there is an urgent need for an effective HSV vaccine both for prophylactic use and therapeutic use.

SUMMARY OF THE INVENTION

The present invention provides isolated HSV glycoprotein subunits acting as antigens, wherein the subunits are isolated or recombinantly produced, and utilized as compositions for the vaccination of mammalian subjects. In some embodiments, the glycoprotein subunit can be encoded by an isolated nucleic acid molecule.

The present invention includes compositions and methods of using such compositions to provide a therapeutic or prophylactic effect against HSV-1 and HSV-2. More particularly, the present invention relates to methods and compositions for HSV vaccines. The present invention provides for the use of three or more HSV glycoproteins, optionally, in combination with an adjuvant to vaccinate a mammalian subject against HSV viral strains. In particular embodiments, the composition includes glycoprotein B2 (gB2) and glycoprotein H2 (gH2) complexed with glycoprotein L2 (gL2). In some aspects, the composition further contains glycoprotein D2 (gD2).

In a first embodiment of the invention, there are provided compositions of isolated Herpes Simplex Virus (HSV) antigens including an isolated glycoprotein B (gB) or a fragment thereof, and an isolated glycoprotein H (gH) or a fragment thereof in a complex with glycoprotein L (gL) of a fragment thereof. In certain embodiments, the composition further includes an isolated glycoprotein D (gD) or fragment thereof. In particular embodiments, the glycoproteins are from HSV Type 2 (HSV-2). In one aspect, the glycoprotein B is glycoprotein B2 (gB2), the glycoprotein H is glycoprotein H2 (gH2), the glycoprotein L is glycoprotein L2 (gL2), and the glycoprotein D is glycoprotein D2 (gD2). In another aspect, the glycoprotein B is glycoprotein B1 (gB 1), the glycoprotein H is glycoprotein H1 (gH1), the glycoprotein L is glycoprotein L 1 (gL1), and the glycoprotein D is glycoprotein D1 (gD1).

In some embodiments of the present compositions and methods, the glycoprotein fragment is the ectodomain of the full length glycoprotein. For example, in particular embodiments, the fragment of gB includes amino acid residues 31-726 or amino acid residues 31-727 of gB2, and the fragment of gH includes amino acid residues 21-802 of gH2. In other embodiments, the fragment of gB includes amino acid residues 31-726 or amino acid residues 31-727 of gB2, the fragment of gH includes amino acid residues 21-802 of gH2, and the fragment of gD comprises amino acid residues 1-285 of gD2.

In particular embodiments there are provided, compositions of isolated herpes simplex virus (HSV) antigens including an isolated polypeptide containing amino acid residues 31-726 of glycoprotein B2 (gB2), and an isolated polypeptide containing amino acid residues 21-802 of glycoprotein H2 (gH2) in a complex with glycoprotein L2 (gL2). In one aspect, the composition further contains an isolated polypeptide containing amino acid residues 1-285 of glycoprotein D2 (gD2).

In preferred embodiments, the compositions of glycoproteins further contain an adjuvant. In one aspect, the adjuvant is a cationic liposome DNA complex (CLDC). In certain embodiments, the CLDC comprises a cationic liposome delivery vehicle and an isolated nucleic acid molecule. The isolated nucleic acid molecule is selected from the group consisting of i) an isolated nucleic acid molecule that is not operatively linked to a transcription control sequence, ii) an isolated bacterially-derived nucleic acid vector without a gene insert, iii) an isolated nucleic acid molecule comprising a non-coding nucleic acid sequence; iv) an isolated recombinant nucleic acid molecule encoding an immunogen operatively linked to a transcription control sequence, and iv) an oligonucleotide comprising a CpG motif. In particular embodiments, the composition contains HSV antigens including an isolated glycoprotein B (gB) or a fragment thereof, and an isolated glycoprotein H (gH) or a fragment thereof in a complex with glycoprotein L (gL) of a fragment thereof, and optionally, an isolated glycoprotein D (gD) or fragment thereof, wherein the composition is in CLDC adjuvant and the CLDC includes nucleic acid molecules encoding one or more of the antigens.

In other embodiments of the invention there are provided nucleic acid molecules encoding one or more of the antigens of the invention compositions or methods. In one aspect, the nucleic acid molecule encodes gH and gL. In another aspect the nucleic acid molecule encodes gH, gL, and gB. In still another aspect, the nucleic acid molecule encodes gH, gL, gB, and gD.

In other embodiments, there are provided compositions including an isolated nucleic acid molecule encoding a polypeptide containing amino acid residues 31-726 of glycoprotein B2 (gB2), and an isolated nucleic acid molecule encoding a polypeptide containing amino acid residues 21-802 of glycoprotein H2 (gH2), and an isolated nucleic acid molecule encoding glycoprotein L2 (gL2). In one aspect, the nucleic acids are complexed with a cationic liposome delivery vehicle to form a cationic liposome DNA complex (CLDC).

In certain embodiments, the compositions are for use in inducing an immune response against HSV in a mammalian subject. In some aspects, the use is for vaccinating a mammalian subject against HSV. In one aspect, the use is for vaccinating a mammalian subject against HSV-2. In some embodiments, the composition is effective to treat an HSV-2 infection. In some embodiments, the mammalian subject is a human. In one aspect, the subject has been diagnosed with an HSV-2 infection.

Compositions contemplated for vaccinating a mammalian subject against HSV-1 and -2 preferably include one or more antigenic herpes subunit proteins with a CLDC. Compositions contemplated for vaccinating a mammalian subject against HSV-1 or -2, may feature a full length, truncated, or mutated form of gB2, gH2/gL2 (a single subunit or multivalent subunits), and optionally, gD2. In particular aspects, the composition includes an adjuvant.

Additional embodiments of the featured compositions may include liposome delivery vehicles comprising lipids selected from the group consisting of multilamellar vesicle lipids and extruded lipids. Additional liposome delivery vehicle embodiments may include pairs of lipids selected from the group consisting of DOTMA and cholesterol; DOTAP and cholesterol; DOTIM and cholesterol; and DDAB and cholesterol.

Additional embodiments feature methods of vaccinating a mammalian subject against herpes virus by administering one of the compositions embodied in the present invention.

In another embodiment of the invention, there are provided methods for vaccinating a mammalian subject against HSV-2 by concurrently or sequentially administering to the subject an effective amount of an isolated polypeptide containing amino acid residues 31-726 of glycoprotein B2 (gB2) in an adjuvant, and an isolated polypeptide containing amino acid residues 21-802 of glycoprotein H2 (gH2) in a complex with glycoprotein L2 (gL2), wherein the complex is in an adjuvant. In particular embodiments, the method further includes concurrently or sequentially administering an isolated polypeptide comprising amino acid residues 1-285 of glycoprotein D2 (gD2) in an adjuvant. In one aspect, the adjuvant is a cationic liposome DNA complex (CLDC).

In still another embodiment of the invention, there are provided methods for vaccinating a mammalian subject against HSV-2 comprising concurrently or sequentially administering to the subject an effective amount of an isolated nucleic acid molecule encoding a polypeptide comprising amino acid residues 31-726 of glycoprotein B2 (gB2) complexed with a cationic liposome delivery vehicle, and an isolated nucleic acid molecule encoding a polypeptide comprising amino acid residues 21-802 of glycoprotein H2 (gH2) in combination with an isolated nucleic acid molecule encoding a glycoprotein L2 (gL2), wherein the combination is complexed with a cationic liposome delivery vehicle. In particular embodiments, the method further includes concurrently or sequentially administering an isolated nucleic acid molecule encoding a polypeptide comprising amino acid residues 1-285 of glycoprotein D2 (gD2) complexed with a cationic liposome delivery vehicle.

BRIEF DESCRIPTION OF THE DRAWINGS

The accompanying drawings, which are incorporated in and form a part of the specification, illustrates embodiments of the present invention, and together with the description serve to explain the principles of the invention.

FIG. 22 sets forth the amino acid sequence (SEQ ID NO:1) and nucleic acid sequence (SEQ ID NO:2) of an exemplary HSV-2 glycoprotein D (gD2; GenBank Accession No. ABU45462.1; GenBank ID Nos. GI:156072227 and GI:156072226).

FIG. 23 sets forth the amino acid sequence (SEQ ID NO:3) and nucleic acid sequence (SEQ ID NO:4) of an exemplary HSV-2 glycoprotein B (gB2; GenBank ID Nos. GI:295848592 and GI:295848591).

FIG. 24 sets forth the amino acid sequence (SEQ ID NO:5) and nucleic acid sequence (SEQ ID NO:6) of an exemplary HSV-2 glycoprotein H (gH2; GenBank ID No. GI:82013506).

FIG. 25 sets forth the amino acid sequence (SEQ ID NO:7) and nucleic acid sequence (SEQ ID NO:8) of an exemplary HSV-2 glycoprotein L (gL2; GenBank ID No. GI:136776).

FIG. 26 sets forth the amino acid sequence (SEQ ID NO:9) and nucleic acid sequence (SEQ ID NO:10) of an exemplary HSV-1 glycoprotein D (gD1; GenBank ID Nos. GI: 330101 and GI: 330100).

FIG. 27 sets forth the amino acid sequence (SEQ ID NO:11) and nucleic acid sequence (SEQ ID NO:12) of an exemplary HSV-1 glycoprotein B (gB1; GenBank ID Nos. GI: 122831535 and GI: 122831534).

FIG. 28 sets forth the amino acid sequence (SEQ ID NO:13) and nucleic acid sequence (SEQ ID NO:14) of an exemplary HSV-1 glycoprotein H (gH1; GenBank ID Nos. GI: 290766017 and 290766003).

FIG. 29 sets forth the amino acid sequence (SEQ ID NO:15) and nucleic acid sequence (SEQ ID NO:16) of an exemplary HSV-1 glycoprotein L (gL1; GenBank ID Nos. GI: 32344856 and 32344855).

DETAILED DESCRIPTION OF THE INVENTION

Figure 1:
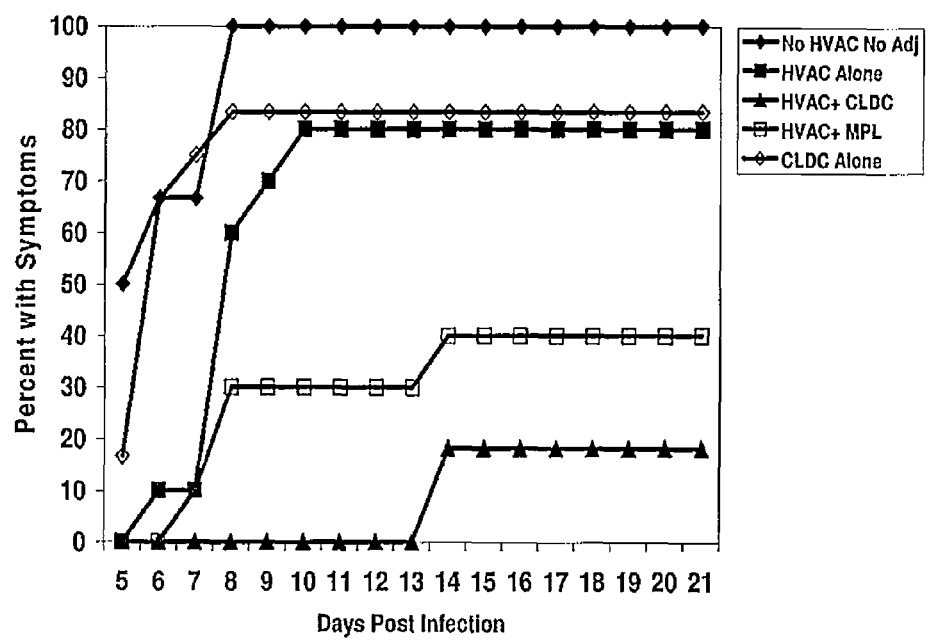
FIG. 1 shows a plot of the percentage of mice, which were vaccinated as indicated, exhibiting HSV symptoms over a period of 21 days post-HSV-2 infection. Clinical outcome through day 21 in mice challenged with HSV-2 is shown. 60 mice (i.e., 12 mice/group with five groups) were either vaccinated according to the following groups: Group 1) no HVAC/no adjuvant; Group 2) whole detergent-inactivated HSV-2 lysate (HVAC) alone; Group 3) HVAC+CLDC; Group 4) HVAC+MPL (3-deacylated monophosphoryl lipid A); or Group 5) CLDC alone.

HSV glycoproteins function in virus entry, spread, immune evasion and inhibition of apoptosis. These glycoproteins include gD, the receptor binding protein, gB, and the gH/gL complex, which contribute to the release of the capsid inside the cell to begin replication. Other glycoproteins, such as gC and gE, also are involved in the pathway of virus invasion and infection. The virus cascade of events consists of a series of coordinated steps and conformational changes.

Both the humoral and cell-mediated immune responses are important for controlling HSV infection. Although both CD4$^+$ and CD8$^+$ T cells play an important role in protection from HSV infection in humans and in murine models, the construction of an effective prophylactic or therapeutic vaccine against HSV is still needed. The present invention identifies particular immunogenic glycoprotein antigens, with or without an adjuvant to enhance the immune response.

Herpes Simplex Viruses.

Billions of people worldwide are infected with either Herpes simplex virus type 1 (HSV-1) or Herpes simplex virus type 2 (HSV-2). HSV-1 and HSV-2 are two members of the HSV family of α-herpesviruses, which establish lifelong latent infection in sensory neurons and lead to chronic herpes disease. HSV-1 infection causes facial/ocular disease, while HSV-2 is the leading cause of genital herpes, although both viruses can be found at oral and genital sites. Indeed, the incidence of HSV-1 genital disease is increasing and approximates that of HSV-2 in certain countries. HSV-1 and HSV-2 encode approximately 80 genes, are structurally similar, and share approximately 80% genome sequence homology.

Although many, if not most, HSV-2 infections are asymptomatic or unrecognized, symptomatic primary genital HSV infection is characterized by vesicular and ulcerative skin lesions, which can result in neurologic and urologic complications. During initial infection, a long term persistent or latent infection is established in ganglion neurons, which can reactivate and cause recurrent genital disease or asymptomatic viral shedding. Recurrent herpes infection is a chronic, intermittent disease characterized by both symptomatic and asymptomatic periods of viral replication in the epithelial cells at mucosal sites or other peripheral sites. (Koelle D M et al., J Immunol. 166:4049, 2001). Both symptomatic and asymptomatic herpes infection can lead to transmission to seronegative individuals. Indeed, most transmission occurs during periods of unrecognized shedding. One of the most serious complications of genital herpes occurs when the virus is transmitted from mother to neonate. Infection of the neonate causes significant morbidity and mortality, even with proper antiviral therapy (Sacks S L et al., Antiviral Res. 63S1:S27, 2004). Genital herpes infection also increases the risk of acquiring HIV infection and increases shedding of HIV in genital lesions (Posovad C M et al., Proc Natl Acad Sci USA. 94:10289, 1997).

HSV-2 infection induces both humoral and T-cell mediated immunity; however, the mechanisms that contribute to long term control of genital herpes are not understood. Studies from animal models of HSV infection and human studies indicate that high levels of neutralizing antibodies and innate immunity (natural killer (NK) cells, interferon, and macrophages) contribute to protection from HSV infection but the major determinants of HSV protection are both $CD4^+$ and $CD8^+$ T cells (Ahmad A et al., J Virol. 74(16): 7196-7203, 2000; Aurelian L et al., J Gen Virol. 68:2831, 1987; Milligan G N et al., J Immunol. 160(12):6093, 1998.; Koelle et al, 1998). Clearance of virus from recurrent lesions is more closely correlated to T cell immunity. Thus, when a recurrent lesion occurs, mononuclear cells, primarily $CD4^+$ T cells, infiltrate the lesion as early as two days after formation, followed by an influx of $CD8^+$ T cells at later times (Cunningham A L et al., J Clin Invest. 75:226, 1985). Although both HSV-specific $CD4^+$ and $CD8^+$ T cell responses are detected, clearance of HSV-2 from lesions correlates with a CD8+ cytotoxic T lymphocyte (CTL) response (Koelle et al., J Clin Invest. 101:1500, 1998). To counteract the host immune response, HSV has developed a number of immune evasion strategies, such as disruption of antigen peptide processing and presentation by MHC Class I molecules (Jugovic P et al., J Virol. 72:5076, 1998; Tomazin R et al., J Virol. 72(3):2560, 1998), interference with complement activation and antibody binding (Friedman H M et al., J Immunol. 165:4528, 2000; Nagashunmugam T et al., J Virol. 72:5351, 1998), or inhibition of dendritic cell maturation, which reduces efficient antigen presentation and CTL priming (Salio M et al., Eur J Immunol. 29:3245, 1999; Pollara G et al., J Infect Dis. 187:1513, 2003). IFNγ, a Th1 cytokine, is expressed in lesions by T cells (predominantly $CD4^+$), and partially restores MHC I expression and also stimulates MHC II expression, thus contributing to T cell-mediated immune control of HSV replication (Cunningham A L et al., J Clin Investig. 83:490, 1989; Kokuba H et al., J Investig Dermatol. 113:808, 1999; Mikloska Z et al., J Gen Virol. 79:353, 1998). Such mechanisms provide HSV with strategies to counteract the immune system and establish a lifelong persistent infection in the host.

HSV has a lipid envelope, bearing about 12 surface proteins and glycoproteins. To deliver the capsid containing the double-stranded DNA genome into the host cell, HSV must fuse its envelope with a cellular membrane, either at the cell surface or within an endocytic vesicle, depending on the cell type. Among the envelope glycoproteins, gC, gB, gD, gH, and gL, appear to participate in viral cell binding and entry.

All herpesviruses encode genes for gB, gH, and gL, and these three proteins constitute their core fusion machinery. HSV attaches to cells by binding to heparan sulfate proteoglycan (HSPG) via gC, and by binding of gD to one of three cellular receptors: nectin-1, herpesvirus entry mediator (HVEM), or a modified heparan sulfate. Structural and biochemical studies have shown that gD undergoes conformational changes to permit receptor binding and to potentiate fusion.

Binding of gD to its receptor nectin-1 triggers an interaction between gB and gH/gL that is on the pathway to fusion. Based on what happens to other viral fusion proteins upon activation of the triggering signal (either receptor binding or lowered pH or both), it is likely that receptor binding by gD (and possibly pH as well) causes gB and/or gH/gL to interact and to undergo conformational changes that bring the viral and cell membranes together to facilitate fusion.

Recombinant Herpes Simples Virus glycoprotein D, glycoprotein B, glycoprotein H, and glycoprotein L of both Types 1 and 2 are provided, including fragments, precursors and analogs, as well as DNA sequences encoding for the precursors and the mature amino acid sequence and fragments thereof.

As used herein, the term "precursor," when used in reference to a protein refers to an amino acid sequence that includes an N-terminal signal peptide and the mature protein. Accordingly, the terms "mature protein" or "full length protein" refer to the amino acid sequence including all domains of the native sequence except the signal peptide.

As used herein, the term "ectodomain" refers to the portion of an integral membrane protein that extends into the extracellular space (i.e., the space outside the cell). The ectodomain generally does not include the signal peptide. The ectodomain of an integral membrane protein can be readily identified by the skilled artisan using sequence analysis tools known in the art. In preferred embodiments of the present compositions and methods, fragments corresponding to the ectodomain of each glycoprotein are used. The ectodomains of exemplary gD, gB, and gH proteins from HSV-1 (termed gD1, gB1, and gH1) and HSV-2 (termed gD2, gB2, and gH2) are described below. Full-length or truncated forms of the ectodomain may be used in the present compositions and methods.

FIGS. 22-29 provide the amino acid and encoding nucleotide sequences of exemplary gD, gB, gH, and gL proteins from HSV-1 and HSV-2. The nucleotide sequences encoding a glycoprotein may be varied by methods known to the skilled artisan. For example, a nucleotide sequence encoding an entire precursor or mature glycoprotein polypeptide, or a portion thereof may be joined in-frame to a nucleotide sequence encoding one or more different precursor or mature glycoprotein polypeptides, or a portions thereof. In this way, a single nucleic acid molecule may be generated that encodes two or more glycoprotein polypeptides or portions thereof. In another example, a nucleotide sequence encoding a portion of a precursor or mature glycoprotein polypeptide may be joined in-frame with another portion of the same glycoprotein to generate a nucleic acid molecule encoding a glycoprotein having a deletion. In preferred embodiments, the transmembrane domain or anchor is deleted from glycoproteins that are membrane proteins.

In addition, particular codons may be modified so as the encode the same amino acids, but provide more efficient expression in accordance with the nature of the host. For example, the codons may be modified in accordance with the frequency of occurrence of a particular codon in one or more proteins or groups of proteins, e.g., glycolytic proteins, which contribute to a high proportion of the total proteins of a particular host, e.g., human. In some instances one or more codons may be modified to code for a different amino acid, substituting one amino acid for another amino acid, where the effect of the change is not detrimental to the immunogenicity of the protein or to other biological factors of interest. Such changes may be made to enhance the immunogenicity of the polypeptide, facilitate conjugating the polypeptide to a carrier protein, or the like. It may be desirable in some instances to add amino acids to the N-terminus or C-terminus, where such additional amino acids may provide-for a desired result. This can be readily achieved by providing for additional codons at the 5'- or 3'-termini of the sequence encoding the mature glycoprotein or its precursor.

HSV Glycoprotein D (gD).

gD is a type I integral membrane protein with an ectodomain of 316 residues organized around a core immunoglobulin (Ig) V-fold with N- and C-terminal extensions that wrap around the core. Most receptor binding activities and conformational changes involve the N- and C-terminal extensions.

In the unbound form, the C-terminus folds back around the Ig fold and is anchored near the N-terminus. Nectin-1 binds to the gD core at a position distinct from where HVEM binds. However, the gD C-terminus normally obscures the binding sites for both nectin-1 and HVEM and necessitates displacement of this region. Furthermore, this conformational change to gD and/or the residues of gD that are exposed by receptor binding likely activate the fusion machinery. Triggering of fusion by gD/receptor binding would occur only when the virus is close to a membrane, thereby preventing premature activation of the fusion machinery. The gD protein also includes proline-rich region (a.a. 260-285), termed the pro-fusion domain (PFD) that is important for gD function after receptor binding. A portion of this segment is unresolved in all X-ray structures, suggesting it is highly flexible. It may act as a hinge that allows another part of gD to activate the fusion protein(s) or contact these proteins directly. The PFD concept agrees with structural studies regarding the ectodomain C-terminus. Analogous proline-rich regions connect functional domains of other viral envelope proteins. Alternatively, the conformational change that takes place upon receptor binding may expose key residues of the gD Ig core, normally hidden, that are directly involved in triggering downstream events involving gB and gH/gL.

HSV-2 glycoprotein D contains 393 amino acid residues. An exemplary gD2 amino acid sequence is set forth in GenBank ID No. GI:156072227, which is provided in FIG. 22 as SEQ ID NO:1. The signal sequence of gD2 encompasses residues −25 to −1 of the sequence set forth in FIG. 22, and the ectodomain of gD2 encompasses approximately residues 1-316, with a soluble gD2 ectodomain encompassing residues 1-306. The skilled artisan will readily recognize that the referenced specific sequence was obtained from gD2 from a particular HSV-2 strain and that the analogous sequences from another HSV-2 strain may vary. Accordingly, in some embodiments of the present compositions and methods, the gD2 antigen may be 80% identical to the sequence set forth in SEQ ID NO:1. In other embodiments, gD2 antigen may be 85%, 90%, 95%, 96%, 97%, 98%, or even 99% identical to the sequence set forth in SEQ ID NO:1. The skilled artisan can readily identify and confirm the immunogenicity of these sequences using methods known in the art and provided herein. In some embodiments of the present compositions and methods, a full length gD2 protein is used. In some aspects, the ectodomain of gD2 is used. In other embodiments, a truncated, mutated, or chimeric form of gD2 is used. For example, truncated form gD-2t(285) contains residues 1-285 and is a preferred aspect of the invention. Other truncated forms include those with deletions between residues 260-306; preferably between 275-285 resulting in truncated forms such as amino acid residues 1-260 and 1-275. (Krummenacher et al. 2005 EMBO Journal, 24:4144-4153.)

HSV-1 glycoprotein D contains 394 amino acid residues. An exemplary gD1 amino acid sequence is set forth in GenBank ID No. GI: 330101, which is provided in FIG. 26 as SEQ ID NO:9. The signal sequence of gD1 encompasses residues −25 to −1 of the sequence set forth in FIG. 26 and the ectodomain of gD1 encompasses residues 1-316. The skilled artisan will readily recognize that the referenced specific sequence was obtained from gD1 from a particular HSV-1 strain and that the analogous sequences from another HSV-1 strain may vary. Accordingly, in some embodiments of the present compositions and methods, the gD1 antigen may be 80% identical to the sequence set forth in SEQ ID NO:9. In other embodiments, gD2 antigen may be 85%, 90%, 95%, 96%, 97%, 98%, or even 99% identical to the sequence set forth in SEQ ID NO:9. The skilled artisan can readily identify and confirm the immunogenicity of these sequences using methods known in the art and provided herein. In some embodiments of the present compositions and methods, a full length gD1 protein is used. In some aspects, the ectodomain of gD1 is used. In other embodiments, a truncated, mutated, or chimeric form of gD1 is used. For example, truncated form gD-1t(285) contains residues 1-285 and is a preferred aspect of the invention. Other truncated forms include those with deletions between residues 260-306; preferably between 275-285 resulting in truncated forms such as amino acid residues 1-260 and 1-275.

Various aspects of the gD1 and gD2 glycoprotein are found in U.S. Pat. Nos. 4,762,708; 5,149,660; 5,654,174; and 5,814,486.

HSV Glycoprotein B (gB).

The gB glycoprotein is an elongated trimer with a long central alpha-helix in each protomer. Each protomer contains five distinct structural domains. Domains I and II have features that resemble those of pleckstrin homology (PH) domains. Remarkably, much of the architecture of gB is similar to that of the post-fusion form of VSV G, implying that gB is a viral fusogen and that the solved structure of gB may be a post-fusion form. The alpha-helical coiled-coil core relates gB to class I viral membrane fusion glycoproteins. However, both gB and VSV G have two extended beta hairpins with hydrophobic tips (domain I of gB and domain IV of VSVG) that are homologous to fusion loops of class II fusion proteins. Members of both classes accomplish fusion through a large-scale conformational change (fold-back) triggered by a signal from a receptor-binding component. It is likely that gB also undergoes a fold-back type of change.

HSV-2 glycoprotein B contains 901 amino acid residues. The gB protein may be divided into four domains beginning at the N-terminus: a signal sequence, followed by an ectodomain, a transmembrane domain or "anchor," and a cytoplasmic domain. An exemplary gB2 amino acid sequence is set forth in GenBank ID No. GI:295848592, which is provided in FIG. 23 as SEQ ID NO:3. The ectodomain of gB2 encompasses approximately residues 31-726. The skilled artisan will readily recognize that the referenced specific sequence was obtained from gB2 from a particular HSV-2 strain and that the analogous sequences from another HSV-2 strain may vary. Accordingly, in some embodiments of the present compositions and methods, the gB2 antigen may be 80% identical to the sequence set forth in SEQ ID NO:3. In other embodiments, gB2 antigen may be 85%, 90%, 95%, 96%, 97%, 98%, or even 99% identical to the sequence set forth in SEQ ID NO:3. The skilled artisan can readily identify and confirm the immunogenicity of these sequences using methods known in the art and provided herein. In some embodiments of the present compositions and methods, a full length gB2 protein is used. In some aspects, the ectodomain of gB2 is used. In other embodiments, a truncated, mutated, or chimeric form of gB2 is used. For example, a truncated form gB2 containing residues 31-726 and is a preferred aspect of the invention. In another preferred aspect, a truncated form gB2 containing residues 31-727 is used in the disclosed compositions and methods.

HSV-1 glycoprotein B may contain 899-904 amino acid residues, depending on the strain from which it is obtained. The gB protein may be divided into four domains beginning at the N-terminus: a signal sequence, followed by an ectodomain, a transmembrane domain or "anchor," and a cytoplasmic domain. An exemplary gB 1 amino acid sequence is set forth in GenBank ID No. GI: 122831535, which is provided in FIG. 27 as SEQ ID NO:11. The ectodomain of gB 1 encompasses approximately residues 34-727. The skilled artisan will readily recognize that the referenced specific sequence was obtained from gB 1 from a particular HSV-1 strain and that the analogous sequences from another HSV-1 strain may vary. Accordingly, in some embodiments of the present compositions and methods, the gB1 antigen may be 80% identical to the sequence set forth in SEQ ID NO:11. In other embodiments, gB1 antigen may be 85%, 90%, 95%, 96%, 97%, 98%, or even 99% identical to the sequence set forth in SEQ ID NO:11. The skilled artisan can readily identify and confirm the immunogenicity of these sequences using methods known in the art and provided herein. In some embodiments of the present compositions and methods, a full length gB1 protein is used. In some aspects, the ectodomain of gB1 is used. In other embodiments, a truncated, mutated, or chimeric form of gB1 is used. For example, a truncated form gB1 containing residues 31-727 and is a preferred aspect of the invention. In another preferred aspect, a truncated form gB1 containing residues 31-728 is used in the disclosed compositions and methods.

Various gB glycoproteins also are described in U.S. Pat. Nos. 5,244,792; 5,648,079; and 5,759,814.

HSV Glycoprotein H/L (gH/gL).

Glycoproteins gH and gL form a non-covalently linked heterodimer that is associated with HSV entry and cell fusion. The proper processing and transport of gH requires it to be co-expressed with gL as a heterodimer. For example, it has been shown that when HSV-1 gH is expressed in the absence of gL, it is retained in the endoplasmic reticulum in an antigenically and structurally immature form. Therefore, gL is a chaperone for gH transport, but it may play an additional role, as some anti-gL MAbs inhibit virus spread. Interestingly, HSV gL contains an N-terminal signal peptide sequence, but lacks a hydrophobic transmembrane region (TMR). (See U.S. Pat. Nos. 5,807,557; 6,156,319; and 6,541,459.) HSV-2 contains a similar complex of gH2/gL2.

HSV-2 glycoprotein H is a single pass type I membrane protein and contains 838 amino acid residues. The gH protein may be divided into four domains beginning at the N-terminus: a signal sequence, followed by an ectodomain, a transmembrane domain or "anchor," and a cytoplasmic domain. An exemplary gH2 amino acid sequence is set forth in GenBank ID No. GI:82013506, which is provided in FIG. 24 as SEQ ID NO:5. The full ectodomain of gH2 encompasses approximately residues 19-803. The skilled artisan will readily recognize that the referenced specific sequence was obtained from gH2 from a particular HSV-2 strain and that the analogous sequences from another HSV-2 strain may vary. Accordingly, in some embodiments of the present compositions and methods, the gH2 antigen may be 80% identical to the sequence set forth in SEQ ID NO:5. In other embodiments, gH2 antigen may be 85%, 90%, 95%, 96%, 97%, 98%, or even 99% identical to the sequence set forth in SEQ ID NO:5. The skilled artisan can readily identify and confirm the immunogenicity of these sequences using methods known in the art and provided herein. In some embodiments of the present compositions and methods, a full length gH2 protein is used. In some aspects, the ectodomain of gH2 is used. In other embodiments, a truncated, mutated, or chimeric form of gH2 is used. For example, a truncated form gH2 containing residues 21-802 and is a preferred aspect of the invention.

HSV-1 glycoprotein H is a single pass type I membrane protein and contains 838 amino acid residues. The gH protein may be divided into four domains beginning at the N-terminus: a signal sequence, followed by an ectodomain, a transmembrane domain or "anchor," and a cytoplasmic domain. An exemplary gH1 amino acid sequence is set forth in GenBank ID No. GI: 290766017, which is provided in FIG. 28 as SEQ ID NO:13. The ectodomain of gH1 encompasses approximately residues 19-803. The skilled artisan will readily recognize that the referenced specific sequence was obtained from gH1 from a particular HSV-1 strain and that the analogous sequences from another HSV-1 strain may vary. Accordingly, in some embodiments of the present compositions and methods, the gH1 antigen may be 80% identical to the sequence set forth in SEQ ID NO:13. In other embodiments, gH1 antigen may be 85%, 90%, 95%, 96%, 97%, 98%, or even 99% identical to the sequence set forth in SEQ ID NO:13. The skilled artisan can readily identify and confirm the immunogenicity of these sequences using methods known in the art and provided herein. In some embodiments of the present compositions and methods, a full length gH1 protein is used. In some aspects, the ectodomain of gH1 is used. In other embodiments, a truncated, mutated, or chimeric form of gH1 is used. For example, a truncated form gH1 containing residues 21-802 and is a preferred aspect of the invention. The skilled artisan will recognize that the positions of the recited truncation may differ slightly in glycoproteins from different HSV strains, and can readily identify the analogous sequences using well-known sequence analysis tools.

HSV-2 glycoprotein L is viral envelope protein and contains 224 amino acid residues. An exemplary gL2 amino acid sequence is set forth in GenBank ID No. GI:136776, which is provided in FIG. 25 as SEQ ID NO:7. The gL protein contains a signal sequence, followed by the envelope glycoprotein L, which encompasses approximately residues 17-224. The skilled artisan will readily recognize that the referenced specific sequence was obtained from gL2 from a particular HSV-2 strain and that the analogous sequences from another HSV-2 strain may vary. Accordingly, in some embodiments of the present compositions and methods, the gL2 antigen may be 80% identical to the sequence set forth in SEQ ID NO:7. In other embodiments, gL2 antigen may be 85%, 90%, 95%, 96%, 97%, 98%, or even 99% identical to the sequence set forth in SEQ ID NO:7. The skilled artisan can readily identify and confirm the immunogenicity of these sequences using methods known in the art and provided herein. In some embodiments of the present compositions and methods, a full length gL2 protein is used. In some aspects, the glycoprotein without the signal sequence is used. In other embodiments, a truncated, mutated, or chimeric form of gL2 is used. For example, a truncated form gL2 containing residues 17-224 and is a preferred aspect of the invention.

HSV-1 glycoprotein L is viral envelope protein and contains 224 amino acid residues. An exemplary gL1 amino acid sequence is set forth in GenBank ID No. GI: 32344856, which is provided in FIG. 29 as SEQ ID NO:15. The gL protein contains a signal sequence, followed by the envelope glycoprotein L, which encompasses approximately residues 17-224. The skilled artisan will readily recognize that the referenced specific sequence was obtained from gL1 from a p' articular HSV-1 strain and that the analogous sequences from another HSV-1 strain may vary. Accordingly, in some embodiments of the present compositions and methods, the gL1 antigen may be 80% identical to the sequence set forth in SEQ ID NO:15. In other embodiments, gL1 antigen may be 85%, 90%, 95%, 96%, 97%, 98%, or even 99% identical to the sequence set forth in SEQ ID NO:15. The skilled artisan can readily identify and confirm the immunogenicity of these sequences using methods known in the art and provided herein. In some embodiments of the present compositions and methods, a full length gL1 protein is used. In some aspects, the glycoprotein without the signal sequence is used. In other embodiments, a truncated, mutated, or chimeric form of gL 1 is used. For example, a truncated form gL 1 containing residues 17-224 and is a preferred aspect of the invention.

Other HSV Antigens

Glycoprotein gC, which is a viral envelope glycoprotein, binds to the cell surface particle: heparin sulfate; whereas gE is a membrane glycoprotein with a large ectodomain that is expressed on the virion envelope and the surface of infected cells. Glycoprotein gA also is one of the major glycoproteins found in the envelope of the virus particle.

Additional embodiments may include the gD2, gB2, and gH2/gL2 antigens, but may also contain a human T cell HSV-2 antigen, such as ICP27, ICP4, or VP22.

HSV Vaccines

The compositions of the present invention may be used as vaccines. In one example, the vaccine includes an immunologically-effective amount of an HSV-1 or HSV-2 glycoprotein, which preferably is purified, isolated or prepared by recombinant nucleic acid methods, and an adjuvant, which is pharmaceutically or therapeutically acceptable.

A preferred composition consists essentially of isolated glycoprotein B (gB) or a fragment thereof, and an isolated glycoprotein H (gH) or a fragment thereof in a complex with glycoprotein L (gL) or a fragment thereof and adjuvant. A more preferred composition consists essentially of the ectodomain of glycoprotein B (gB), and the ectodomain of glycoprotein H (gH) or a fragment thereof in a complex with glycoprotein L (gL) and adjuvant. Another preferred composition consists essentially of an isolated glycoprotein D (gD), an isolated glycoprotein B (gB) or a fragment thereof, and an isolated glycoprotein H (gH) or a fragment thereof in a complex with glycoprotein L (gL) or a fragment thereof and adjuvant. A more preferred composition consists essentially of the ectodomain of glycoprotein D (gD), the ectodomain of glycoprotein B (gB), and the ectodomain of glycoprotein H (gH) or a fragment thereof in a complex with glycoprotein L (gL) and adjuvant.

CLDC Adjuvant

Cationic liposome/DNA complexes (CLDC) include a cationic liposome delivery vehicle and an isolated nucleic acid molecule. In certain embodiments, the isolated nucleic acid molecule is selected from the group consisting of i) an isolated nucleic acid molecule that is not operatively linked to a transcription control sequence, ii) an isolated bacterially-derived nucleic acid vector without a gene insert, iii) an isolated nucleic acid molecule comprising a non-coding nucleic acid sequence; iv) an isolated recombinant nucleic acid molecule encoding an immunogen operatively linked to a transcription control sequence, and iv) an oligonucleotide comprising a CpG motif. In particular embodiments, the CLDC has a nucleic acid:lipid complex ratio of from about 1:1 to about 1:64. In preferred embodiments, the nucleic acid:lipid complex has a ratio of from about 1:10 to 1:40. CLDC adjuvants are further described in U.S. Pat. No. 6,693,086, the content of which is hereby incorporated by reference as if fully set forth herein.

Liposome delivery vehicles suitable for use in any of the compositions and methods of the present invention can include any liposomes. Particularly preferred liposomes are cationic liposomes. Other preferred liposomes include multilamellar vesicle lipids and extruded lipids, with multilamellar vesicle lipids being more preferred. Liposome compositions can include, but are not limited to, pairs of lipids selected from DOTMA and cholesterol, DOTAP and cholesterol, DOTIM and cholesterol, and DDAB and cholesterol, with DOTAP and cholesterol being particularly preferred.

In another embodiment of the present invention, a vaccine or composition further comprises a pharmaceutically acceptable excipient. As used herein, a "pharmaceutically acceptable excipient" refers to any substance suitable for delivering a therapeutic composition useful in the method of the present invention to a suitable in vivo or ex vivo site. Preferred pharmaceutically acceptable excipients are capable of maintaining a nucleic acid molecule and/or antigen in a form that, upon arrival of the nucleic acid molecule and/or antigen to a cell, the nucleic acid molecule and/or protein are capable of contacting and/or entering the cell and eliciting an immune response at or near the site of the cell.

Suitable excipients for use in the present invention include excipients or formularies that transport, but do not specifically target the vaccine to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Particularly preferred excipients include non-ionic diluents, with preferred non-ionic buffer being 5%-10% sucrose or 5-10% lactose in water.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Therapeutic compositions of the present invention can be sterilized by conventional methods and/or lyophilized.

Administration

The glycoprotein subunit or antigen may be administered with or without an adjuvant, such as CLDC. Moreover, one or more glycoproteins may be combined for administration with or without an adjuvant. Preferably, three or four antigens are combined, such as gB2 and gH/gL; or gB2, gD2, and gH/gL.

The single or multivalent subunit HSV vaccines may be administered to a mammal, such as a human, by methods known in the art, such as subcutaneously, intramuscularly, orally, intravenously, intradermally, intranasally or intravaginally. The antigens or subunits are formulated in a pharmaceutically acceptable excipient or carrier, which is suitable for the chosen route of administration.

Many of the above-described routes of administration, including intravenous, intraperitoneal, intradermal, and intramuscular administrations can be performed using methods standard in the art. Aerosol (inhalation) delivery can also be performed using methods standard in the art (see, for example, Stribling et al., Proc. Natl. Acad. Sci. USA 189: 11277-11281, 1992, which is incorporated herein by reference in its entirety). Oral delivery can be performed by complexing a composition of the present invention to a carrier capable of withstanding degradation by digestive enzymes in the gut of an animal. Examples of such carriers, include plastic capsules or tablets, such as those known in the art. One method of local administration is by direct injection. The dose of vaccine to be used varies depending upon a number of factors, such as the age, sex, and weight of the individual as well as the chosen route of administration.

One aspect of the invention pertains to the methods for vaccinating a mammalian subject against HSV-1 or HSV-2 comprising administering to the subject an effective amount of the compositions described above. For example, a method for vaccinating a mammal, such as a human, against HSV-2 comprises concurrently or sequentially administering to the mammal an effective amount of each subunit of interest, wherein the use of an adjuvant is optional. Such adjuvants include those that induce a Th-1 immune response, including, but not limited to, aluminium hydroxide (alum), aluminium phosphate, 3-deacylated monophosphoryl lipid A (MPL), and/or a CLDC. However, the use of CLDC is most preferred.

An effective administration protocol (i.e., administering a vaccine or therapeutic composition in an effective manner) comprises suitable dose parameters and modes of administration that result in elicitation of an immune response in a mammal that has been infected with HSV or, preferably so that the mammal is protected from infection. Effective dose parameters can be determined using methods standard in the art for a viral infection. Such methods include, for example, determination of survival rates, side effects (i.e., toxicity) and progression or regression of disease.

A suitable single dose size is a dose that is capable of eliciting an immune response in a mammal with an HSV infection, when administered one or more times over a suitable time period. One of skill in the art can readily determine appropriate single dose sizes for systemic administration based on the size of a mammal and the route of administration. One of skill in the art can monitor the effectiveness of the immunization by measuring, for example, cytokine responses, cytotoxicity, antibody production, by enumerating antigen-specific T cells, or monitoring delayed type hypersensitivity (DTH) responses.

An appropriate single dose size for the composition based on the amount of immunogen is an amount of the vaccine that delivers from about 1 µg immunogen per individual mammal to about 50 mg immunogen per individual mammal, preferably from about 1 µg immunogen per individual mammal to about 1 mg immunogen per individual mammal, and more preferably from about 1 µg immunogen per individual mammal to about 100 µg immunogen per individual mammal, and even more preferably from about 10 µg immunogen per individual mammal to about 100 µg immunogen per individual mammal. In one embodiment, an appropriate single dose size for the composition based on the amount of immunogen is an amount of the vaccine that delivers at least about 0.1 µg immunogen per individual mammal, and more preferably at least about 1 µg immunogen per individual mammal, and m ore preferably, at least about 5 µg immunogen per individual mammal, and more preferably at least about 10 µg immunogen per individual mammal. In particular aspects the amount of immunogen delivered is from about 2-100 µg, or about 4-40 µg. One of skill in the art will appreciate that the dose amount will depend to some extent on the size of the mammal to which the composition is being administered. Approximately 1-10 doses are administered to the individual at intervals ranging from once per week to once per month to once per year.

Adjuvant, if present, is usually in the range of 10-1000 µg, preferably 250-750 µg, about 500 µg, or about 25-75 µg or about 50 µg per vaccine dose.

The examples herein are meant to exemplify the various aspects of carrying out the invention and are not intended to limit the invention in any way.

EXAMPLES

Example 1

The protection of CLDC combined with a whole detergent-inactivated HSV-2 lysate (HVAC) was compared to the HVAC combined with MPL. In the initial efficacy experiment, 60 female out-bred Swiss Webster mice (12 mice/group) were divided as follows: Group 1: no HVAC/no adjuvant; Group 2: HVAC alone; Group 3: HVAC+CLDC; Group 4: HVAC+MPL; and Group 5: CLDC alone. HSV specific antibodies were detectable after one immunization of HVAC alone or HVAC+CLDC or HVAC+MPL. Administration of CLDC enhanced the levels of detectable HSV-specific antibodies in the serum compared to mice that were immunized with HVAC+MPL (1.8-fold higher levels) or the HVAC alone (3.1-fold higher levels) after the first dose, showing that CLDC stimulates antigen-specific antibody production. Following the second immunization, the levels of HSV specific antibodies remained highest in the HVAC+CLDC group (2195 ng/ml) compared to HVAC alone (1503 ng/ml, $P<0.001$) or the HVAC+MPL (1758 ng/ml, $P=0.012$) (data not shown).

Figure 2:
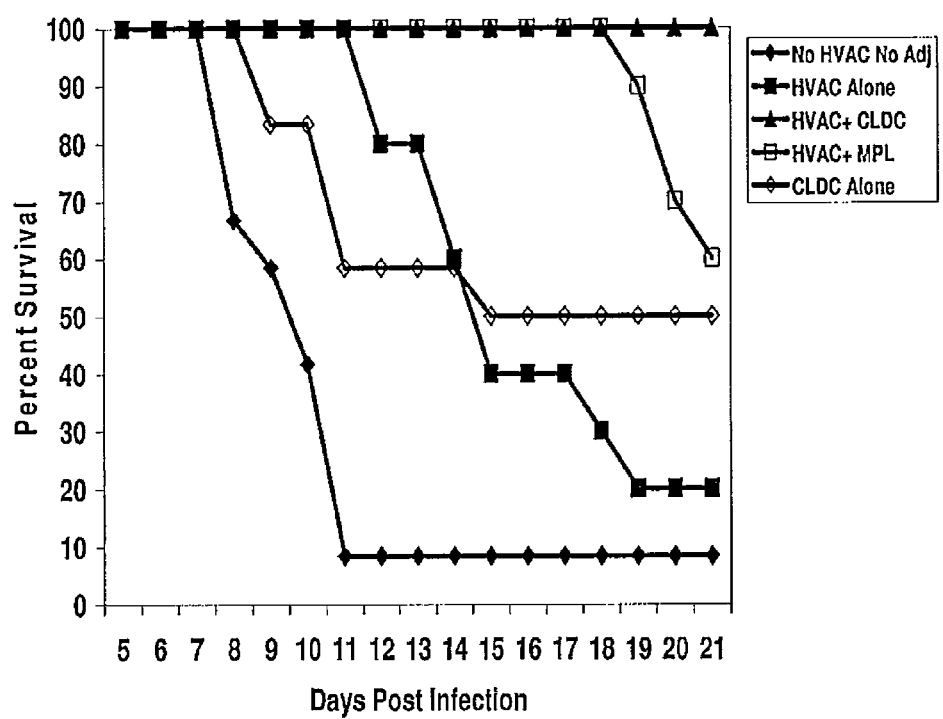
FIG. 2 provides a plot of survival to day 21 following intravaginal HSV-2 challenge of the mice analyzed in FIG. 1.

Animals were also assessed daily to monitor the development of symptomatic HSV infection. As seen in FIG. 1, 100% of the mice that received no vaccine, 83% of the mice that received CLDC alone, and 80% of the mice that received HVAC alone, developed local disease. In contrast, only 40% of the mice that received HVAC+MPL ($P=0.170$ vs. vaccine alone) and 18% of the mice receiving HVAC+CLDC ($P=0.009$ vs. vaccine alone) developed disease. Similarly as seen in FIG. 2, mice that received no vaccine, CLDC alone, or vaccine alone, were not protected from death (8-50% survival by 21 days). The HVAC+MPL protected 60% of the mice ($P=0.170$ vs. vaccine alone) while 100% of the mice that were vaccinated with HVAC+CLDC were protected from death ($P<0.001$ vs. vaccine alone and $P=0.035$ vs. HVAC+MPL.

To further document the antiviral nature of the vaccinations, effects on vaginal viral replication were examined. Immunization with HVAC+CLDC significantly reduced the level of infectious virus in the vagina on all four days and eliminated viral shedding by day 4 in 10 of 11 animals (data not shown). Reductions in viral shedding in the HVAC+CLDC group compared to vaccine alone was significant on all days and when compared to the HVAC+MPL group, titers were significantly less on days 2 and 3.

Example 2

Figure 3:
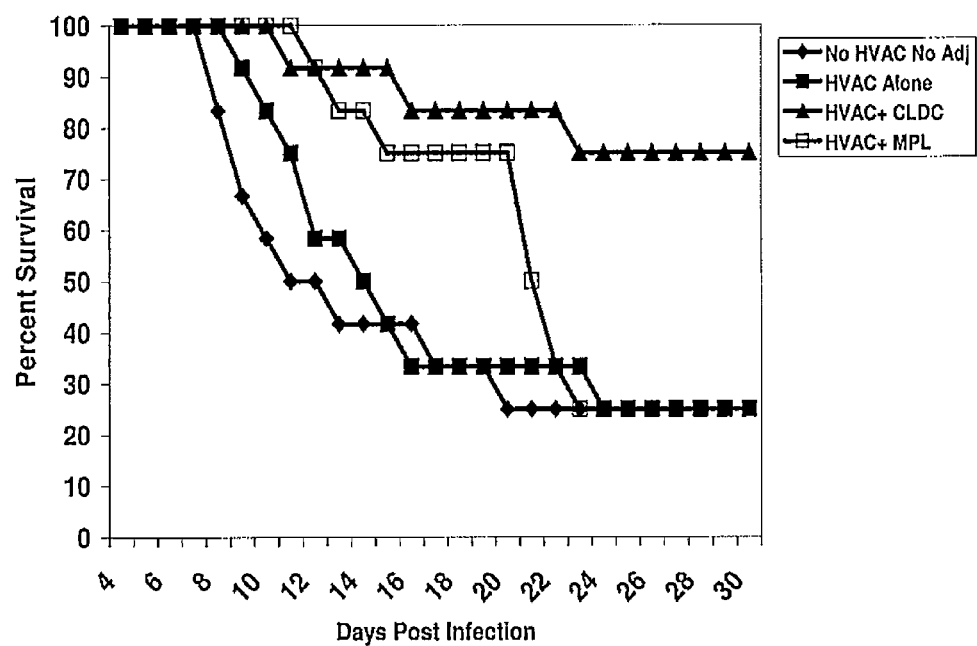
FIG. 3 provides a plot of survival to day 30 following intravaginal HSV-2 challenge, of mice (12 mice/group with four groups), which were vaccinated as follows: Group 1) no HVAC/no adjuvant; Group 2) HVAC alone; Group 3) HVAC+CLDC; and Group 4: HVAC+MPL.

A second study using 48 female out-bred Swiss Webster mice (n=12) was then performed to validate the first results and extend the observation to 30 days, as it appeared that animals in the HVAC+MPL vaccine group continued to die after day 21. In agreement with the results of the first study, mice vaccinated with the HVAC alone were more likely to develop local disease (75%) than animals vaccinated in combination with CLDC (25%, P=0.039 vs. HVAC alone). Thus, similar to the first study, HVAC+CLDC provided significantly better protection compared to HVAC+MPL (P=0.012). Significantly and as shown in FIG. 3, vaccination with HVAC+CLDC protected 75% of the mice from death out to 30 days after viral challenge whereas the HVAC+MPL vaccine only protected 25% of mice from death (P=0.039), and continued to die after 21 days. These results demonstrate that the CLDC adjuvant when combined with a whole inactivated HSV-2 lysate enhances protection in the mouse model of herpes infection.

Example 3

Figure 4:
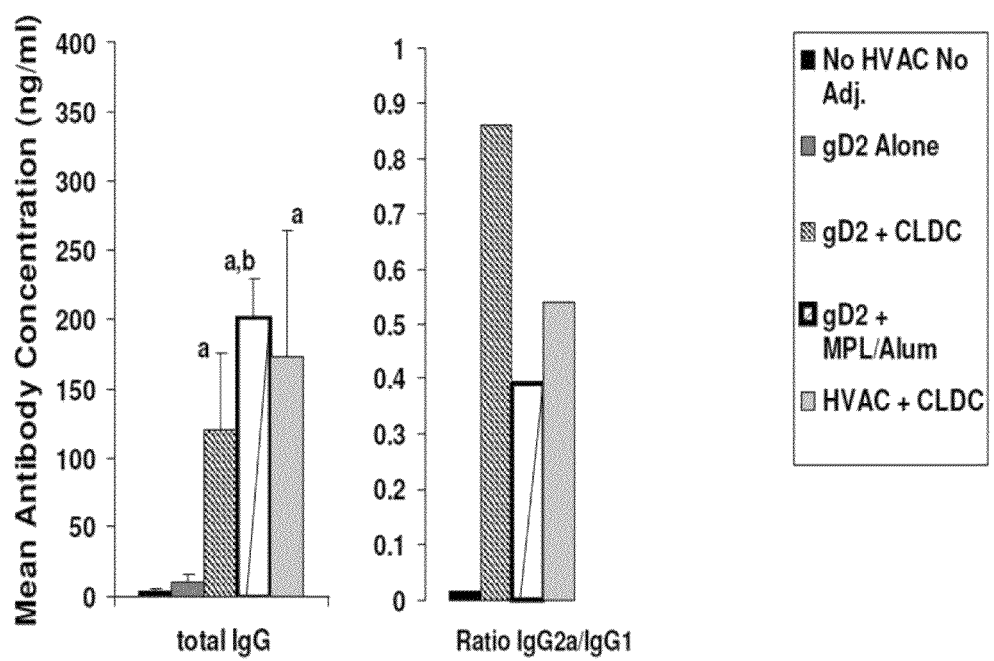
FIG. 4 shows plots of the antibody responses to gD2 vaccines with CLDC or MPL/alum (aluminium hydroxide). The mice were divided into five groups: Group 1) no HVAC/no adjuvant; Group 2) gD2 alone; Group 3) gD2+CLDC; Group 4) gD2+MPL/alum; and Group 5) HVAC+CLDC.

In this study, gD2 (full-length ectodomain) administered alone or with CLDC or MPL/alum was evaluated. In order to evaluate CLDC with a vaccine which more closely resembles the vaccine that previously showed some protection in clinical trials (Stanberry et al., N Engl J Med. 347(21):1652, 2002), and is being further evaluated in a large clinical trial, the antibody and T cell response in mice immunized with gD2 (full-length ectodomain) alone, gD2 (full-length ectodomain)+CLDC, and gD2 (full-length ectodomain)+MPL/alum were analyzed. In particular, animals were immunized twice and serum obtained 3 weeks after the second immunization. The amount of anti-HSV-1 IgG1 and IgG2a were measured by ELISA. As shown in FIG. 4, mice receiving gD2+CLDC, or gD2+MPL/alum produced considerably higher levels of anti-HSV antibody than gD2 alone (P<0.01) although antibody levels induced by MPL/alum were higher compared to CLDC (P=0.05). However, vaccination with gD2+CLDC resulted in a higher ratio of IgG2a to IgG1 (0.86) compared to the gD2+MPL/Alum group (0.39), indicating that the CLDC adjuvant is more effective than MPL/alum at promoting Th1 immunity.

Figure 5:
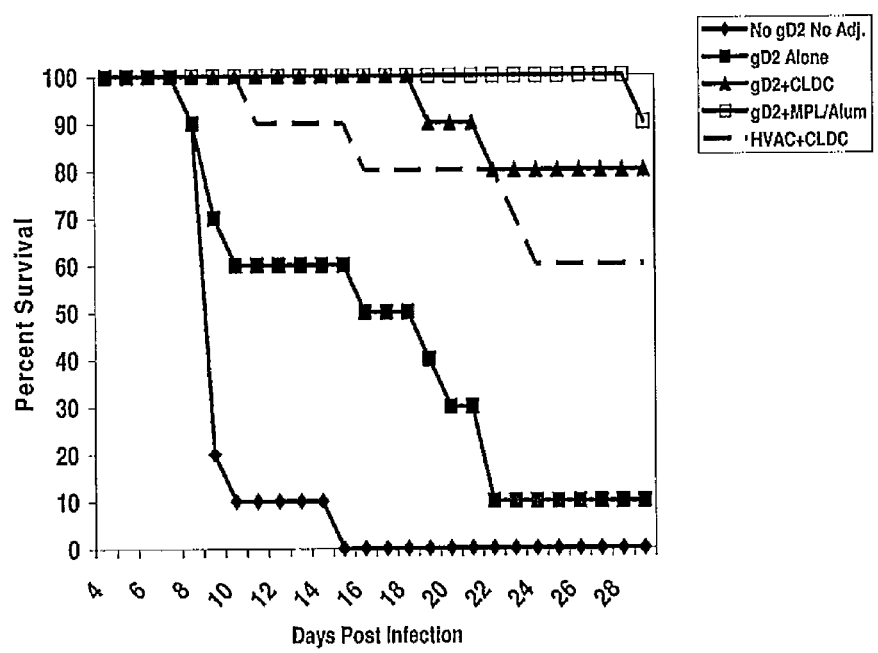
FIG. 5 provides a plot of survival to 30 days following intravaginal HSV-2 challenge of mice, vaccinated according to the following groups: Group 1) was no gD2/no adjuvant; Group 2) gD2 alone; Group 3) gD2+CLDC; Group 4) gD2+MPL/alum; and Group 5) HVAC+CLDC.

Vaccination with gD2 alone did not protect against disease or death, although death was delayed in mice receiving gD2 alone (mean day of death=16.0) compared to the untreated group (mean day of death=10.6, P=0.015). As seen in FIG. 5, mice receiving gD2+CLDC or gD2+MPL/alum were significantly protected from disease (40% in each group) compared to mice receiving the gD2 antigen alone (100% with disease, (P=0.011). Vaccination also decreased death in the adjuvant groups from 90% in the gD2 alone group to 20% and 10%, respectively, for CLDC (P=0.006 and MPL/alum, P=0.001) (data not shown). Further, vaccination with gD2+CLDC significantly reduced vaginal viral titers on days 1, 3, and 4 post-challenge compared to the untreated group (P<0.05) (data not shown). Similarly, mice receiving gD2+MPL/alum had significantly lower viral titers on days 1 and 4 compared to the untreated group (P<0.05). There were no statistically significant differences in vaginal viral titers between the gD2+CLDC and gD2+MPL/alum groups on any day. Of interest, the virus titers in the HVAC+CLDC group were significantly less than titers to gD2+CLDC at 1 day after infection, suggesting additional HSV antigens may contribute to protection.

Example 4

Figure 6:
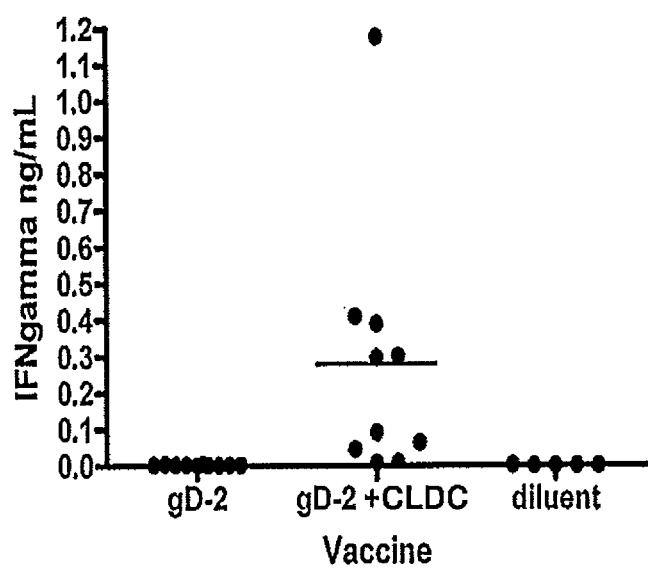
FIG. 6 shows a plot of the interferon-gamma (IFN-γ) response of splenocytes to gD2 vaccination. The mice were vaccinated with gD2 alone, gD2+CLDC, or diluent.

To further evaluate the mechanism of adjuvant activity, mice were vaccinated with gD2 (full-length ectodomain) alone or with gD2 (full-length ectodomain)+CLDC. Splenocytes from mice vaccinated with gD2 alone, gD2+CLDC, or control splenocytes were re-stimulated with gD2 antigen and supernatants were collected after 96 hours and assayed by ELISA for murine IFN-γ. Higher levels of total anti-gD2 IgG antibody was detected in the group immunized with gD2+CLDC compared to gD2 alone (P<0.01) (data not shown). In addition, the ratio of IgG2a to IgG1 was increased in the gD2+CLDC group (data not shown). As shown in FIG. 6, splenocytes from mice vaccinated with gD2+CLDC showed a significant production of IFN-γ when re-stimulated with gD2 antigen (P<0.05). In agreement with previously published studies, IFN-γ production in response to gD2 was primarily produced by CD4+ T cells, since depletion of the CD4+ T cell population resulted in a significantly lower level of IFN-γ (BenMohamed L, Bertrand G, McNamara C D, Gras-Masse H, Hammer J, Wechsler S L, and A B Nesburn. 2003. Identification of novel immunodominant CD4+ Th1-type T cell peptide epitopes from herpes simplex glycoprotein D that confer protective immunity. J. Virol. 77: 9463, Bettahi I, Zhang X, Afifi R E, and L BenMohamed. 2006. Protective immunity to genital herpes simplex virus type 1 and type 2 provided by self-adjuvanting lipopeptides that drive dendritic cell maturation and elicit a polarized Th1 immune response. Viral Immunol. 19(2):220.). In contrast, $CD8^+$ depleted splenocytes produced similar levels of IFN-γ as shown in FIG. 6 (data not shown).

Thus, gD2+CLDC vaccine promoted a superior Th1 antibody and T cell response in mice and that it was at least equivalent to gD2+MPL in protecting mice from HSV-2 infection.

Example 5

Because the guinea pig model also allows evaluation of the severity of acute disease, clinical recurrences, recurrent vaginal shedding and latent virus levels in the dorsal root ganglia, it is considered by many the small animal of choice for evaluation of vaccines. Therefore, the effects of vaccination with gD2 (full-length ectodomain)+CLDC were compared to gD2 (full-length ectodomain)+MPL/alum in the guinea pig model of genital herpes. The gD2+MPL/alum mimics the vaccine that was recently evaluated in two large clinical trials and is currently being further evaluated in a third clinical trial.

To begin the studies, sixty guinea pigs were randomized into five groups (N=12/group): Group 1: no vaccine; Group 2: CLDC alone; Group 3: gD2 alone: Group 4: gD2+CLDC; and Group 5: gD2+MPL/alum. Animals were immunized on days 49 and 21 days prior to viral inoculation. Each dose was administered by subcutaneous injection at five separate sites on the dorsum. One day before viral challenge, animals were bled by toenail clip and the serum stored at −20° C. The studies found, specific antibody to gD2 was increased by the combination of gD2 with both the CLDC and MPL/alum adjuvants (data not shown).

Animals were inoculated intravaginally with $5 \times 10^5$ pfu HSV-2, strain MS similar to previous studies (Bernstein D I, Harrison C J, Jenski L J, Myers M G, and L R Stanberry. 1991. Cell-mediated immunologic responses and recurrent genital herpes in the guinea pig: effects of glycoprotein immunotherapy. J. Immunol. 146:3571.). Swab samples of cervicovaginal secretions were collected on 1, 2, 4, 6, 8 and 10 days post infection (dpi) and stored frozen (−70° C.) until assayed for virus titers by plaque assay. Guinea pigs were evaluated daily and primary genital skin disease was quantified using a lesion score-scale ranging from 0, representing no disease, to 4, representing severe vesiculoulcerative skin disease of the perineum. Following recovery from primary infection, animals were examined daily from 21-63 dpi for evidence of spontaneous recurrent herpetic lesions. The number of lesion days (days on which a recurrent lesion was observed on the perineum) was used as a measure of the frequency of recurrent disease. Vaginal swabs also were obtained every three days from days 21-63 to evaluate for recurrent virus shedding. Swabs were stored frozen (−70° C.) until they were processed for PCR analysis to determine the frequency and magnitude of viral shedding into the genital tract. At the end of the study, the guinea pigs were sacrificed, and the DRGs were harvested aseptically. DRGs were stored frozen (−80° C.) until DNA was extracted by PCR for determination of the magnitude of latent virus infection.

Figure 7:
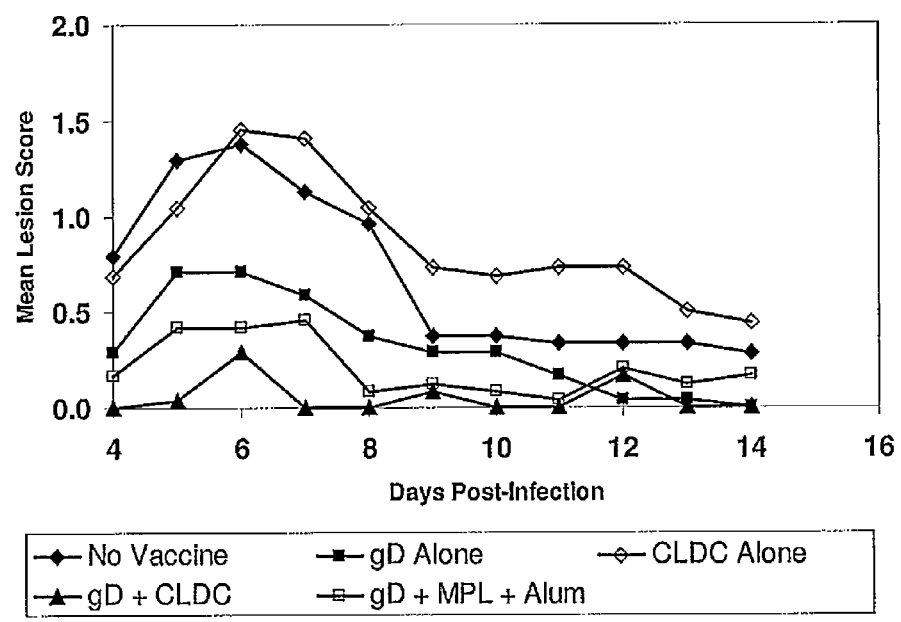
FIG. 7 provides the clinical outcome of primary lesions in guinea pigs following intravaginal HSV-2 challenge. Sixty guinea pigs were randomized into five groups (12 guinea pigs/group): Group 1) no vaccine; Group 2) CLDC alone; Group 3) gD2 alone; Group 4) gD2+CLDC; and Group 5) gD2+MPL/alum.

As shown in FIG. 7, following vaccination at 21 and 49 days prior to virus challenge, the gD2+CLDC vaccine significantly decreased the severity of genital disease compared to vaccine alone (P<0.001) and compared to the gD2+MPL/alum vaccine (P=0.060). The only animals that did not develop disease were in the groups receiving gD2+CLDC (5 animals or 42%) and the group receiving gD2+MPL/alum (2 animals or 17%).

Figure 8:
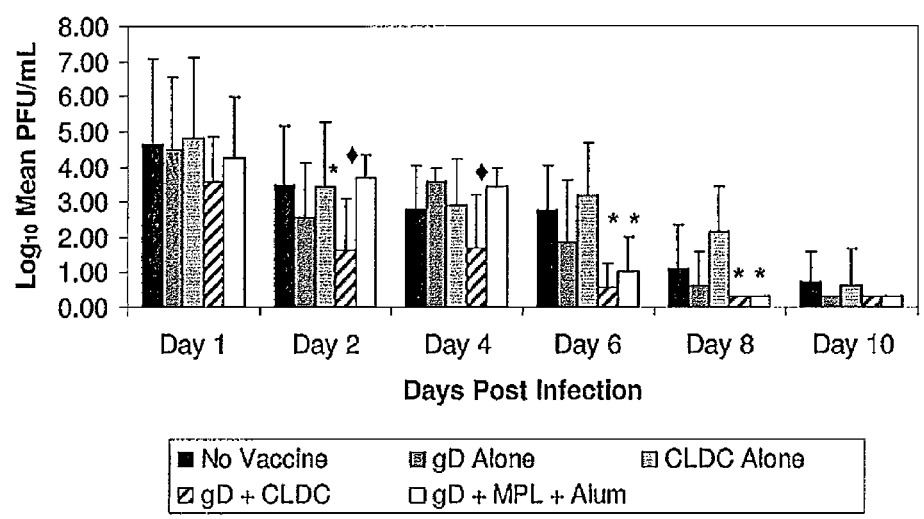
FIG. 8 shows a plot of the primary vaginal virus replication following HSV-2 challenge. Vaginal swabs were collected from the same five groups of guinea pigs as those in FIG. 7. Virus titers were determined by plaque assay.

As shown in FIG. 8, only vaccination with an adjuvant significantly decreased the amount of virus shed during the acute disease. On 4 and 6 dpi, the amount of virus shed in the group receiving gD2+CLDC was significantly less than the group receiving gD2 alone and likewise, the gD2+CLDC shed significantly less virus on 2 and 4 dpi than the group receiving gD2+MPL/alum (P<0.05).

Figure 9:
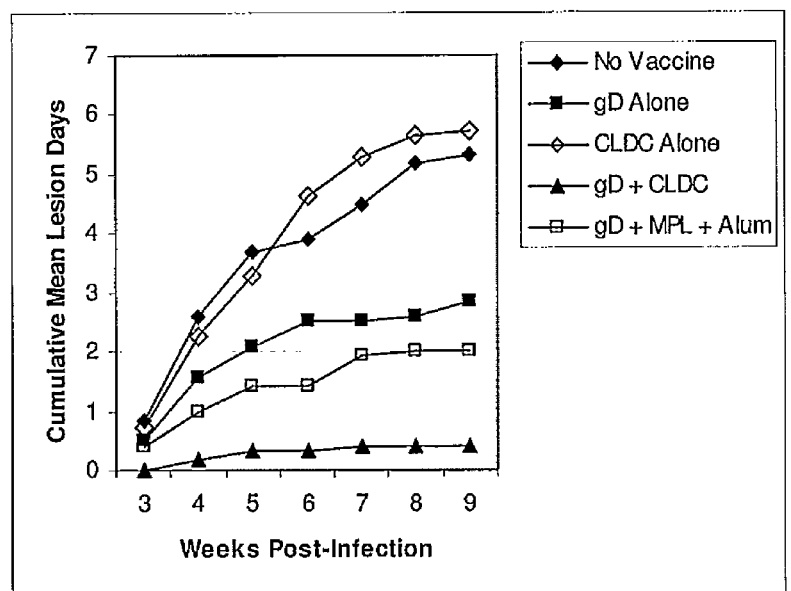
FIG. 9 shows a plot of the effects of vaccination on subsequent recurrent disease from 3 to 9 weeks after challenge of the five groups of guinea pigs from FIG. 8.

The effects of vaccination on subsequent recurrent disease are shown in FIG. 9. The data are depicted as cumulative mean lesion days from 3 to 9 weeks after challenge. Most importantly, the number of days with recurrences was significantly less in the gD2+CLDC group (0.4±1.4) compared to gD2 alone (2.8±3.6) or gD2+MPL/alum group (2.0±2.4). P<0.0001 for gD2+CLDC versus no vaccine; P<0.008 for gD2+MPL/alum versus no vaccine.

Figure 10:
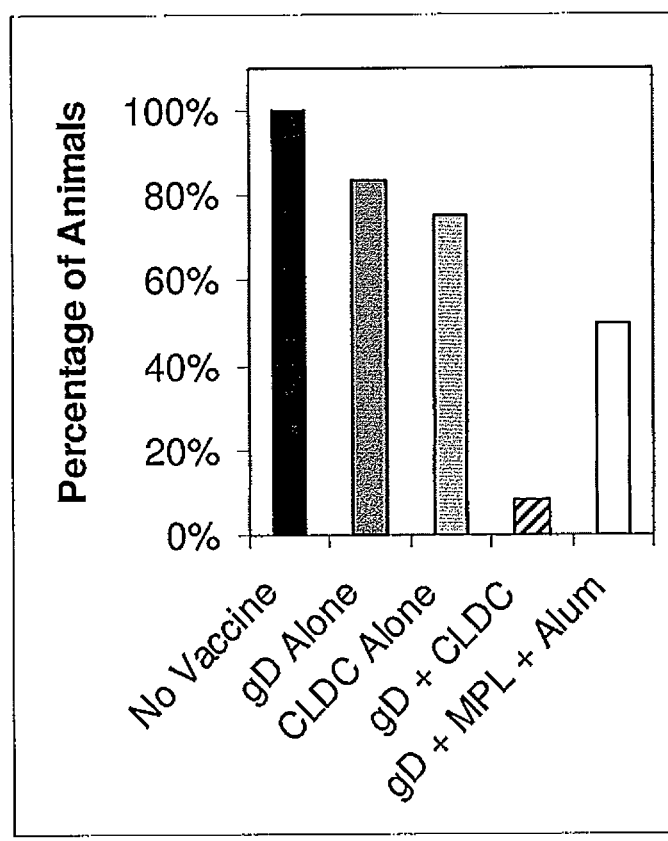
FIG. 10 provides a plot of the percentage of guinea pigs in each of the indicated vaccination group with subsequent recurrent lesions.
Figure 11:
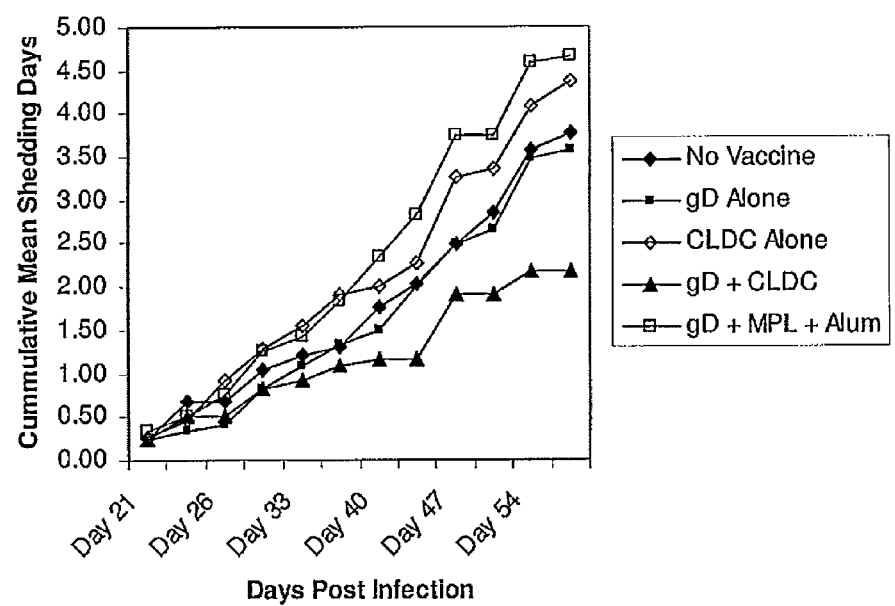
FIG. 11 shows a plot of the mean number of days with recurrent lesions for each of the indicated vaccination groups of guinea pigs.
Figure 12:
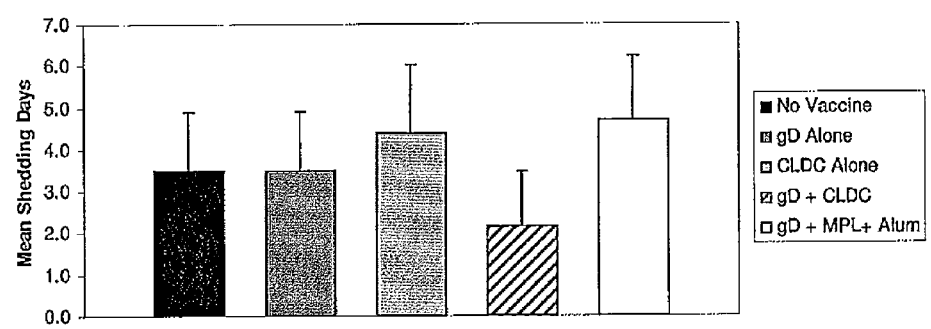
FIG. 12 provides a plot of the number of animals that shed virus is each of the indicated vaccination groups. Mean shedding days are mean number of days in which viral DNA was detected from day 21 to day 63 following HSV-2 challenge.

As shown in FIG. 10, vaccination with gD2+CLDC, or gD2+MPL/alum significantly decreased the number of animals developing recurrences compared to the gD2 alone group (P<0.001 and P<0.07, respectively). The gD2+CLDC also had significantly fewer animals with subsequent recurrent disease compared to the gD2 alone group (P<0.001), whereas the gD2+MPL/alum group was not significantly different. Notably, only one out of 12 animals (8%) in the gD2+CLDC group developed subsequent recurrent lesions compared to six out of 12 (50%) for the gD2+MPL/alum group (p=0.07). Similarly, the mean number of days with recurrent lesions was decreased by immunization, as shown in FIG. 11. As shown in FIG. 12, the number of animals that shed virus after the acute disease had resolved was not significantly different between groups. However, only vaccination with gD2+CLDC reduced the number of days with recurrent virus shedding to 2.2±1.3 days in the gD2+CLDC compared to 3.5±1.4 days in the gD2 alone group and 4.7±1.6 days in gD2+MPL/alum (P<0.05 for each comparison to CLDC).

Example 6

Various HSV-2 subunit vaccines were introduced into guinea pigs (12 guinea pigs/group) with the following groups: 1) no vaccine (10% sucrose only); 2) gD-FL (full length ectodomain of gD2, amino acids 1-306)+CLDC; 3) gD-T (truncated gD2 amino acids 1-285)+CLDC; 4) gD-T+gB2t (amino acids 31-726)+gH2t/gL2 (amino acids 21-802)+CLDC; and 5) gB2+gH2/gL2)+CLDC. The guinea pigs were immunized subcutaneously twice at three-week intervals, and challenged intravaginally three weeks later with $1 \times 10^6$ pfu (total) HSV-2 (MS strain). All of the vaccinated groups had significantly reduced acute lesions and virus titers at 2 and 5 dpi compared to the no vaccine group (p<0.002); whereas no significant differences were observed between the vaccinated groups.

Figure 14:
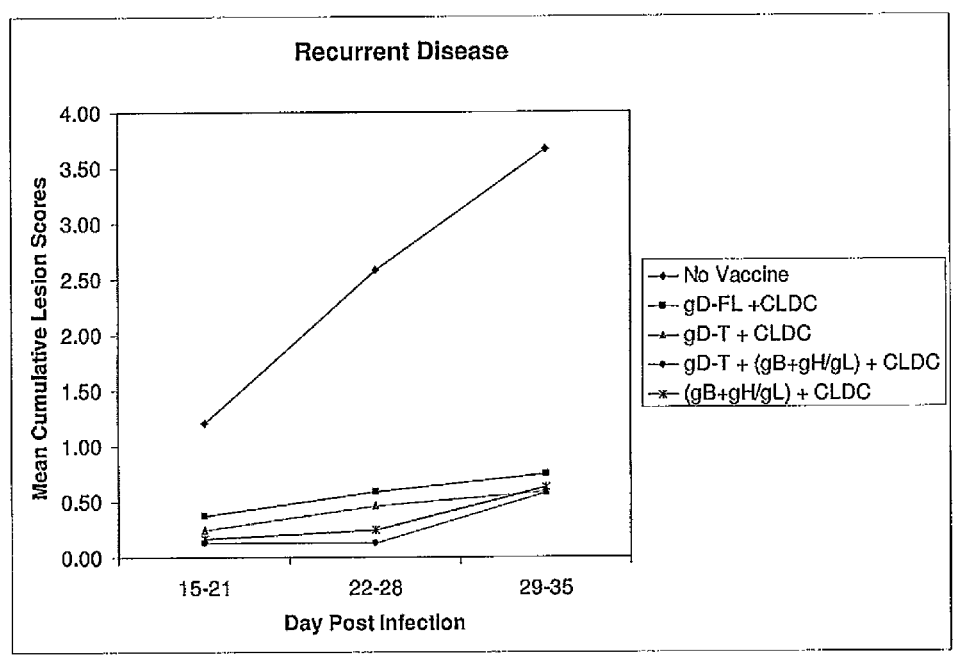
FIG. 14 shows a plot of the recurrent mean cumulative lesion scores for the indicated vaccination groups.
Figure 15:
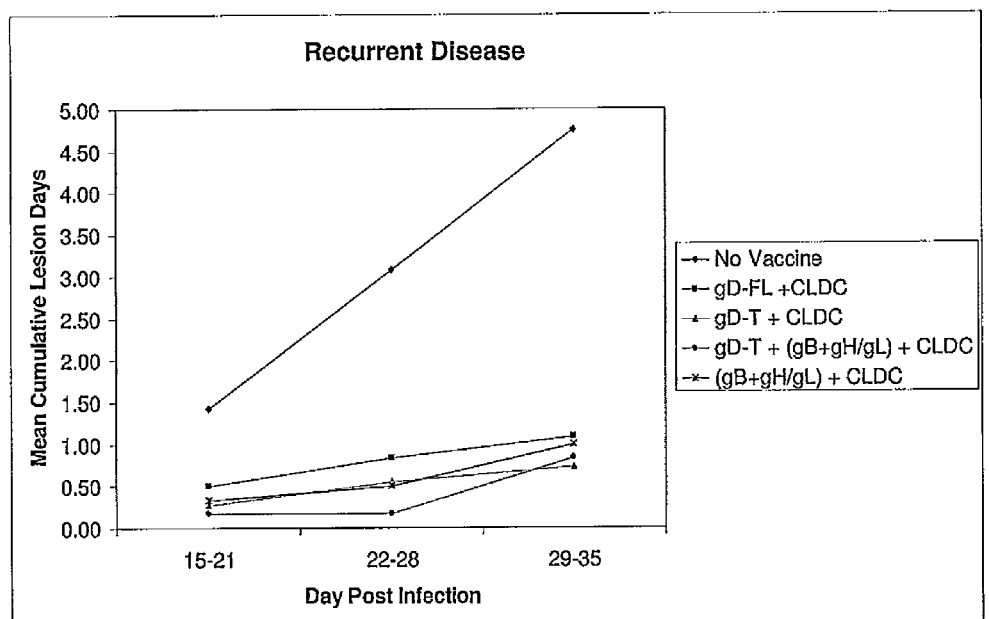
FIG. 15 shows a plot of the mean cumulative lesion days for the indicated vaccination groups.

Vaccination with any of the vaccines significantly reduced recurrent HSV-2 disease (p<0.002) compared to the no vaccine group. For all of the vaccination groups, recurrent mean lesion scores (~1.0 versus 7.5) and recurrent mean lesion days (~1 day versus 9 days) were significantly reduced compared to the no vaccine group (FIGS. 14-15). Swab samples were collected on 1, 2, 5 and 8 days (dpi) and assayed for virus titers. The animals were scored for primary disease for days 3-14 and for recurrent disease for days 15-60.

Figure 13:
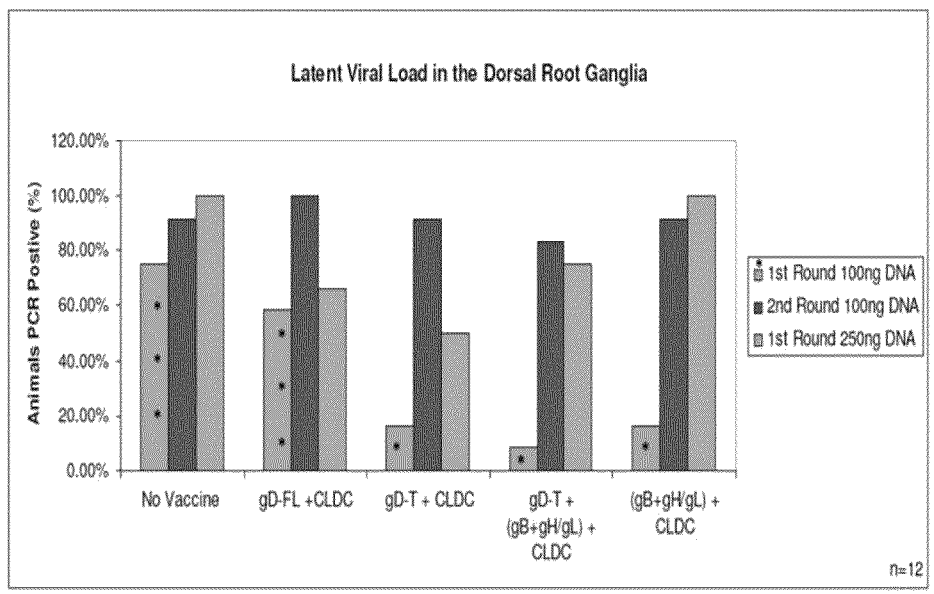
FIG. 13 shows a plot of the latent viral DNA in the dorsal root ganglia (DRG) after the indicated rounds of PCR for five groups of guinea pigs (12 guinea pigs/group): Group 1) no vaccine; Group 2) gD2-FL+CLDC; Group 3) gD2T+CLDC; Group 4) gD2T+gB2T+gH2/gL2+CLDC and Group 5) gB2+gH2/gL2+CLDC

PCR analysis of latent viral DNA in the DRG after 63 dpi demonstrated a significant difference (p<0.01) following first round PCR Groups 3, 4, and 5 compared to Group 1, while Group 1 was not significantly different. Following nested PCR, all groups had 80% of the DRGs positive for HSV-2 DNA, suggesting subtle differences between latent viral load among the vaccination groups. Data shown below and in FIG. 13.

| Groups | # Pos 1st 100 ng | | # Pos 2nd 100 ng | | # Pos 250 ng | |
|---|---|---|---|---|---|---|
| No Vaccine | 9 | 75.00% | 11 | 91.67% | 12 | 100.00% |
| gD-FL + CLDC | 7 | 58.33% | 12 | 100.00% | 8 | 66.67% |
| gD-T + CLDC | 2 | 16.67% | 11 | 91.67% | 6 | 50.00% |
| gD-T + (gB + gH/gL) + CLDC | 1 | 8.33% | 10 | 83.33% | 9 | 75.00% |
| (gB + gH/gL) + CLDC | 2 | 16.67% | 11 | 91.67% | 12 | 100.00% |

Example 7

Various preparations of cationic liposome delivery vehicles, such as JVRS-100, are described in U.S. Pat. No. 6,693,086 and as follows. For example, a cationic liposome consisting of DOTAP (1,2 dioleoyl-3-trimethylammonium-propane) and cholesterol was mixed in a 1:1 molar ratio, dried down in round bottom tubes, and then rehydrated in 5% dextrose solution (D5W) by heating at 50° C. for 6 hours, as described previously (Solodin et al., 1995, *Biochemistry*, 34:13537-13544). This procedure results in the formation of liposomes that consists of multilamellar vesicles (MLV), which provide optimal transfection efficiency when compared to small unilamellar vesicles (SUV). The production of MLVs and related "extruded lipids" is also described in Liu et al., 1997, *Nature Biotech.*, 15:167-173; and Templeton et al., 1997, *Nature Biotech.*, 15:647-652.

Example 8

Sf9 cells are grown to a density of $4 \times 10^6$ cells per mL in a Celligen bioreactor or Spinner vessel and infected with a recombinant virus at an MOI of 4. The cell supernatant is separated from cells when the cell viability drops to 70 percent (typically, 72 hours post-infection). Proteins are purified by one or two different methods:

1. Immunoaffinity chromatography. As examples, gD2 (306t) and gD2(285t) are purified from the culture supernatant by immunoaffinity chromatography using the gD type-common monoclonal antibody, DL6, a non-neutralizing antibody that recognizes a continuous epitope at 272-279. The procedure is identical to that used for gD1(306t) (Sisk, W. P., J. D. Bradley, et al. (1994). "High-level expression and purification of secreted forms of herpes simplex virus type 1 glycoprotein gD synthesized by baculovirus-infected insect cells." J. Virol. 68: 766-775.). After washing with a buffer consisting of 10 mM Tris.HCl, pH 7.2, and 500 mM NaCl, bound gD is eluted from the column with 3M KSCN. The recovered protein is dialyzed against PBS and concentrated prior to storage at −80° C. A typical recovery of purified gD2 (306t) is 5-10 mg/L of supernatant fluid. DL16, a trimer specific antibody, was used to purify gB 1 but it binds gB2 poorly.

2. Nickel affinity chelate chromatography. Some gB and gD constructs were prepared using nickel affinity chelate chromatography. To utilize this procedure, the protein must have an accessible 6-His tag (SEQ ID NO:17). Briefly, the supernatant fluid from infected Sf9 cells was concentrated, dialyzed and the his-tagged protein was adsorbed onto nickel beads, and washed with a buffer to get rid of contaminating proteins that adhere to the beads. For some proteins, the wash step might just require elevated salt and in other cases, such as for gH/gL, a low concentration of imidazole is needed. This step gets rid of the contaminants, but somewhat lowers the yield. The protein was eluted with imidazole, dialyzed, concentrated and stored at about −80° C. About 1-2 mg of gH/gL2 was obtained per liter of media.

Example 9

DNA encoding amino acid residues 1-306 (not including the signal sequence) of gD2 from the HSV-2 strain 333 was modified with sequences for a 6-His tag (SEQ ID NO:17) (after residue 306) was cloned into the baculovirus transfer vector pVT-Bac (Tessier, D. et al., Gene 98: 177-183, 1991). It was cloned in frame with the DNA sequence of the honey bee melittin signal peptide. The resulting plasmid is pAN243.

Using the same pVT-Bac vector, a further gD2 truncated form (gD2t (285)) was cloned. The resulting plasmid is pYZ343. This construct also has a His tag after residue 285. Also cloned was a "His-less" version of gD2t (285), for which the plasmid is pYZ342.

DNA encoding amino acid residues 31-726 of the glycoprotein gB2 from HSV-2 strain 333 was inserted into the pVT-Bac vector in frame with the melittin signal sequence (pCW289).

DNA encoding amino acid residues (21-802) of glycoprotein gH2 with a 6-His tag (SEQ ID NO:17) and full length glycoprotein gL2 (which lacks a transmembrane domain or cytoplasmic tail) from HSV-2 strain 333 were cloned into the vector pFastBacDual (pTC605). This vector allows one to clone two genes in frame with two different promoters. The proteins were cloned to include their native signal sequences.

A mammalian cell line was constructed, which secretes a soluble gH/gL complex, consisting of gH truncated at amino acid residue 792 (gH-1t792) and full length gL, both from HSV-1. Purified gH-1t792/gL1 reacted with gH/gL specific monoclonal antibodies, including LP11, indicating that the complex retained its proper antigenic structure. Polyclonal antibodies to the complex did block entry and exhibited high titers of complement-independent neutralizing activity against HSV-1, and showed limited cross-neutralization of HSV-2.

Mice were immunized with the complex. Using a zosteriform model of infection, mice were challenged with HSV-1. Mice immunized with either gD or gH-1t792/gL1 had reduced primary lesions and exhibited no secondary zosteriform lesions and survived virus challenge.

The gH-1t792/gL1 and gH-2t792/gL2 forms were prepared in the baculovirus expressions and then mice were immunized with the two sets of proteins. Both sets of sera neutralized their forms of the virus, but there was no cross-reactivity of gH1/gL1 to HSV-2 or gH2/gL2 to HSV-1.

Also prepared were complexes of gD2 with gH2/gL2 wherein the gD2 full length ectodomain or the truncated form, gD-2t (285), were appended onto the N-terminus of gH2. The tripartite complex functioned in infection and in inducing cell-cell fusion. The gD-2t(285) has a much higher affinity for the receptor than the full-length ectodomain form.

Example 10

These studies tested the immunogenicity of single and multi-antigen HSV2 subunit vaccines in both mice and non-human primates (cynomolgus monkey). The addition of adjuvant, either MPLalum or JVRS-100 (a cationic lipid-DNA complex) was beneficial for protection from disease progression and death in a mouse HSV2 challenge model regardless of whether it was composed of subunit glycoprotein gD (e.g., gD2t) and/or cellular entry antigens gB, gH and gL. In both the mouse and non-human primate studies, adjuvant increased the antigen specific and neutralizing antibody titers as well as the frequencies of HSV2 specific $CD4^+$ and $CD8^+$ T cell responses as measured by Th1 cytokine production. Interestingly in the mouse study, the data showed an inverse relationship between immunogenicity and increased antigen dose. An advantageous effect of a combinatorial antigen vaccine was shown in the non-human primate study and in the mouse study, but the responses differed most notably in increased T cell responses in the monkey model.

Animals. Female Balb/c mice approximately 6-8 weeks were obtained from Harlan Laboratories (Indianapolis Ind.) and group housed meeting the requirements of the United States Department of Agriculture (USDA) and the Guide for the Care and Use of Laboratory Animals. Chinese origin cynomolgus monkeys (*Macaca fasicularis*) were supplied by Three Springs Scientific (Perkasie Pa.) and housed in accordance with the regulations of the American Association for Accreditation of Animal Care Standards (AAALAC). At the time of study entry all non-human primates had tested negative for Herpes B antibodies.

Vaccine preparation/administration. Vaccines were prepared within four hours of vaccination by mixing the relevant antigen and adjuvant components (Tables 1 and 3). The HSV2 antigens were prepared from insect cells infected with a recombinant baculovirus expressing either gD2, gD2t, gB or gH/gL as previously described (Willis S H et al., J. Virol. 72:5937-47, 1998). Monophosphoryl-lipid A (MPL) was purchased from Sigma-Aldrich Corp, St. Louis, Mo. and resuspended in 0.5% (v/v) triethanolamine in water. The MPL/Alum combination contained 2.5 μg MPL and 10 μg aluminum potassium sulfate (Sigma) for mouse studies or 50 μg MPL and 200 μg aluminum potassium sulfate for non-human primate studies. JVRS-100 (Juvaris BioTherapeutics, Inc., Burlingame, Calif.) was provided as a white, lyophilized powder manufactured from plasmid DNA complexed with liposomes. The lyophilized CLDC drug product was reconstituted in sterile water for injection. After reconstitution, the final drug product was a colloidal dispersion of 0.3 mg/mL DNA, 1.88 mg/mL DOTIM and 1.05 mg/mL cholesterol at pH 7 containing 1.4 mM Tris-HCl and 10% w/v lactose (Fairman J et al., Hum. Vaccin. 5(3):141-50, 2009). 2.5 µg or 50 µg DNA weights of JVRS-100 were used respectively for mouse and non human primate studies. An overview of the mouse and non-human primate vaccine regimens is shown in Tables 1 and 3. All vaccinations were intramuscular with a 3 week period between primary inoculation and booster inoculation.

HSV2 Challenge. Five out of ten mice per group were designated for HSV2 viral challenge. The designated animals were administered 2 mg DEPO-PROVERA depot medroxyprogesterone acetate at a dose volume of 0.1 mL/animal via subcutaneous injection in the upper dorsal region on study day 31. On study day 36 the same animals received a challenge dose of $5 \times LD_{50}$ HSV2 strain MS intravaginally at a dose volume of 104/animal. Vaginal HSV2 infection induced clinical scores were recorded at least once daily for 24 days following viral challenge. Clinical scores were based on a grading scale of 0-5. A score of zero indicated no clinical signs of disease; one, vaginal erythema; two, vaginal erythema and edema; three, vaginal herpetic lesions; four, severe vaginal ulceration and/or hind limb paralysis; and five, death.

Vaginal Viral Titers. Surviving animals from viral challenge had vaginal swabs collected on days 38, 40 and 42. Swabs were placed in 1 mL DMEM containing antibiotics, vortexed for 30 seconds in triplicate and divided into aliquots for storage at −70° C. until viral titer analysis. On the day prior to performing the assay, 6-well tissue culture plate were seeded with $3-3.5 \times 10^5$ Vero cells/2 mL DMEM low glucose media fortified with 10% fetal bovine serum (FBS) and 1× PenStrep. Plates were used when they reached 80-100% confluence at approximately 16-20 hours post seeding. Ten fold serial dilutions were prepared for each swab sample. Samples were tested at dilutions from zero to 10-5. Dilution volumes of 200 µl were applied to cells after media removal and allowed to infect for 90 to 150 minutes in a 37° C. incubator. Plates were overlaid with 4 mL of warmed media and returned to the 37° C. incubator for two days. The cells were stained with 30 µL 1% Neutral Red and incubated an additional 12 hours before counting plaque numbers for each dilution.

Serum HSV2 Neutralization Assay. Two-fold serial dilutions of heat-inactivated serum or plasma from 1:25 to 1:800 were mixed with an equal volume of virus containing approximately 100 PFU's and incubated at 37° C. for one hour. After removal of growth media, each serum-virus mixture was added to 80-90% confluent Vero cells. After a 90 minute 37° C. incubation plates were overlaid with EMEM containing 0.5% agarose, 5% FBS and 1× PenStrep. Plates were incubated for two days at 37° C. and then either stained with 1.5% Neutral Red for an additional 12 hours (mouse study) or fixed with ice-cold acetone (80% v/v in PBS) and stained with crystal violet (non human primate study). Plaques were counted and the end point serum neutralization titers were defined as the final serum dilution that produced a >50% reduction in the number of viral plaques as compared to wells on the same plate containing only virus.

HSV2 Antigen Specific ELISA. Antibody was measured by ELISA using HSV-2 glycoprotein as the solid phase. High binding plates were coated with 2004 of 0.5 mg/ml HSV2 antigen diluted in PBS and after washing, blocking with 1% BSA in PBS and washing again, 5-fold serial dilutions of serum or plasma were applied. Plates were incubated for a minimum of 2 hours before washing and adding HRP-conjugated anti-mouse IgG or anti-monkey IgG (Southern Biotechnology, Birmingham, Ala.) for detection. The plates were then developed by addition of TMB substrate (ThermoFisher Scientific, Rockford, Ill.). Stop solution (1M $H_2SO_4$) was then added and the absorbance measured at 450 nm and 570 nm. The reading at 570 nm was subtracted from the reading at 450 nm to correct for plate abnormalities and bubbles in the analyte solution. The resulting data for each sample was plotted to obtain a curve of the inverse of the dilution versus the $A_{450}$-$A_{570}$ measurement. The antibody titer was calculated as the midpoint of the curve or $EC_{50}$ calculation using Prism statistical software.

Flow cytometric measurement of HSV2-specific T-cell responses. Freshly isolated splenocytes or peripheral blood mononuclear cells (PBMC) were assayed for their ability to secrete IFNγ, TNFα or IL-2 during in vitro restimulation with HSV2 (strain G) virus. Briefly, cells were stimulated for six hours with virus (1 MOI) or medium alone. Brefeldin-A at 10 µg/mL was added to the culture for the final 4 hours of stimulation. After stimulation the cells were surface stained with fluorescently conjugated antibodies to CD3, CD4 and CD8. Subsequently the cells were washed and treated with Fixation/Permeabilization Solution(s) (eBioscience, SanDiego, Calif.). Permeabilized cells were stained with fluorescently conjugated antibodies to IFNγ, TNFα, and IL-2 washed and then fixed with 2% paraformaldehyde. The antibodies were used in the following panels: Mouse; CD3-FITC, CD4-Alexa 700, CD8-PerCP Cy5.5, IFNγ-PE Cy7, TNFα-APC, IL2-PE and Non Human Primate; CD3-Alexa 700, CD4-PerCP Cy5.5, CD8-PE Cy7, IFNγ-FITC, TNFα-PE, IL2-APC (BD Biosciences, San Jose, Calif.). One hundred thousand events were collected on the FACs Canto and the data analyzed with FACs Diva software.

Figure 16:
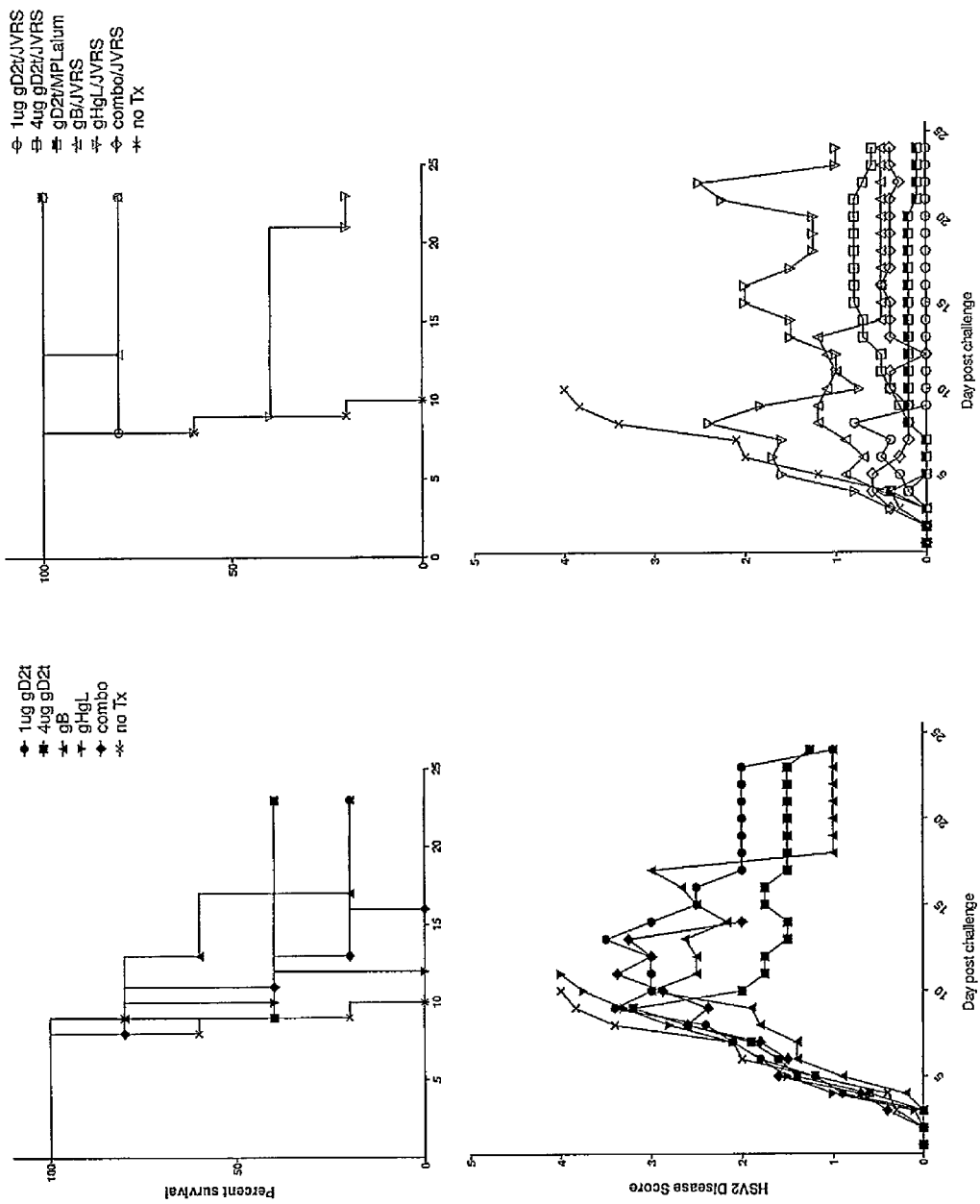
FIG. 16 shows plots of mouse percent survival and disease progression scores in groups of mice vaccinated with the indicated antigen(s) and with adjuvant (plots on the right side) or without adjuvant (plots on the left side). Animals were monitored and scored for survival and clinical disease signs after intravaginal challenge with HSV-2 virus.
Figure 17:
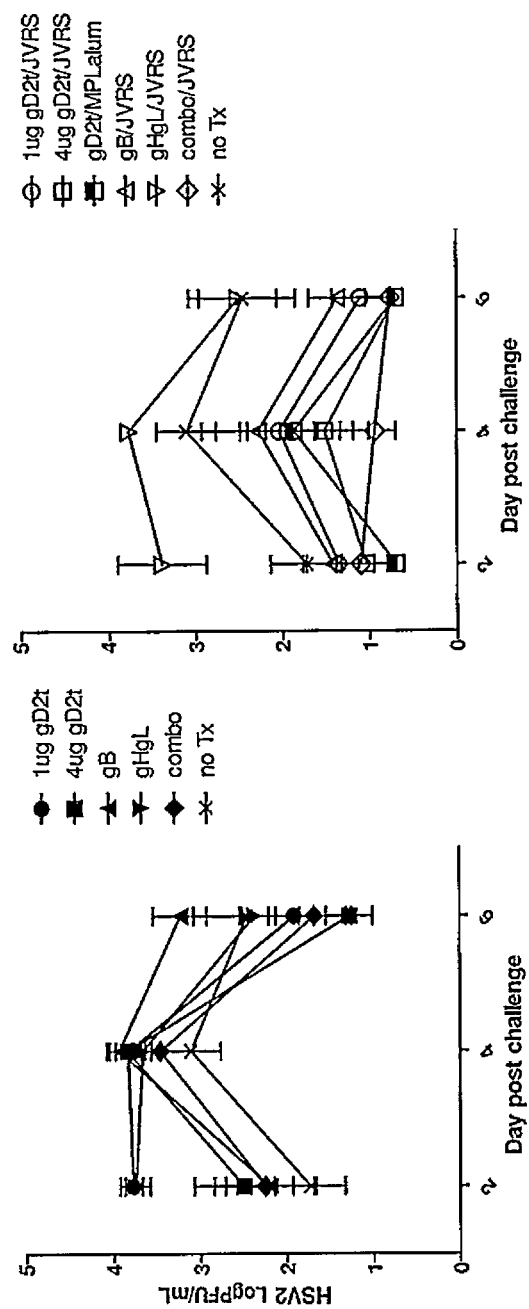
FIG. 17 shows plots of mouse vaginal viral titers of groups of mice vaccinated with the indicated antigen(s) and with adjuvant (plot on the right side) or without adjuvant (plots on the left side). Viral titer was assayed by culture of vaginal swabs for the presence of HSV-2 virus at 2, 4, and 6 days post viral challenge.

Mouse HSV2 viral challenge after vaccination. The effect of the various HSV-2 antigens alone and in combination with and without the addition of adjuvants MPLalum or JVRS-100 (cationic lipid DNA complex) was evaluated. Included were the cellular entry subunit glycoproteins gD in a truncated format (i.e., residues 1-285; termed "gD2t"), gB and gH/gL. Animals were vaccinated according to a two dose regimen (Table 1) prior to being subject to intravaginal challenge with HSV-2. Survival and disease score data (FIG. 16) underscore the requirement for inclusion of an adjuvant in vaccine formulations. None of the unadjuvanted groups had survival above forty percent whereas of the adjuvanted groups only gH/gL alone had survival below eighty percent. The disease scores patterns show more prolonged and severe symptoms in the unadjuvanted groups. Three groups that were one hundred percent protected from developing herpetic lesions were high dose gD2t plus JVRS-100, gD2t plus MPL/alum and triple combination gD2t, gB and gH/gL plus JVRS-100. Viral titers of vaginal swabs (FIG. 17) indicate only the triple combination plus JVRS-100 prevented viral replication after challenge. The challenge data show both the gD2t adjuvanted and combination adjuvanted groups had superior survival, viral titers and disease scores compared to the unadjuvanted gD2t and all gB, gH/gL groups.

Figure 18:
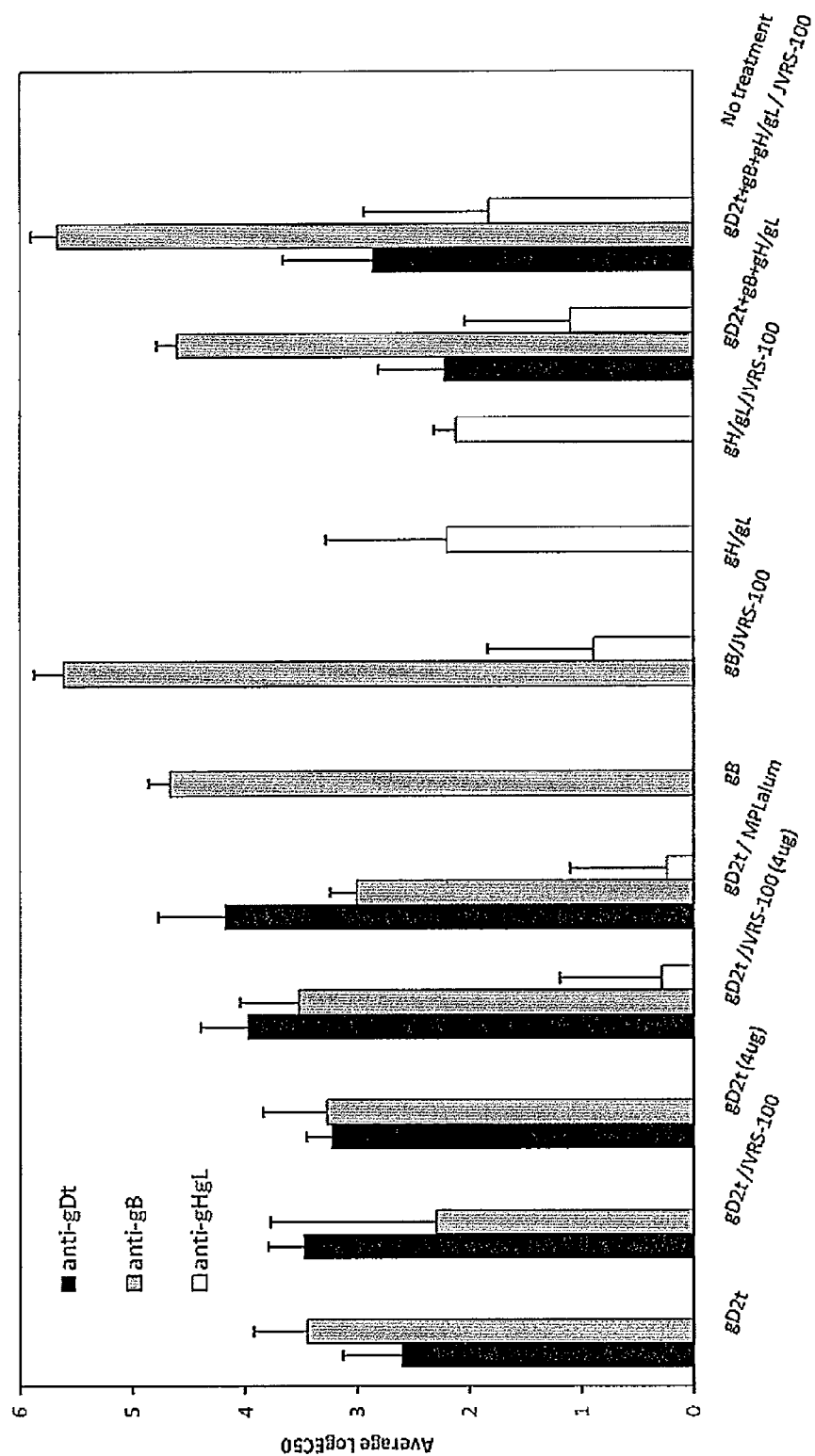
FIG. 18 shows a plot of mouse antigen specific antibody titers from groups of mice vaccinated with the indicated combinations of HSV-2 antigen and adjuvant. Antibody titers were assayed for antigen specific binding antibody. Average log $EC_{50}$, the log dilution at the midpoint of the binding curve, are shown for each group against gD (black bars), gB (grey bars), and gH/gL (white bars) antigens. Anti-gD antibodies cross reacted with gB but not vice versa.
Figure 19:
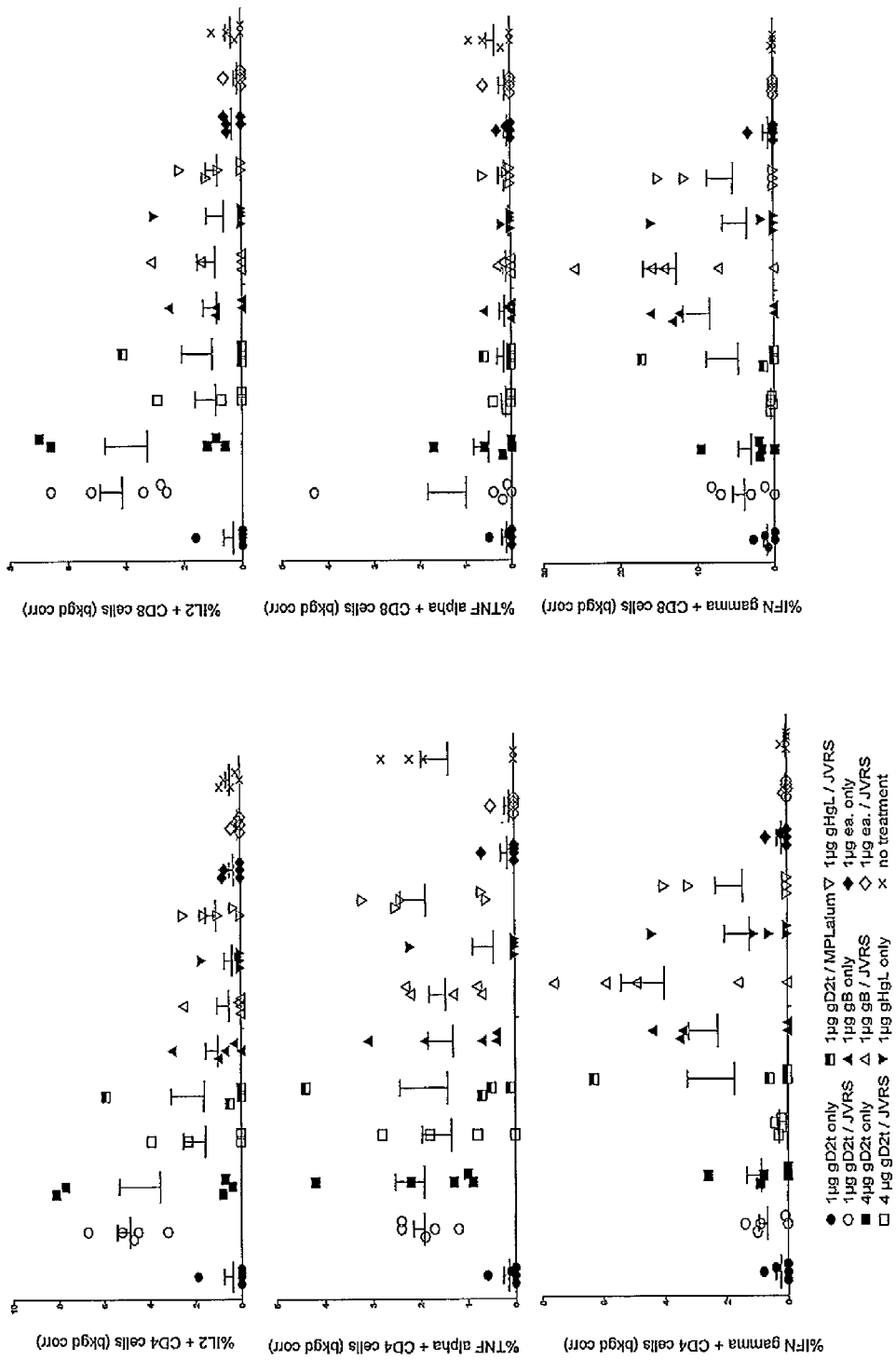
FIG. 19 shows the results of assays to detect T-cell specific responses to the vaccines in mice. The graphs represent the frequencies of IFNγ (bottom two plots), TNFα (middle two plots), and IL-2 (top two plots) cytokine producing CD4+ (left side plots) and CD8+ (right side plots) induced for each vaccination group.

Mouse humoral and cellular responses to vaccination. Adujvants enhanced the production of antigen specific antibodies by ten-fold, an average of one log (FIG. 18). The ELISA assay shows at least in vitro cross reactivity of anti-gD antibodies with gB but not vice versa. The antigen gB induced the highest antibody titers. Increasing the antigen dose four-fold from 1 µg to 4 µg overall resulted in a modest half-log antibody boost. The addition of multiple antigens did not appear to reduce the individual antibody titers to each specific antigen. Neutralizing antibody evaluation (Table 2) also showed gB to be the most potent antigen with 5 of 5 animals in the gB plus JVRS-100 and 4 of 5 animals in the combination plus JVRS-100 group containing gB, having detectable viral neutralizing titers. According to the cellular studies, adjuvant increased virus-specific CD4 and CD8 response measured by intracellular cytokine staining and flow cytometry (FIG. 19). It was determined that 1 μg gD2t plus adjuvant was better than 4 μg with adjuvant at eliciting effective T-cell responses.

Figure 20:
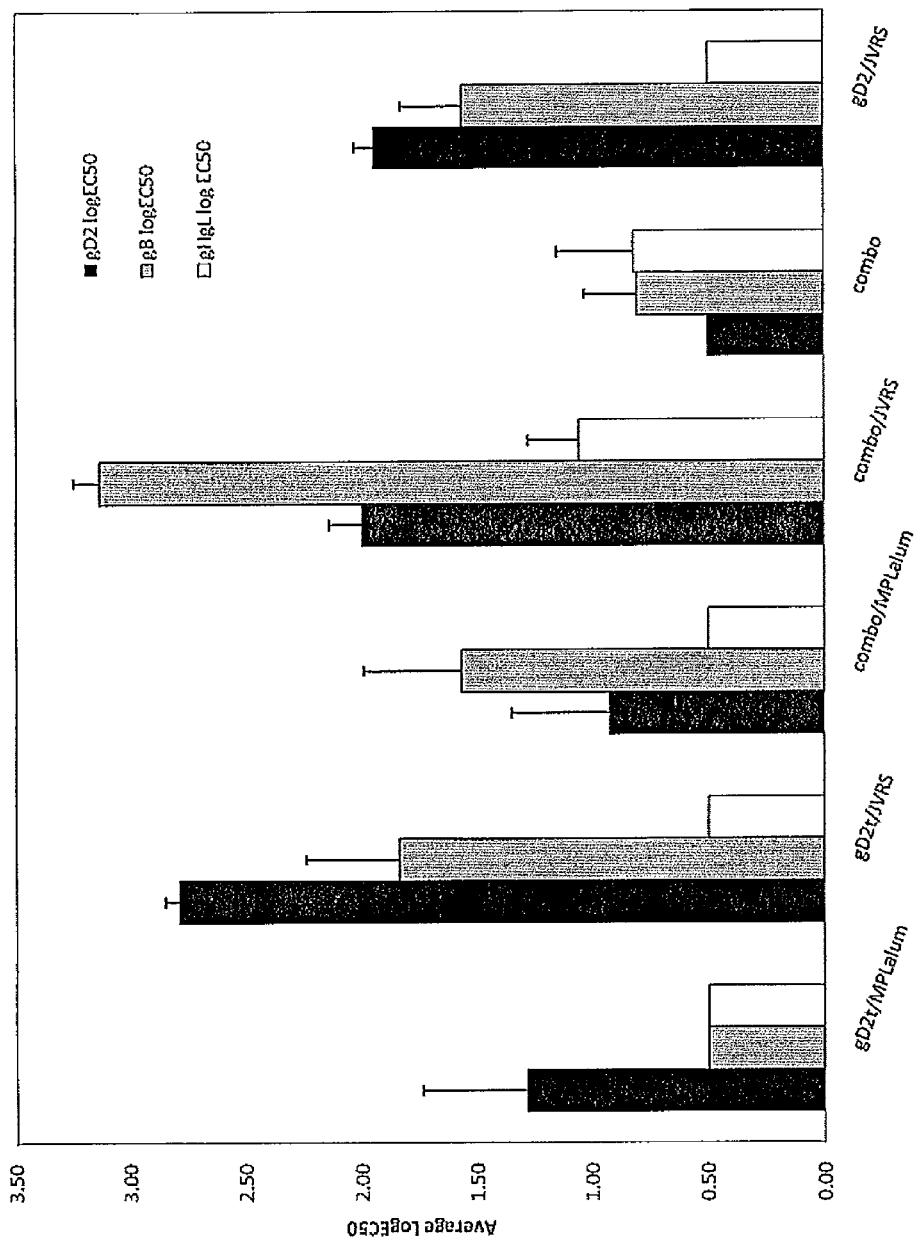
FIG. 20 shows a plot of antigen specific antibody titers in non-human primates. Groups of monkeys vaccinated with the indicated combinations of HSV-2 antigen and adjuvant were assayed for antigen specific binding antibody. Average log $EC_{50}$, the log dilution at the midpoint of the binding curve, are shown for each group against gD (black bars), gB (grey bars), and gH/gL (white bars) antigens. Anti-gD antibodies cross react with gB and gH/gL.
Figure 21:
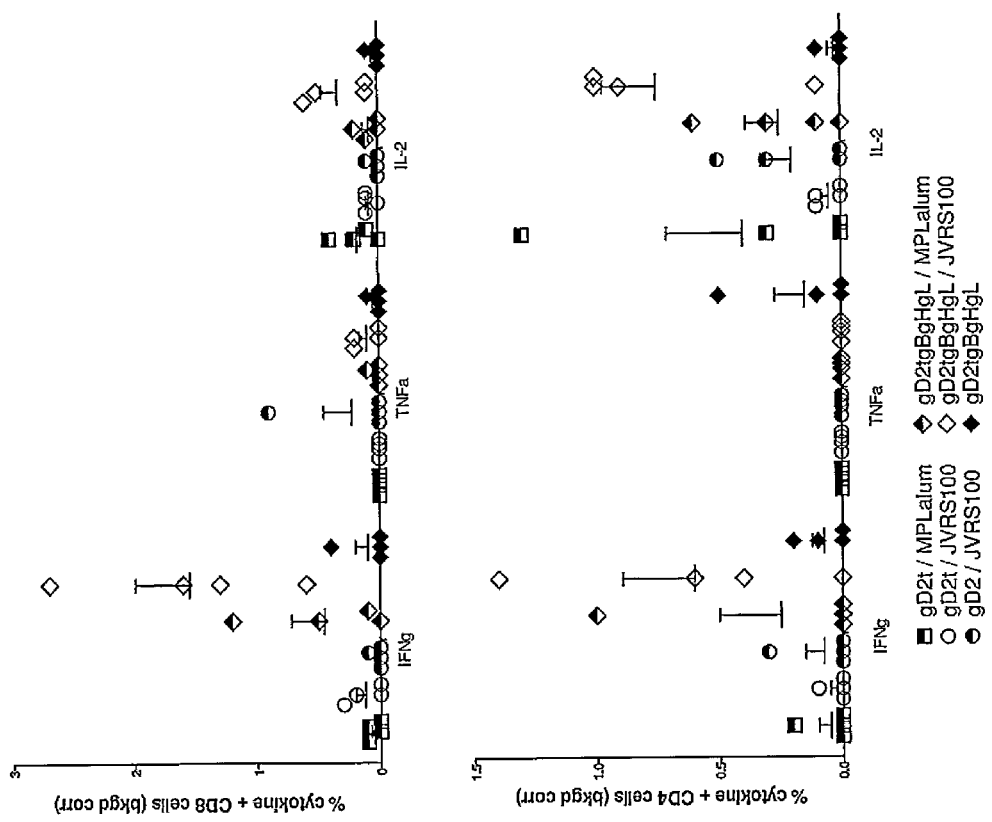
FIG. 21 shows the results of assays to detect HSV2 T cell specific responses in non-human primate. The graphs represent the frequencies of IFNγ, TNFα, and IL-2 cytokine producing CD4+ (bottom plot) and CD8+ (top plot) induced for each vaccination group.

Cynomolgus monkey humoral and cellular responses to vaccination. Animals were vaccinated in a prime boost regimen (Table 3) and their blood evaluated for immune response. Antigen specific antibody titers were overall lower to those seen in the mouse (FIG. 20). JVRS-100 was a more potent adjuvant than MPLalum with titers averaging twice as high in the ELISA assay. The form of gD truncated at amino acid residue 285 (gD2t) elicited higher titers than the gD form truncated at residue 306. Also, despite the apparent lesser production of antigen specific antibodies, a higher number of non-human primates raised detectable viral neutralizing antibody titers most notably in the JVRS-100 adjuvanted groups (Table 4). Interestingly, T-cell responses differed from the mouse as well in that the addition of multiple antigens enhanced Th1 cytokines production after in vitro stimulation (FIG. 21).

The present study addressed the hypothesis that the addition of JVRS-100, a cationic lipid DNA complex, and the combination of multiple cellular entry antigens would result in a more efficacious vaccine than antigens alone or the current human clinical candidate, gD2 plus MPLalum. The study showed that the triple combination of antigens and gD alone when adjuvanted with JVRS-100 were equivalent in the mouse challenge model except triplecombo+JVRS was the only vaccine to prevent viral replication in first 6 days of disease. JVRS-100 and MPLalum adjuvanted vaccines were equivalent in mouse challenge and antibody studies but JVRS-100 was superior to MPLalum adjuvanted vaccines in monkey antibody studies. Detectable neutralizing antibody was generated in the mouse model in response to vaccination with gB or the triple combination of antigen. The assays examining murine T-cell responses suggested that a larger dose was able to improve the T-cell response when administered alone but mice demonstrated an inverse response when increased antigen was combined with adjuvant. Larger amounts dampened the T-cell response in mice as compared to a lower dose. While not wishing to be bound to any particular theory, this effect may have contributed to the lower T-cell responses seen in the combination vaccine as the total dosage was three quarters of the larger gD2 dose 3 μg and 4 μg respectively.

TABLE 2

Mouse HSV2 Neutralizing Antibodies

| Group | Treatment | Animals with detectable Neutralizing Antibody | Average Positive Titer |
|---|---|---|---|
| I | gD2t | 0/5 | N/A |
| II | gD2t/JVRS-100 | 0/5 | N/A |
| III | gD2t | 0/5 | N/A |
| IV | gD2t/JVRS-100 | 1/5 | 50 |
| V | gD2t/MPLalum | 1/5 | 25 |
| VI | gB | 0/5 | N/A |
| VII | gB/JVRS-100 | 5/5 | 60 |
| VIII | gH/gL | 0/5 | N/A |
| IX | gH/gL/JVRS-100 | 0/5 | N/A |
| X | gD2t + gB + gH/gL | 1/5 | 25 |
| XI | gD2t + gB + gH/gL/JVRS-100 | 4/5 | 25 |
| XII | none | 0/5 | N/A |

TABLE 3

Non Human Primate Vaccination Regimen

| Group (N = 4) | Vaccine/ adjuvant | Antigen Dose | Route and volume | Vaccinations | Plasma/ PBMC collection |
|---|---|---|---|---|---|
| I | gD2t/MPLalum | 20 μg | IM, 0.5 mL | Days 0, 21 | Day 0, 21, 42 |
| II | gD2t/JVRS-100 | 20 μg | IM, 0.5 mL | Days 0, 21 | Day 0, 21, 42 |
| III | gD2t + gB + gHgL/MPLalum | 20 μg of ea. | IM, 0.5 mL | Days 0, 21 | Day 0, 21, 42 |
| IV | gD2t + gB + gHgL/JVRS-100 | 20 μg of ea. | IM, 0.5 mL | Days 0, 21 | Day 0, 21, 42 |
| V | gD2t + gB + gHgL | 20 μg of ea. | IM, 0.5 mL | Days 0, 21 | Day 0, 21, 42 |
| VI | gD2/JVRS-100 | 20 μg | IM, 0.5 mL | Days 0, 21 | Day 0, 21, 42 |

TABLE 4

Non-human Primate HSV2 Neutralizing Antibodies

| Group | Treatment | Animals with detectable Neutralizing Antibody | Average Positive Titer |
|---|---|---|---|
| I | gD2t/MPLalum | 1/4 | 100 |
| II | gD2t/JVRS-100 | 4/4 | 68.75 |
| III | gD2t + gB + gH/gL/MPLalum | 0/4 | N/A |

TABLE 1

Mouse Vaccination Regimen

| Group (N = 10) | Vaccine/adjuvant | Antigen Dose | Route and volume | Vaccinations | Blood/Spleen collection (N = 5) | HSV-2 challenge (N = 5) | Vaginal Swabs (N = 5) |
|---|---|---|---|---|---|---|---|
| I | gD2t | 1 μg | IM, 0.1 mL | Days 0, 21 | Day 36 | Day 36 | Days 38, 40, 42 |
| II | gD2t/JVRS-100 | 1 μg | IM, 0.1 mL | Days 0, 21 | Day 36 | Day 36 | Days 38, 40, 42 |
| III | gD2t | 4 μg | IM, 0.1 mL | Days 0, 21 | Day 36 | Day 36 | Days 38, 40, 42 |
| IV | gD2t/JVRS-100 | 4 μg | IM, 0.1 mL | Days 0, 21 | Day 36 | Day 36 | Days 38, 40, 42 |
| V | gD2t/MPLalum | 1 μg | IM, 0.1 mL | Days 0, 21 | Day 36 | Day 36 | Days 38, 40, 42 |
| VI | gB | 1 μg | IM, 0.1 mL | Days 0, 21 | Day 36 | Day 36 | Days 38, 40, 42 |
| VII | gB/JVRS-100 | 1 μg | IM, 0.1 mL | Days 0, 21 | Day 36 | Day 36 | Days 38, 40, 42 |
| VIII | gHgL | 1 μg | IM, 0.1 mL | Days 0, 21 | Day 36 | Day 36 | Days 38, 40, 42 |
| IX | gHgL/JVRS-100 | 1 μg | IM, 0.1 mL | Days 0, 21 | Day 36 | Day 36 | Days 38, 40, 42 |
| X | gD2t + gB + gHgL | 1 μg of ea. | IM, 0.1 mL | Days 0, 21 | Day 36 | Day 36 | Days 38, 40, 42 |
| XI | gD2t + gB + gHgL/JVRS-100 | 1 μg of ea. | IM, 0.1 mL | Days 0, 21 | Day 36 | Day 36 | Days 38, 40, 42 |
| XII | No treatment | N/A | N/A | Days 0, 21 | Day 36 | Day 36 | Days 38, 40, 42 |

TABLE 4-continued

Non-human Primate HSV2 Neutralizing Antibodies

| Group | Treatment | Animals with detectable Neutralizing Antibody | Average Positive Titer |
|---|---|---|---|
| IV | gD2t + gB + gH/gL/JVRS-100 | 4/4 | 56.25 |
| V | gD2t + gB + gH/gL | 1/4 | 25 |
| VI | gD2/JVRS-100 | 4/4 | 100 |

The term "comprising", which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

Although the invention has been described with reference to the above examples, it will be understood that modifications and variations are encompassed within the spirit and scope of the invention. Accordingly, the invention is limited only by the following claims.

What is claimed is:

1. A composition of isolated Herpes Simplex Virus type 2 (HSV-2) antigens comprising:
   i) an isolated glycoprotein B2 (gB2) fragment, wherein the fragment of gB2 consists of amino acid residues 31-726 or amino acid residues 31-727, wherein residue numbering begins at the starting methionine of gB2;
   ii) an isolated glycoprotein H2 (gH2) fragment in a complex with glycoprotein L2 (gL2) or a fragment thereof, wherein the fragment of gH2 consists of amino acid residues 21-802, wherein residue numbering begins at the starting methionine of gH2, and wherein the gL2 or fragment thereof comprises the ectodomain of the full length protein; and
   iii) an adjuvant, in an amount effective to enhance the immune response to said antigens of steps i) and ii), comprising a cationic liposome delivery vehicle and an isolated non-coding nucleic acid molecule.

2. The composition of claim 1, further comprising an isolated glycoprotein D2 (gD2) fragment, wherein the fragment of gD2 consists of amino acid residues 1-285, wherein residue numbering begins at the starting methionine of gD2.

3. The composition of claim 1, wherein the isolated non-coding nucleic acid molecule is selected from the group consisting of:
   i) an isolated nucleic acid molecule that is not operatively linked to a transcription control sequence,
   ii) an isolated bacterially-derived nucleic acid vector without a gene insert, and
   iii) an oligonucleotide comprising a CpG motif.

4. The composition of claim 1, wherein the cationic liposome delivery vehicle comprises one of the following combinations: N-[1-(2,3-dioleoyloxy)propyl]-N,N,N-trimethylammonium chloride (DOTAP) and cholesterol; 1,2-di-O-octadecenyl-3-trimethylammonium propane chloride (DOTMA) and cholesterol; dimethyldioctadecylammonium bromide (DDAB) and cholesterol; or 1-[2-(9-(Z)-octadecenoyloxy)ethyl]-2-(8-(Z)-heptadecenyl)-3-(hydroxyethyl) imidazolinium chloride (DOTIM) and cholesterol.

5. A method for inducing an immune response in a mammalian subject against herpes simplex virus (HSV), comprising administering to the subject an effective amount of the composition of any of claims 1, 2, 3, or 4.

6. An isolated nucleic acid molecule consisting essentially of a nucleotide sequence encoding a HSV2 glycoprotein B2 (gB2) fragment, in-frame with a nucleotide sequence encoding a HSV2 glycoprotein H2 (gH2) fragment, and in-frame with a nucleotide sequence encoding HSV2 glycoprotein L2 (gL2) or a fragment thereof;
   wherein the fragment of gB2 consists of amino acid residues 31-726 or amino acid residues 31-727, wherein residue number begins at the starting methionine of gB2;
   wherein the fragment of gH2 consists of amino acid residues 21-802, wherein residue numbering begins at the starting methionine of gH2; and
   wherein the gL2 or fragment thereof comprises the ectodomain of the full length protein.

7. An isolated nucleic acid molecule consisting essentially of a HSV2 nucleotide sequence encoding glycoprotein B2 (gB2) fragment, in-frame with a nucleotide sequence encoding a HSV2 glycoprotein H2 (gH2) fragment, in-frame with a nucleotide sequence encoding HSV2 glycoprotein L2 (gL2) or a fragment thereof, and in-frame with a nucleotide sequence encoding a HSV2 glycoprotein D2 (gD2) fragment;
   wherein the fragment of gB2 consists of amino acid residues 31-726 or amino acid residues 31-727, wherein residue number begins at the starting methionine of gB2;
   wherein the fragment of gH2 consists of amino acid residues 21-802, wherein residue numbering begins at the starting methionine of gH2; and
   wherein the gL2 or fragment thereof comprises the ectodomain of the full length protein; and
   wherein the fragment of gD2 consists of amino acid residues 1-285, wherein residue numbering begins at the starting methionine of gD2.

8. A composition comprising the isolated nucleic acid molecule of claim 6.

9. A composition comprising the isolated nucleic acid molecule of claim 7.

10. The composition of claim 8 or claim 9, wherein the nucleic acids are complexed with a cationic liposome delivery vehicle to form a cationic liposome DNA complex (CLDC).

11. The composition of claim 10, wherein the cationic liposome delivery vehicle comprises one of the following combinations: DOTAP and cholesterol; DOTMA and cholesterol; DDAB and cholesterol; or DOTIM and cholesterol.

12. A method for inducing an immune response in a mammalian subject against HSV-2, comprising concurrently or sequentially administering to the subject an effective amount of an isolated nucleic acid molecule according to claim 6 or 7, wherein the nucleic acid molecule is complexed with a cationic liposome delivery vehicle.

13. The method of claim 12, further comprising concurrently or sequentially administering an isolated nucleic acid molecule encoding a glycoprotein D (gD) in an adjuvant.

14. The method of claim 12, wherein the cationic liposome delivery vehicle comprises one of the following combinations: DOTAP and cholesterol; DOTMA and cholesterol; DDAB and cholesterol; or DOTIM and cholesterol.

15. The composition of any one of claims 1, 2, 3, 4, or 6-9, further comprising a pharmaceutically acceptable excipient.

16. The composition of claim 15, wherein the excipient comprises a non-ionic diluent.

17. The composition of claim 15, wherein the excipient is 5 percent (w/v) dextrose in water.

* * * * *

SEQUENCE LISTING

```
<160> NUMBER OF SEQ ID NOS: 17

<210> SEQ ID NO 1
<211> LENGTH: 393
<212> TYPE: PRT
<213> ORGANISM: Herpes simplex virus 2
<220> FEATURE:
<221> NAME/KEY: SIGNAL
<222> LOCATION: (1)..(25)
<220> FEATURE:
<221> NAME/KEY: mat_peptide
<222> LOCATION: (26)..(393)

<400> SEQUENCE: 1

Met Gly Arg Leu Thr Ser Gly Val Gly Thr Ala Ala Leu Leu Val Val
-25                 -20                 -15                 -10

Ala Val Gly Leu Arg Val Val Cys Ala Lys Tyr Ala Leu Ala Asp Pro
                -5                  -1  1               5

Ser Leu Lys Met Ala Asp Pro Asn Arg Phe Arg Gly Lys Asn Leu Pro
        10                  15                  20

Val Leu Asp Arg Leu Thr Asp Pro Pro Gly Val Lys Arg Val Tyr His
    25                  30                  35

Ile Gln Pro Ser Leu Glu Asp Pro Phe Gln Pro Pro Ser Ile Pro Ile
40                  45                  50                  55

Thr Val Tyr Tyr Ala Val Leu Glu Arg Ala Cys Arg Ser Val Leu Leu
                60                  65                  70

His Ala Pro Ser Glu Ala Pro Gln Ile Val Arg Gly Ala Ser Asp Glu
            75                  80                  85

Ala Arg Lys His Thr Tyr Asn Leu Thr Ile Ala Trp Tyr Arg Met Gly
        90                  95                  100

Asp Asn Cys Ala Ile Pro Ile Thr Val Met Glu Tyr Thr Glu Cys Pro
    105                 110                 115

Tyr Asn Lys Ser Leu Gly Val Cys Pro Ile Arg Thr Gln Pro Arg Trp
120                 125                 130                 135
```

```
Ser Tyr Tyr Asp Ser Phe Ser Ala Val Ser Glu Asp Asn Leu Gly Phe
            140                 145                 150
Leu Met His Ala Pro Ala Phe Glu Thr Ala Gly Thr Tyr Leu Arg Leu
        155                 160                 165
Val Lys Ile Asn Asp Trp Thr Glu Ile Thr Gln Phe Ile Leu Glu His
        170                 175                 180
Arg Ala Arg Ala Ser Cys Lys Tyr Ala Leu Pro Leu Arg Ile Pro Pro
        185                 190                 195
Ala Ala Cys Leu Thr Ser Lys Ala Tyr Gln Gln Gly Val Thr Val Asp
200                 205                 210                 215
Ser Ile Gly Met Leu Pro Arg Phe Ile Pro Glu Asn Gln Arg Thr Val
                220                 225                 230
Ala Leu Tyr Ser Leu Lys Ile Ala Gly Trp His Gly Pro Lys Pro Pro
            235                 240                 245
Tyr Thr Ser Thr Leu Leu Pro Pro Glu Leu Ser Asp Thr Thr Asn Ala
        250                 255                 260
Thr Gln Pro Glu Leu Val Pro Glu Asp Pro Glu Asp Ser Ala Leu Leu
        265                 270                 275
Glu Asp Pro Ala Gly Thr Val Ser Ser Gln Ile Pro Pro Asn Trp His
280                 285                 290                 295
Ile Pro Ser Ile Gln Asp Val Ala Pro His His Ala Pro Ala Ala Pro
                300                 305                 310
Ser Asn Pro Gly Leu Ile Ile Gly Ala Leu Ala Gly Ser Thr Leu Ala
            315                 320                 325
Val Leu Val Ile Gly Gly Ile Ala Phe Trp Val Arg Arg Arg Ala Gln
        330                 335                 340
Met Ala Pro Lys Arg Leu Arg Leu Pro His Ile Arg Asp Asp Asp Ala
        345                 350                 355
Pro Pro Ser His Gln Pro Leu Phe Tyr
360                 365

<210> SEQ ID NO 2
<211> LENGTH: 1182
<212> TYPE: DNA
<213> ORGANISM: Herpes simplex virus 2

<400> SEQUENCE: 2
atggggcgtt tgacctccgg cgtcgggacg gcggccctgc tagttgtcgc ggtgggactc      60
cgcgtcgtct gcgccaaata cgccttagca gaccccctcgc ttaagatggc cgatcccaat    120
cgatttcgcg ggaagaacct tccggttttg gaccggctga ccgaccccgc cggggtgaag    180
cgtgtttacc acattcagcc gagcctggag gacccgttcc agcccccccag catcccgatc    240 actgtgtact acgcagtgct ggaacgtgcc tgccgcagcg tgctcctaca tgccccatcg    300
gaggcccccc cagatcgtgcg cggggcttcg gacgaggccc gaaagcacac gtacaacctg    360
accatcgcct ggtatcgcat gggagacaat tgcgctatcc ccatcacggt tatggaatac    420
accgagtgcc cctacaacaa gtcgttgggg gtctgcccca tccgaacgca gccccgctgg    480
agctactatg acagctttag cgccgtcagc gaggataacc tgggattcct gatgcacgcc    540
cccgccttcg agaccgcggg tacgtacctg cggctagtga gataaacga ctggacggag    600 atcacacaat ttatcctgga gcaccgggcc cgcgcctcct gcaagtacgc tctcccctg    660 cgcatccccc cggcagcgtg cctcacctcg aaggcctacc aacagggcgt gacggtcgac    720
agcatcggga tgctcccccg ctttatcccc gaaaaccagc gcaccgtcgc cctatacagc    780
```

-continued

```
ttaaaaatcg ccgggtggca cggccccaag cccccgtaca ccagcaccct gctgccgccg      840
gagctgtccg acaccaccaa cgccacgcaa cccgaactcg ttccggaaga ccccgaggac      900
tcggccctct tagaggatcc cgccgggacg tgtcttcgc agatcccccc aaactggcac       960
atcccgtcga tccaggacgt cgccgccgcac cacgccccg ccgccccag caacccgggc      1020
ctgatcatcg gcgcgctggc cggcagtacc ctggcggtgc tggtcatcgg cggtattgcg     1080
ttttggggtac gccgccgcgc tcagatggcc cccaagcgcc tacgtctccc ccacatccgg    1140
gatgacgacg cgccccctc gcaccagcca ttgtttact ag                          1182
```

<210> SEQ ID NO 3
<211> LENGTH: 901
<212> TYPE: PRT
<213> ORGANISM: Herpes simplex virus 2

<400> SEQUENCE: 3

```
Met Arg Gly Gly Gly Leu Val Cys Ala Leu Val Val Gly Ala Leu Val
1               5                   10                  15

Ala Ala Val Ala Ser Ala Ala Pro Ala Ala Pro Arg Ala Ser Gly Asp
                20                  25                  30

Val Ala Ala Thr Val Ala Ala Asn Gly Gly Pro Ala Ser Gln Pro Pro
            35                  40                  45

Pro Val Pro Ser Pro Ala Thr Thr Lys Ala Arg Lys Arg Lys Thr Lys
        50                  55                  60

Lys Pro Pro Lys Arg Pro Glu Ala Thr Pro Pro Pro Asp Ala Asn Ala
65                  70                  75                  80

Thr Val Ala Ala Gly His Ala Thr Leu Arg Ala His Leu Arg Glu Ile
                85                  90                  95

Lys Val Glu Asn Ala Asp Ala Gln Phe Tyr Val Cys Pro Pro Pro Thr
            100                 105                 110

Gly Ala Thr Val Val Gln Phe Glu Gln Pro Arg Arg Cys Pro Thr Arg
        115                 120                 125

Pro Glu Gly Gln Asn Tyr Thr Glu Gly Ile Ala Val Val Phe Lys Glu
    130                 135                 140

Asn Ile Ala Pro Tyr Lys Phe Lys Ala Thr Met Tyr Tyr Lys Asp Val
145                 150                 155                 160

Thr Val Ser Gln Val Trp Phe Gly His Arg Tyr Ser Gln Phe Met Gly
                165                 170                 175

Ile Phe Glu Asp Arg Ala Pro Val Pro Phe Glu Glu Val Ile Asp Lys
            180                 185                 190

Ile Asn Ala Lys Gly Val Cys Arg Ser Thr Ala Lys Tyr Val Arg Asn
        195                 200                 205

Asn Met Glu Thr Thr Ala Phe His Arg Asp Asp His Glu Thr Asp Met
    210                 215                 220

Glu Leu Lys Pro Ala Lys Val Ala Thr Arg Thr Ser Arg Gly Trp His
225                 230                 235                 240

Thr Thr Asp Leu Lys Tyr Asn Pro Ser Arg Val Glu Ala Phe His Arg
                245                 250                 255

Tyr Gly Thr Thr Val Asn Cys Ile Val Glu Glu Val Asp Ala Arg Ser
            260                 265                 270

Val Tyr Pro Tyr Asp Glu Phe Val Leu Ala Thr Gly Asp Phe Val Tyr
        275                 280                 285

Met Ser Pro Phe Tyr Gly Tyr Arg Glu Gly Ser His Thr Glu His Thr
    290                 295                 300
```

-continued

Ser Tyr Ala Ala Asp Arg Phe Lys Gln Val Asp Gly Phe Tyr Ala Arg
305                 310                 315                 320

Asp Leu Thr Thr Lys Ala Arg Ala Thr Ser Pro Thr Thr Arg Asn Leu
            325                 330                 335

Leu Thr Thr Pro Lys Phe Thr Val Ala Trp Asp Trp Val Pro Lys Arg
            340                 345                 350

Pro Ala Val Cys Thr Met Thr Lys Trp Gln Glu Val Asp Glu Met Leu
            355                 360                 365

Arg Ala Glu Tyr Gly Gly Ser Phe Arg Phe Ser Ser Asp Ala Ile Ser
370                 375                 380

Thr Thr Phe Thr Thr Asn Leu Thr Gln Tyr Ser Leu Ser Arg Val Asp
385                 390                 395                 400

Leu Gly Asp Cys Ile Gly Arg Asp Ala Arg Glu Ala Ile Asp Arg Met
            405                 410                 415

Phe Ala Arg Lys Tyr Asn Ala Thr His Ile Lys Val Gly Gln Pro Gln
            420                 425                 430

Tyr Tyr Leu Ala Thr Gly Gly Phe Leu Ile Ala Tyr Gln Pro Leu Leu
            435                 440                 445

Ser Asn Thr Leu Ala Glu Leu Tyr Val Arg Glu Tyr Met Arg Glu Gln
450                 455                 460

Asp Arg Lys Pro Arg Asn Ala Thr Pro Ala Pro Leu Arg Glu Ala Pro
465                 470                 475                 480

Ser Ala Asn Ala Ser Val Glu Arg Ile Lys Thr Thr Ser Ser Ile Glu
            485                 490                 495

Phe Ala Arg Leu Gln Phe Thr Tyr Asn His Ile Gln Arg His Val Asn
            500                 505                 510

Asp Met Leu Gly Arg Ile Ala Val Ala Trp Cys Glu Leu Gln Asn His
            515                 520                 525

Glu Leu Thr Leu Trp Asn Glu Ala Arg Lys Leu Asn Pro Asn Ala Ile
530                 535                 540

Ala Ser Ala Thr Val Gly Arg Arg Val Ser Ala Arg Met Leu Gly Asp
545                 550                 555                 560

Val Met Ala Val Ser Thr Cys Val Pro Val Ala Pro Asp Asn Val Ile
            565                 570                 575

Val Gln Asn Ser Met Arg Val Ser Ser Arg Pro Gly Thr Cys Tyr Ser
            580                 585                 590

Arg Pro Leu Val Ser Phe Arg Tyr Glu Asp Gln Gly Pro Leu Ile Glu
            595                 600                 605

Gly Gln Leu Gly Glu Asn Asn Glu Leu Arg Leu Thr Arg Asp Ala Leu
610                 615                 620

Glu Pro Cys Thr Val Gly His Arg Arg Tyr Phe Ile Phe Gly Gly Gly
625                 630                 635                 640

Tyr Val Tyr Phe Glu Glu Tyr Ala Tyr Ser His Gln Leu Ser Arg Ala
            645                 650                 655

Asp Val Thr Val Ser Thr Phe Ile Asp Leu Asn Ile Thr Met Leu
            660                 665                 670

Glu Asp His Glu Phe Val Pro Leu Glu Val Tyr Thr Arg His Glu Ile
            675                 680                 685

Lys Asp Ser Gly Leu Leu Asp Tyr Thr Glu Val Gln Arg Arg Asn Gln
            690                 695                 700

Leu His Asp Leu Arg Phe Ala Asp Ile Asp Thr Val Ile Arg Ala Asp
705                 710                 715                 720

Ala Asn Ala Ala Met Phe Ala Gly Leu Cys Ala Phe Phe Glu Gly Met

```
                725                 730                 735
Gly Asp Leu Gly Arg Ala Val Gly Lys Val Val Met Gly Val Val Gly
            740                 745                 750
Gly Val Val Ser Ala Val Ser Gly Val Ser Ser Phe Met Ser Asn Pro
        755                 760                 765
Phe Gly Ala Leu Ala Val Gly Leu Leu Val Leu Ala Gly Leu Val Ala
    770                 775                 780
Ala Phe Phe Ala Phe Arg Tyr Val Leu Gln Leu Gln Arg Asn Pro Met
785                 790                 795                 800
Lys Ala Leu Tyr Pro Leu Thr Thr Lys Glu Leu Lys Thr Ser Asp Pro
                805                 810                 815
Gly Gly Val Gly Gly Glu Gly Glu Gly Ala Glu Gly Gly Gly Phe
            820                 825                 830
Asp Glu Ala Lys Leu Ala Glu Ala Arg Glu Met Ile Arg Tyr Met Ala
        835                 840                 845
Leu Val Ser Ala Met Glu Arg Thr Glu His Lys Ala Arg Lys Lys Gly
    850                 855                 860
Thr Ser Ala Leu Leu Ser Ser Lys Val Thr Asn Met Val Leu Arg Lys
865                 870                 875                 880
Arg Asn Lys Ala Arg Tyr Ser Pro Leu His Asn Glu Asp Glu Ala Gly
                885                 890                 895
Asp Glu Asp Glu Leu
        900

<210> SEQ ID NO 4
<211> LENGTH: 2706
<212> TYPE: DNA
<213> ORGANISM: Herpes simplex virus 2

<400> SEQUENCE: 4
atgcgcgggg ggggcttggt ttgcgcgctg gtcgtggggg cgctggtggc cgcggtggcg    60
tcggcggccc cggcggcccc ccgcgcctcg gcgacgtgg ccgcgaccgt cgcggcgaac    120
gggggtcccg cctcccagcc gcccccgtc ccgagccccg cgaccaccaa ggccggaag    180
cggaaaacca aaaagccgcc caagcggccc gaggcgaccc cgccccccga cgccaacgcg    240
accgtcgccg ccggccacgc cacgctgcgc gcgcacctgc gggaaatcaa ggtcgagaac    300
gccgatgccc agttttacgt gtgcccgccc ccgacgggcg ccacggtggt gcagtttgag    360
cagccgcgcc gctgcccgac gcgcccggag gggcagaact acacggaggg catcgcggtg    420
gtcttcaagg agaacatcgc cccgtacaaa ttcaaggcca ccatgtacta caaagacgtg    480
accgtgtcgc aggtgtggtt cggccaccgc tactcccagt ttatggggat attcgaggac    540
cgcgcccccg ttcccttcga ggaggtgatc gacaagatta cgccaaggg ggtctgccgc    600
tccacggcca gtacgtgcg gaacaacatg agaccaccg cgtttcaccg ggacgaccac    660
gagaccgaca tggagctcaa gccggcgaag gtcgccacgc gcacgagccg ggggtggcac    720
accaccgacc tcaagtacaa ccccctcgcg gtggaggcgt ccatcggta cggcacgacg    780
gtcaactgca tcgtcgagga ggtggacgcg cggtcggtgt acccgtacga tgagtttgtg    840
ctggcgacgg gcgactttgt gtacatgtcc ccgttttacg ctaccgggga ggggtcgcac    900
accgagcaca ccagctacgc cgccgaccgc ttcaagcagg tcgacggctt ctacgcgcgc    960
gacctcacca cgaaggcccg ggccacgtcg ccgacgaccc gcaacttgct gacgaccccc    1020
aagtttaccg tggcctggga ctgggtgccg aagcgaccgg cggtctgcac catgaccaag    1080
```

-continued

```
tggcaggagg tggacgagat gctccgcgcc gagtacggcg gctccttccg cttctcctcc      1140
gacgccatct cgaccacctt caccaccaac ctgacccagt actcgctctc gcgcgtcgac      1200
ctgggcgact gcatcggccg ggatgcccgc gaggccatcg accgcatgtt tgcgcgcaag      1260
tacaacgcca cgcacatcaa ggtgggccag ccgcagtact acctggccac ggggggcttc      1320
ctcatcgcgt accagcccct cctcagcaac acgctcgccg agctgtacgt gcgggagtac      1380
atgcgggagc aggaccgcaa gccccggaat gccacgcccg cgccactgcg ggaggcgccc      1440
agcgccaacg cgtccgtgga gcgcatcaag accacctcct cgatcgagtt cgcccggctg      1500
cagtttacgt ataaccacat acagcgccac gtgaacgaca tgctggggcg catcgccgtc      1560
gcgtggtgcg agctgcagaa ccacgagctg actctctgga acgaggcccg caagctcaac      1620
cccaacgcca tcgcctccgc caccgtcggc cggcgggtga gcgcgcgcat gctcggagac      1680
gtcatggccg tctccacgtg cgtgcccgtc gccccggaca acgtgatcgt gcagaactcg      1740
atgcgcgtca gctcgcggcc ggggacgtgc tacagccgcc ccctggtcag ctttcggtac      1800
gaagaccagg gcccgctgat cgaggggcag ctgggcgaga caacgagct gcgcctcacc       1860
cgcgacgcgc tcgagccgtg caccgtgggc caccggcgct acttcatctt cggcgggggc      1920
tacgtgtact cgaggagta cgcgtactct caccagctga gtcgcgccga cgtcaccacc       1980
gtcagcacct tcatcgacct gaacatcacc atgctggagg accacgagtt tgtgccctg      2040
gaggtctaca cgcgccacga gatcaaggac agccggcctg ctggactaca cggaggtccag     2100
cgccgcaacc agctgcacga cctgcgcttt gccgacatcg acacggtcat ccgcgccgac      2160
gccaacgccg ccatgttcgc ggggctgtgc gcgttcttcg aggggatggg ggacttgggg      2220
cgcgcggtcg gcaaggtcgt catgggagta gtggggggcg tggtgtcggc cgtctcgggc      2280
gtgtcctcct ttatgtccaa ccccttcggg gcgcttgccg tggggctgct ggtcctggcc      2340
ggcctggtcg cggccttctt cgccttccgc tacgtcctgc aactgcaacg caatcccatg      2400
aaggccctgt atccgctcac caccaaggaa ctcaagactt ccgaccccgg gggcgtgggc      2460
ggggagggg aggaaggcgc ggaggggggc gggtttgacg aggccaagtt ggccgaggcc       2520
cgagaaatga tccgatatat ggctttggtg tcggccatgg agcgcacgga acacaaggcc      2580
agaaagaagg gcacgagcgc cctgctcagc tccaaggtca ccaacatggt tctgcgcaag      2640
cgcaacaaag ccaggtactc tccgctccac aacgaggacg aggccggaga cgaagacgag      2700
ctctaa                                                                2706
```

<210> SEQ ID NO 5
<211> LENGTH: 838
<212> TYPE: PRT
<213> ORGANISM: Herpes simplex virus 2

<400> SEQUENCE: 5

```
Met Gly Pro Gly Leu Trp Val Met Gly Val Leu Val Gly Val Ala
1               5                   10                  15

Gly Gly His Asp Thr Tyr Trp Thr Glu Gln Ile Asp Pro Trp Phe Leu
            20                  25                  30

His Gly Leu Gly Leu Ala Arg Thr Tyr Trp Arg Asp Thr Asn Thr Gly
        35                  40                  45

Arg Leu Trp Leu Pro Asn Thr Pro Asp Ala Ser Asp Pro Gln Arg Gly
    50                  55                  60

Arg Leu Ala Pro Pro Gly Glu Leu Asn Leu Thr Thr Ala Ser Val Pro
65                  70                  75                  80
```

```
Met Leu Arg Trp Tyr Ala Glu Arg Phe Cys Phe Val Leu Val Thr Thr
             85                  90                  95
Ala Glu Phe Pro Arg Asp Pro Gly Gln Leu Leu Tyr Ile Pro Lys Thr
        100                 105                 110
Tyr Leu Leu Gly Arg Pro Arg Asn Ala Ser Leu Pro Glu Leu Pro Glu
    115                 120                 125
Ala Gly Pro Thr Ser Arg Pro Pro Ala Glu Val Thr Gln Leu Lys Gly
130                 135                 140
Leu Ser His Asn Pro Gly Ala Ser Ala Leu Leu Arg Ser Arg Ala Trp
145                 150                 155                 160
Val Thr Phe Ala Ala Pro Asp Arg Glu Gly Leu Thr Phe Pro Arg
                165                 170                 175
Gly Asp Asp Gly Ala Thr Glu Arg His Pro Asp Gly Arg Arg Asn Ala
            180                 185                 190
Pro Pro Pro Gly Pro Pro Ala Gly Thr Pro Arg His Pro Thr Thr Asn
        195                 200                 205
Leu Ser Ile Ala His Leu His Asn Ala Ser Val Thr Trp Leu Ala Ala
    210                 215                 220
Arg Gly Leu Leu Arg Thr Pro Gly Arg Tyr Val Tyr Leu Ser Pro Ser
225                 230                 235                 240
Ala Ser Thr Trp Pro Val Gly Val Trp Thr Thr Gly Leu Ala Phe
                245                 250                 255
Gly Cys Asp Ala Ala Leu Val Arg Ala Arg Tyr Gly Lys Gly Phe Met
            260                 265                 270
Gly Leu Val Ile Ser Met Arg Asp Ser Pro Pro Ala Glu Ile Ile Val
        275                 280                 285
Val Pro Ala Asp Lys Thr Leu Ala Arg Val Gly Asn Pro Thr Asp Glu
    290                 295                 300
Asn Ala Pro Ala Val Leu Pro Gly Pro Pro Ala Gly Pro Arg Tyr Arg
305                 310                 315                 320
Val Phe Val Leu Gly Ala Pro Thr Pro Ala Asp Asn Gly Ser Ala Leu
                325                 330                 335
Asp Ala Leu Arg Arg Val Ala Gly Tyr Pro Glu Glu Ser Thr Asn Tyr
            340                 345                 350
Ala Gln Tyr Met Ser Arg Ala Tyr Ala Glu Phe Leu Gly Glu Asp Pro
        355                 360                 365
Gly Ser Gly Thr Asp Ala Arg Pro Ser Leu Phe Trp Arg Leu Ala Gly
    370                 375                 380
Leu Leu Ala Ser Ser Gly Phe Ala Phe Val Asn Ala Ala His Ala His
385                 390                 395                 400
Asp Ala Ile Arg Leu Ser Asp Leu Leu Gly Phe Leu Ala His Ser Arg
                405                 410                 415
Val Leu Ala Gly Leu Ala Ala Arg Gly Ala Ala Gly Cys Ala Ala Asp
            420                 425                 430
Ser Val Phe Leu Asn Val Ser Val Leu Asp Pro Ala Ala Arg Leu Arg
        435                 440                 445
Leu Glu Ala Arg Leu Gly His Leu Val Ala Ala Ile Leu Glu Arg Glu
    450                 455                 460
Gln Ser Leu Val Ala His Ala Leu Gly Tyr Gln Leu Ala Phe Val Leu
465                 470                 475                 480
Asp Ser Pro Ala Ala Tyr Gly Ala Val Ala Pro Ser Ala Ala Arg Leu
                485                 490                 495
Ile Asp Ala Leu Tyr Ala Glu Phe Leu Gly Gly Arg Ala Leu Thr Ala
```

```
            500                 505                 510
Pro Met Val Arg Arg Ala Leu Phe Tyr Ala Thr Ala Val Leu Arg Ala
            515                 520                 525
Pro Phe Leu Ala Gly Ala Pro Ser Ala Glu Gln Arg Glu Arg Ala Arg
            530                 535                 540
Arg Gly Leu Leu Ile Thr Thr Ala Leu Cys Thr Ser Asp Val Ala Ala
545                 550                 555                 560
Ala Thr His Ala Asp Leu Arg Ala Ala Leu Ala Arg Thr Asp His Gln
                565                 570                 575
Lys Asn Leu Phe Trp Leu Pro Asp His Phe Ser Pro Cys Ala Ala Ser
            580                 585                 590
Leu Arg Phe Asp Leu Ala Glu Gly Gly Phe Ile Leu Asp Ala Leu Ala
            595                 600                 605
Met Ala Thr Arg Ser Asp Ile Pro Ala Asp Val Met Ala Gln Gln Thr
            610                 615                 620
Arg Gly Val Ala Ser Val Leu Thr Arg Trp Ala His Tyr Asn Ala Leu
625                 630                 635                 640
Ile Arg Ala Phe Val Pro Glu Ala Thr His Gln Cys Ser Gly Pro Ser
                645                 650                 655
His Asn Ala Glu Pro Arg Ile Leu Val Pro Ile Thr His Asn Ala Ser
            660                 665                 670
Tyr Val Val Thr His Thr Pro Leu Pro Arg Gly Ile Gly Tyr Lys Leu
            675                 680                 685
Thr Gly Val Asp Val Arg Arg Pro Leu Phe Ile Thr Tyr Leu Thr Ala
            690                 695                 700
Thr Cys Glu Gly His Ala Arg Glu Ile Glu Pro Lys Arg Leu Val Arg
705                 710                 715                 720
Thr Glu Asn Arg Arg Asp Leu Gly Leu Val Gly Ala Val Phe Leu Arg
                725                 730                 735
Tyr Thr Pro Ala Gly Glu Val Met Ser Val Leu Leu Val Asp Thr Asp
            740                 745                 750
Ala Thr Gln Gln Gln Leu Ala Gln Gly Pro Val Ala Gly Thr Pro Asn
            755                 760                 765
Val Phe Ser Ser Asp Val Pro Ser Val Ala Leu Leu Leu Phe Pro Asn
            770                 775                 780
Gly Thr Val Ile His Leu Leu Ala Phe Asp Thr Leu Pro Ile Ala Thr
785                 790                 795                 800
Ile Ala Pro Gly Phe Leu Ala Ala Ser Ala Leu Gly Val Val Met Ile
                805                 810                 815
Thr Ala Ala Leu Ala Gly Ile Leu Arg Val Val Arg Thr Cys Val Pro
            820                 825                 830
Phe Leu Trp Arg Arg Glu
            835

<210> SEQ ID NO 6
<211> LENGTH: 2517
<212> TYPE: DNA
<213> ORGANISM: Herpes simplex virus 2

<400> SEQUENCE: 6
atgggccccg gtctgtgggt ggtgatgggg gtcctggtgg gcgttgccgg gggccatgac     60
acgtactgga cggagcaaat cgacccgtgg ttttttgcacg gtctgggggtt ggcccgcacg    120 tactggcgcg acacaaacac cgggcgtctg tggttgccca cacccccga cgccagcgac    180
```

```
ccccagcgcg gacgcttggc gccccgggc gaactcaacc tgactacggc atccgtgccc    240
atgcttcggt ggtacgccga gcgcttttgt ttcgtgttgg tcaccacggc cgagtttcct    300
cgggaccccg ggcagctgct ttacatccca aagacctatc tgctcggccg gcctcggaac    360
gcgagcctgc ccgagctccc cgaggcgggg cccacgtccc gtcccccgc cgaggtgacc     420
cagctcaagg gactgtcgca caaccccggc gcctccgcgc tgttgcggtc ccgggcctgg    480
gtaacattcg cggccgcgcc ggaccgcgag gggcttacgt tcccgcgggg agacgacggg    540
gcgaccgaga ggcacccgga cggccgacgc aacgcgccgc cccggggcc gcccgcgggg     600
acaccgaggc atccgacgac gaacctgagc atcgcgcatc tgcacaacgc atccgtgacc    660
tggctggccg ccaggggcct gctacggact ccgggtcggt acgtgtacct ctccccgtcg    720
gcctcgacgt ggcccgtggg cgtctggacg acgggcgggc tggcgttcgg gtgcgacgcc    780
gcgctcgtgc gcgcgcgata cgggaagggc ttcatggggc tcgtgatatc gatgcgggac    840
agccctccgg ccgagatcat agtggtgcct gcggacaaga ccctcgctcg ggtcggaaat    900
ccgaccgacg aaaacgcccc cgcggtgctc cccgggcctc cggccggccc caggtatcgc    960
gtctttgtcc tgggggcccc gacgcccgcc gacaacggct cggcgctgga cgccctccgg   1020
cgggtggccg gctaccccga ggagagcacg aactacgccc agtatatgtc gcgggcctat   1080
gcggagtttt tgggggagga cccgggctcc ggcacggacg cgcgtccgtc cctgttctgg   1140
cgcctcgcgg ggctgctcgc ctcgtcgggg tttgcgttcg tcaacgcggc ccacgcccac   1200
gacgcgattc gcctctccga cctgctgggc ttttttggcc actcgcgcgt gctggccggc   1260
ctggccgccc ggggagcagc gggctgcgcg gccgactcgg tgttcctgaa cgtgtccgtg   1320
ttggacccgg cggccgcct gcggctggag gcgcgcctcg ggcatctggt ggccgcgatc   1380
ctcgagcgag agcagagcct ggtggcgcac gcgctgggct atcagctggc gttcgtgttg   1440
gacagccccg cggcctatgg cgcggtggcc ccgagcgcgg cccgcctgat cgacgccctg   1500
tacgccgagt ttctcggcgg ccgcgcgcta accgccccga tggtccgccg agcgctgttt   1560
tacgccacgg ccgtcctccg ggcgccgttc ctggcgggcg cgccctcggc cgagcagcgg   1620
gaacgcgccc gccggggcct cctcataacc acggccctgt gtacgtccga cgtcgccgcg   1680
gcgacccacg ccgatctccg ggccgcgcta gccaggaccg accaccagaa aaacctcttc   1740
tggctcccgg accacttttc cccatgcgca gcttccctgc gcttcgatct cgccgagggc   1800
gggttcatcc tggacgcgct ggccatggcc accgatccg acatcccggc ggacgtcatg    1860
gcacaacaga cccgcggcgt ggcctccgtt ctcacgcgct gggcgactac aacgccctg    1920
atccgcgcct tcgtcccgga ggccacccac cagtgtagcg gccgtcgca caacgcggag    1980
ccccggatcc tcgtgcccat cacccacaac gccagctacg tcgtcaccca cccccttg     2040
ccccgcggga tcggatacaa gcttacgggc gttgacgtcc gccgcccgct gtttatcacc   2100
tatctcaccg ccacctgcga agggcacgcg cgggagattg agccgaagcg gctggtgcgc   2160
accgaaaacc ggcgcgacct cggcctcgtg ggggccgtgt ttctgcgcta caccccggcc   2220
ggggaggtca tgtcggtgct gctggtggac acggatgcca cccaacagca gctggcccag   2280
gggcggtgg cgggcacccc gaacgtgttt tccagcgacg tgccgtccgt ggccctgttg    2340
ttgttcccca acggaactgt gattcatctg ctggcctttg acacgctgcc catcgccacc   2400
atcgccccg gtttctggc cgcgtccgcg ctggggggtcg ttatgattac cgcggccctg   2460
gcgggcatcc ttagggtggt ccgaacgtgc gtcccatttt tgtgggagacg cgaataa     2517
```

```
<210> SEQ ID NO 7
<211> LENGTH: 224
<212> TYPE: PRT
<213> ORGANISM: Herpes simplex virus 2

<400> SEQUENCE: 7

Met Gly Phe Val Cys Leu Phe Gly Leu Val Val Met Gly Ala Trp Gly
1               5                   10                  15

Ala Trp Gly Gly Ser Gln Ala Thr Glu Tyr Val Leu Arg Ser Val Ile
            20                  25                  30

Ala Lys Glu Val Gly Asp Ile Leu Arg Val Pro Cys Met Arg Thr Pro
        35                  40                  45

Ala Asp Asp Val Ser Trp Arg Tyr Glu Ala Pro Ser Val Ile Asp Tyr
    50                  55                  60

Ala Arg Ile Asp Gly Ile Phe Leu Arg Tyr His Cys Pro Gly Leu Asp
65                  70                  75                  80

Thr Phe Leu Trp Asp Arg His Ala Gln Arg Ala Tyr Leu Val Asn Pro
                85                  90                  95

Phe Leu Phe Ala Ala Gly Phe Leu Glu Asp Leu Ser His Ser Val Phe
            100                 105                 110

Pro Ala Asp Thr Gln Glu Thr Thr Thr Arg Arg Ala Leu Tyr Lys Glu
        115                 120                 125

Ile Arg Asp Ala Leu Gly Ser Arg Lys Gln Ala Val Ser His Ala Pro
    130                 135                 140

Val Arg Ala Gly Cys Val Asn Phe Asp Tyr Ser Arg Thr Arg Arg Cys
145                 150                 155                 160

Val Gly Arg Arg Asp Leu Arg Pro Ala Asn Thr Thr Ser Thr Trp Glu
                165                 170                 175

Pro Pro Val Ser Ser Asp Asp Glu Ala Ser Ser Gln Ser Lys Pro Leu
            180                 185                 190

Ala Thr Gln Pro Pro Val Leu Ala Leu Ser Asn Ala Pro Pro Arg Arg
        195                 200                 205

Val Ser Pro Thr Arg Gly Arg Arg His Thr Arg Leu Arg Arg Asn
    210                 215                 220

<210> SEQ ID NO 8
<211> LENGTH: 675
<212> TYPE: DNA
<213> ORGANISM: Herpes simplex virus 2

<400> SEQUENCE: 8
atggggttcg tctgtctgtt tgggcttgtc gttatgggag cctgggggggc gtggggtggg    60 tcacaggcaa ccgaatatgt tcttcgtagt gttattgcca agagggtggg ggacatacta   120
agagtgcctt gcatgcggac ccccgcggac gatgtttctt ggcgctacga ggccccgtcc   180
gttattgact atgcccgcat agacggaata tttcttcgct atcactgccc ggggttggac   240 acgttttgt gggataggca cgcccagagg gcgtatctgg ttaacccctt tctctttgcg   300
gcgggatttt tggaggactt gagtcactct gtgtttccgg ccgacaccca ggaaacaacg   360
acgcgccggg ccctttataa agagatacgc gatgcgttgg gcagtcgaaa acaggccgtc   420
agccacgcac ccgtcaggc cggggtgtgta aactttgact actcacgcac tcgccgctgc   480
gtcgggcgac gcgatttacg gcctgccaac accacgtcaa cgtgggaacc gcctgtgtcg   540
tcggacgatg aagcgagctc gcagtcgaag cccctcgcca cccagccgcc gtcctcgcc   600 ctttcgaacg ccccccccacg gcgggtctcc ccgacgcgag gtcggcgccg gcatactcgc   660
```
ctccgacgca actag 675

<210> SEQ ID NO 9
<211> LENGTH: 394
<212> TYPE: PRT
<213> ORGANISM: Herpes simplex virus 1
<220> FEATURE:
<221> NAME/KEY: SIGNAL
<222> LOCATION: (1)..(25)
<220> FEATURE:
<221> NAME/KEY: mat_peptide
<222> LOCATION: (26)..(394)

<400> SEQUENCE: 9

Met Gly Gly Thr Ala Ala Arg Leu Gly Ala Val Ile Leu Phe Val Val
-25              -20                 -15                 -10

Ile Val Gly Leu His Gly Val Arg Gly Lys Tyr Ala Leu Ala Asp Ala
            -5                  -1  1               5

Ser Leu Lys Met Ala Asp Pro Asn Arg Phe Arg Gly Lys Asp Leu Pro
            10                  15                  20

Val Leu Asp Gln Leu Thr Asp Pro Pro Gly Val Arg Arg Val Tyr His
        25                  30                  35

Ile Gln Ala Gly Leu Pro Asp Pro Phe Gln Pro Pro Ser Leu Pro Ile
40                  45                  50                  55

Thr Val Tyr Tyr Ala Val Leu Glu Arg Ala Cys Arg Ser Val Leu Leu
                60                  65                  70

Asn Ala Pro Ser Glu Ala Pro Gln Ile Val Arg Gly Ala Ser Glu Asp
            75                  80                  85

Val Arg Lys Gln Pro Tyr Asn Leu Thr Ile Ala Trp Phe Arg Met Gly
        90                  95                  100

Gly Asn Cys Ala Ile Pro Ile Thr Val Met Glu Tyr Thr Glu Cys Ser
105                 110                 115

Tyr Asn Lys Ser Leu Gly Ala Cys Pro Ile Arg Thr Gln Pro Arg Trp
120                 125                 130                 135

Asn Tyr Tyr Asp Ser Phe Ser Ala Val Ser Glu Asp Asn Leu Gly Phe
                140                 145                 150

Leu Met His Ala Pro Ala Phe Glu Thr Ala Gly Thr Tyr Leu Arg Leu
            155                 160                 165

Val Lys Ile Asn Asp Trp Thr Glu Ile Thr Gln Phe Ile Leu Glu His
        170                 175                 180

Arg Ala Lys Gly Ser Cys Lys Tyr Ala Leu Pro Leu Arg Ile Pro Pro
185                 190                 195

Ser Ala Cys Leu Ser Pro Gln Ala Tyr Gln Gln Gly Val Thr Val Asp
200                 205                 210                 215

Ser Ile Gly Met Leu Pro Arg Phe Ile Pro Glu Asn Gln Arg Thr Val
                220                 225                 230

Ala Val Tyr Ser Leu Lys Ile Ala Gly Trp His Gly Pro Lys Ala Pro
            235                 240                 245

Tyr Thr Ser Thr Leu Leu Pro Pro Glu Leu Ser Glu Thr Pro Asn Ala
        250                 255                 260

Thr Gln Pro Glu Leu Ala Pro Glu Asp Pro Glu Asp Ser Ala Leu Leu
265                 270                 275

Glu Asp Pro Val Gly Thr Val Ala Pro Gln Ile Pro Pro Asn Trp His
280                 285                 290                 295

Ile Pro Ser Ile Gln Asp Ala Ala Thr Pro Tyr His Pro Pro Ala Thr
                300                 305                 310

```
Pro Asn Asn Met Gly Leu Ile Ala Gly Ala Val Gly Gly Ser Leu Leu
            315                 320                 325

Ala Ala Leu Val Ile Cys Gly Ile Val Tyr Trp Met His Arg Arg Thr
        330                 335                 340

Arg Lys Ala Pro Lys Arg Ile Arg Leu Pro His Ile Arg Glu Asp Asp
    345                 350                 355

Gln Pro Ser Ser His Gln Pro Leu Phe Tyr
360                 365

<210> SEQ ID NO 10
<211> LENGTH: 1608
<212> TYPE: DNA
<213> ORGANISM: Herpes simplex virus 1

<400> SEQUENCE: 10
gtggccccgg cccccaacaa aaatcacggt agcccggccg tgtgacacta tcgtccatac        60
cgaccacacc gacgaacccc taaggggag gggccatttt acgaggagga gggtataac       120 aaagtctgtc tttaaaaagc aggggttagg gagttgttcg gtcataagct tcagcgcgaa      180
cgaccaacta ccccgatcat cagttatcct taaggtctct tttgtgtggt gcgttccggt      240
atggggggga ctgccgccag gttggggggcc gtgattttgt ttgtcgtcat agtgggcctc    300
catggggtcc gcggcaaata tgccttggcg gatgcctctc tcaagatggc gaccccaat      360 cgctttcgcg gcaaagacct tccggtcctg accagctga ccgacctcc ggggtccgg       420 cgcgtgtacc acatccaggc gggcctaccg gacccgttcc agcccccag cctcccgatc     480 acggtttact acgccgtgtt ggagcgcgcc tgccgcagcg tgctcctaaa cgcaccgtcg    540 gaggccccc agattgtccg cggggcctcc gaagacgtcc ggaaacaacc ctacaacctg     600
accatcgctt ggtttcggat gggaggcaac tgtgctatcc ccatcacggt catggagtac    660
accgaatgct cctacaacaa gtctctgggg gcctgtccca tccgaacgca gccccgctgg   720
aactactatg acagcttcag cgccgtcagc gaggataacc tggggttcct gatgcacgcc    780
cccgcgtttg agaccgccgg cacgtacctg cggctcgtga agataaacga ctggacggag    840
attacacagt ttatcctgga gcaccgagcc aagggctcct gtaagtacgc cctcccgctg    900
cgcatccccc cgtcagcctg cctctccccc caggcctacc agcagggggt gacggtggac    960
agcatcggga tgctgccccg cttcatcccc gagaaccagc gcaccgtcgc cgtatacagc   1020
ttgaagatcg ccgggtggca cgggcccaag gccccataca cgagcaccct gctgccccg    1080 gagctgtccg agacccccaa cgccacgcag ccagaactcg ccccggaaga ccccgaggat  1140
tcggccctct tggaggaccc cgtggggacg gtggcgccgc aaatcccacc aaactggcac   1200
atcccgtcga tccaggacgc cgcgacgcct accatcccc cggccacccc gaacaacatg   1260
ggcctgatcg ccggcgcggt gggcggcagt ctcctggcag ccctggtcat ttgcggaatt   1320
gtgtactgga tgcaccgccg cactcggaaa gccccaaagc gcatacgcct ccccacatc    1380 cgggaagacg accagccgtc ctcgcaccag cccttgtttt actagatacc ccccttaat    1440 gggtgcgggg gggtcaggtc tgcggggttg ggatgggacc ttaactccat ataaagcgag   1500
tctggaaggg gggaaaggcg gacagtcgat aagtcggtag cggggacgc gcacctgttc    1560 cgcctgtcgc acccacagct ttttcgcgaa ccgtcccgtt ttcgggat                 1608

<210> SEQ ID NO 11
<211> LENGTH: 899
<212> TYPE: PRT
<213> ORGANISM: Herpes simplex virus 1
```

<400> SEQUENCE: 11

```
Pro Ala Arg Gly Cys Arg Trp Phe Val Val Trp Ala Leu Leu Gly Leu
1               5                   10                  15

Thr Leu Gly Val Leu Val Ala Ser Ala Ala Pro Ser Ser Pro Gly Thr
            20                  25                  30

Pro Gly Val Ala Ala Ala Thr Gln Ala Ala Asn Gly Gly Pro Ala Thr
            35                  40                  45

Pro Ala Pro Pro Ala Pro Gly Pro Ala Pro Thr Gly Asp Thr Lys Pro
    50                  55                  60

Lys Lys Asn Lys Lys Pro Lys Asn Pro Pro Pro Arg Pro Ala Gly
65                  70                  75                  80

Asp Asn Ala Thr Val Ala Ala Gly His Ala Thr Leu Arg Glu His Leu
                85                  90                  95

Arg Asp Ile Lys Ala Glu Asn Thr Asp Ala Asn Phe Tyr Val Cys Pro
            100                 105                 110

Pro Pro Thr Gly Ala Thr Val Val Gln Phe Glu Gln Pro Arg Arg Cys
            115                 120                 125

Pro Thr Arg Pro Glu Gly Gln Asn Tyr Thr Glu Gly Ile Ala Val Val
    130                 135                 140

Phe Lys Glu Asn Ile Ala Pro Tyr Lys Phe Lys Ala Thr Met Tyr Tyr
145                 150                 155                 160

Lys Asp Val Thr Val Ser Gln Val Trp Phe Gly His Arg Tyr Ser Gln
                165                 170                 175

Phe Met Gly Ile Phe Glu Asp Arg Ala Pro Val Pro Phe Glu Glu Val
            180                 185                 190

Ile Asp Lys Ile Asn Ala Lys Gly Val Cys Arg Ser Thr Ala Lys Tyr
        195                     200                 205

Val Arg Asn Asn Leu Glu Thr Thr Ala Phe His Arg Asp Asp His Glu
    210                 215                 220

Thr Asp Met Glu Leu Lys Pro Ala Asn Ala Ala Thr Arg Thr Ser Arg
225                 230                 235                 240

Gly Trp His Thr Thr Asp Leu Lys Tyr Asn Pro Ser Arg Val Glu Ala
            245                 250                 255

Phe His Arg Tyr Gly Thr Thr Val Asn Cys Ile Val Glu Glu Val Asp
        260                 265                 270

Ala Arg Ser Val Tyr Pro Tyr Asp Glu Phe Val Leu Ala Thr Gly Asp
    275                 280                 285

Phe Val Tyr Met Ser Pro Phe Tyr Gly Tyr Arg Glu Gly Ser His Thr
    290                 295                 300

Glu His Thr Ser Tyr Ala Ala Asp Arg Phe Lys Gln Val Asp Gly Phe
305                 310                 315                 320

Tyr Ala Arg Asp Leu Thr Thr Lys Ala Arg Ala Thr Ala Pro Thr Thr
            325                 330                 335

Arg Asn Leu Leu Thr Thr Pro Lys Phe Thr Val Ala Trp Asp Trp Val
            340                 345                 350

Pro Lys Arg Pro Ser Val Cys Thr Met Thr Lys Trp Gln Glu Val Asp
        355                 360                 365

Glu Met Leu Arg Ser Glu Tyr Gly Gly Ser Phe Arg Phe Ser Ser Asp
    370                 375                 380

Ala Ile Ser Thr Thr Phe Thr Thr Asn Leu Thr Glu Tyr Pro Leu Ser
385                 390                 395                 400

Arg Val Asp Leu Gly Asp Cys Ile Gly Lys Asp Ala Arg Asp Ala Met
```

-continued

```
                405                 410                 415
Asp Arg Ile Phe Ala Arg Arg Tyr Asn Ala Thr His Ile Lys Val Gly
            420                 425                 430
Gln Pro Gln Tyr Tyr Leu Ala Asn Gly Gly Phe Leu Ile Ala Tyr Gln
            435                 440                 445
Pro Leu Leu Ser Asn Thr Leu Ala Glu Leu Tyr Val Arg Glu His Leu
450                 455                 460
Arg Glu Gln Ser Arg Lys Pro Pro Asn Pro Thr Pro Pro Pro Pro Gly
465                 470                 475                 480
Ala Ser Ala Asn Ala Ser Val Glu Arg Ile Lys Thr Thr Ser Ser Ile
            485                 490                 495
Glu Phe Ala Arg Leu Gln Phe Thr Tyr Asn His Ile Gln Arg His Val
            500                 505                 510
Asn Asp Met Leu Gly Arg Val Ala Ile Ala Trp Cys Glu Leu Gln Asn
            515                 520                 525
His Glu Leu Thr Leu Trp Asn Glu Ala Arg Lys Leu Asn Pro Asn Ala
            530                 535                 540
Ile Ala Ser Ala Thr Val Gly Arg Arg Val Ser Ala Arg Met Leu Gly
545                 550                 555                 560
Asp Val Met Ala Val Ser Thr Cys Val Pro Val Ala Ala Asp Asn Val
                565                 570                 575
Ile Val Gln Asn Ser Met Arg Ile Ser Ser Arg Pro Gly Ala Cys Tyr
            580                 585                 590
Ser Arg Pro Leu Val Ser Phe Arg Tyr Glu Asp Gln Gly Pro Leu Val
            595                 600                 605
Glu Gly Gln Leu Gly Glu Asn Asn Glu Leu Arg Leu Thr Arg Asp Ala
            610                 615                 620
Ile Glu Pro Cys Thr Val Gly His Arg Arg Tyr Phe Thr Phe Gly Gly
625                 630                 635                 640
Gly Tyr Val Tyr Phe Glu Glu Tyr Ala Tyr Ser His Gln Leu Ser Arg
                645                 650                 655
Ala Asp Ile Thr Thr Val Ser Thr Phe Ile Asp Leu Asn Ile Thr Met
                660                 665                 670
Leu Glu Asp His Glu Phe Val Pro Leu Glu Val Tyr Thr Arg His Glu
            675                 680                 685
Ile Lys Asp Ser Gly Leu Leu Asp Tyr Thr Glu Val Gln Arg Arg Asn
            690                 695                 700
Gln Leu His Asp Leu Arg Phe Ala Asp Ile Asp Thr Val Ile His Ala
705                 710                 715                 720
Asp Ala Asn Ala Ala Met Phe Ala Gly Leu Gly Ala Phe Phe Glu Gly
                725                 730                 735
Met Gly Asp Leu Gly Arg Ala Val Gly Lys Val Val Met Gly Ile Val
            740                 745                 750
Gly Gly Val Val Ser Ala Val Ser Gly Val Ser Ser Phe Met Ser Asn
            755                 760                 765
Pro Phe Gly Ala Leu Ala Val Gly Leu Leu Val Leu Ala Gly Leu Ala
            770                 775                 780
Ala Ala Phe Phe Ala Phe Arg Tyr Val Met Arg Leu Gln Ser Asn Pro
785                 790                 795                 800
Met Lys Ala Leu Tyr Pro Leu Thr Thr Lys Glu Leu Lys Asn Pro Thr
                805                 810                 815
Ser Pro Asp Ala Ser Gly Glu Gly Glu Glu Gly Gly Asp Phe Asp Glu
            820                 825                 830
```

| Ala | Lys | Leu | Ala | Glu | Ala | Arg | Glu | Met | Ile | Arg | Tyr | Met | Ala | Leu | Val |
| | | 835 | | | | | 840 | | | | | 845 | | | |

| Ser | Ala | Met | Glu | Arg | Thr | Glu | His | Lys | Ala | Lys | Lys | Gly | Thr | Ser |
| | 850 | | | | | 855 | | | | | 860 | | | |

| Ala | Leu | Leu | Ser | Ala | Lys | Val | Thr | Asp | Met | Val | Met | Arg | Lys | Arg |
| 865 | | | | | 870 | | | | | 875 | | | | | 880 |

| Ser | Thr | Asn | Tyr | Thr | Gln | Val | Pro | Asn | Lys | Asp | Gly | Asp | Ala | Asp | Glu |
| | | | | 885 | | | | | 890 | | | | | 895 | |

Asp Asp Leu

<210> SEQ ID NO 12
<211> LENGTH: 2700
<212> TYPE: DNA
<213> ORGANISM: Herpes simplex virus 1

<400> SEQUENCE: 12

| cccgcgcggg | ggtgccggtg | gttcgtcgta | tgggcgctct | tggggttgac | gctggggtc | 60 |
| ctggtggcgt | cggcggctcc | gagttccccc | ggcacgcctg | gggtcgcggc | cgcgacccag | 120 |
| gcggcgaacg | gggccctgc | cactccggcg | ccgcccgccc | ctggccccgc | ccaacggg | 180 |
| gacacgaaac | cgaagaagaa | caaaaaaccg | aaaaacccac | cgccgccgcg | ccccgccggc | 240 |
| gacaacgcga | ccgtcgccgc | gggccacgcc | accctgcgcg | agcacctgcg | ggacatcaag | 300 |
| gcggagaaca | ccgatgcgaa | cttttacgtg | tgcccacccc | ccacgggcgc | cacggtggtg | 360 |
| cagttcgagc | agccgcgccg | ctgcccgacc | cggcccgagg | gtcagaacta | cacggagggc | 420 |
| atcgcggtgg | tcttcaagga | gaacatcgcc | ccgtacaagt | tcaaggccac | catgtactac | 480 |
| aaagacgtca | ccgtttcgca | ggtgtggttc | ggccaccgct | actcccagtt | tatgggatc | 540 |
| tttgaggacc | gcgccccgt | cccttcgag | gaggtgatcg | acaagatcaa | cgccaagggg | 600 |
| gtctgtcggt | ccacggccaa | gtacgtgcgc | aacaacctgg | agaccaccgc | gtttcaccgg | 660 |
| gacgaccacg | agaccgacat | ggagctgaaa | ccggccaacg | ccgcgacccg | cacgagccgg | 720 |
| ggctggcaca | ccaccgacct | caagtacaac | ccctcgcggg | tggaggcgtt | ccaccggtac | 780 |
| gggacgacgg | taaactgcat | cgtcgaggag | gtggacgcgc | gctcggtgta | cccgtacgac | 840 |
| gagtttgtgc | tggcgactgg | cgactttgtg | tacatgtccc | cgttttacgg | ctaccgggag | 900 |
| gggtcgcaca | ccgaacacac | cagctacgcc | gccgaccgct | tcaagcaggt | cgacggcttc | 960 |
| tacgcgcgcg | acctcaccac | caaggcccgg | gccacggcgc | cgaccacccg | gaacctgctc | 1020 |
| acgaccccca | agttcaccgt | ggcctgggac | tgggtgccaa | agcgcccgtc | ggtctgcacc | 1080 |
| atgaccaagt | ggcaggaggt | ggacgagatg | ctgcgctccg | agtacggcgg | ctccttccga | 1140 |
| ttctcctccg | acgccatatc | caccaccttc | accaccaacc | tgaccgagta | cccgctctcg | 1200 |
| cgcgtggacc | tggggactg | catcggcaag | gacgcccgcg | acgccatgga | ccgcatcttc | 1260 |
| gcccgcaggt | acaacgcgac | gcacatcaag | gtgggcagc | gcagtacta | cctggccaat | 1320 |
| gggggctttc | tgatcgcgta | ccagccccctt | ctcagcaaca | cgctcgcgga | gctgtacgtg | 1380 |
| cgggaacacc | tccgagagca | gagccgcaag | ccccccaaaac | ccacgccccc | gccgccggg | 1440 |
| gccagcgcca | acgcgtccgt | ggagcgcatc | aagaccacct | cctccatcga | gttcgcccgg | 1500 |
| ctgcagttta | cgtacaacca | catacagcgc | catgtcaacg | atatgttggg | ccgcgttgcc | 1560 |
| atcgcgtggt | gcgagctgca | gaatcacgag | ctgaccctgt | ggaacgaggc | ccgcaagctg | 1620 |
| aaccccaacg | ccatcgcctc | ggccaccgtg | ggccggcggt | tgagcgcgcg | gatgctcggc | 1680 |

```
gacgtgatgg ccgtctccac gtgcgtgccg gtcgccgcgg acaacgtgat cgtccaaaac    1740
tcgatgcgca tcagctcgcg gcccggggcc tgctacagcc gccccctggt cagctttcgg    1800
tacgaagacc agggcccgtt ggtcgagggg cagctggggg agaacaacga gctgcggctg    1860
acgcgcgatg cgatcgagcc gtgcaccgtg gacaccggc gctacttcac cttcggtggg     1920
ggctacgtgt acttcgagga gtacgcgtac tcccaccagc tgagccgcgc cgacatcacc    1980
accgtcagca ccttcatcga cctcaacatc accatgctgg aggatcacga gtttgtcccc    2040
ctggaggtgt acacccgcca cgagatcaag gacagcggcc tgctggacta cacggaggtc    2100
cagcgccgca accagctgca cgacctcgcg tttgccgaca tcgacaccggt catccacgcc    2160 gacgccaacg ccgccatgtt cgcgggcctg ggtgcgtttt tcgagggggat gggcgacctg    2220 gggcgcgcgg tcggcaaggt ggtgatgggc atcgtgggcg gcgtggtatc ggccgtgtcg    2280
ggcgtgtcct ccttcatgtc caaccccttt ggggcgctgg ccgtgggtct gttggtcctg    2340
gccggcctgg cggcggcctt cttcgccttt cgctacgtca tgcggctgca gagcaacccc    2400
atgaaggccc tgtacccgct aaccaccaag gagctcaaga cccccaccag cccggacgcg    2460
tccggggagg gcgaggaggg cggcgactt gacgaggcca gctagccga ggcccgggag       2520 atgatacggt acatggccct ggtgtcggcc atggagcgca cggaacacaa ggccaagaag    2580
aagggcacga gcgcgctgct cagcgccaag gtcaccgaca tggtcatgcg caagcgccgc    2640
agcaccaact acacccaagt ccccaacaaa gacggtgacg ccgacgagga cgacctgtga    2700

<210> SEQ ID NO 13
<211> LENGTH: 838
<212> TYPE: PRT
<213> ORGANISM: Herpes simplex virus 1

<400> SEQUENCE: 13

Met Gly Asn Gly Leu Trp Phe Val Gly Val Ile Ile Leu Gly Val Ala
1               5                   10                  15

Trp Gly Gln Val His Asp Trp Thr Glu Gln Thr Asp Pro Trp Phe Leu
            20                  25                  30

Asp Gly Leu Gly Met Asp Arg Met Tyr Trp Arg Asp Thr Asn Thr Gly
        35                  40                  45

Arg Leu Trp Leu Pro Asn Thr Pro Asp Pro Gln Lys Pro Pro Arg Gly
    50                  55                  60

Phe Leu Ala Pro Pro Asp Glu Leu Asn Leu Thr Thr Ala Ser Leu Pro
65                  70                  75                  80

Leu Leu Arg Trp Tyr Glu Glu Arg Phe Cys Phe Val Leu Val Thr Thr
                85                  90                  95

Ala Glu Phe Pro Arg Asp Pro Gly Gln Leu Leu Tyr Ile Pro Lys Thr
            100                 105                 110

Tyr Leu Leu Gly Arg Pro Pro Asn Ala Ser Leu Pro Ala Pro Thr Thr
        115                 120                 125

Val Glu Pro Thr Ala Gln Pro Pro Ser Val Ala Pro Leu Lys Gly
    130                 135                 140

Leu Leu Tyr Asn Pro Val Ala Ser Val Leu Arg Ser Arg Ala Trp
145                 150                 155             160

Val Thr Phe Ser Ala Val Pro Asp Pro Glu Ala Leu Thr Phe Pro Arg
                165                 170                 175

Gly Asp Asn Val Ala Thr Ala Ser His Pro Ser Gly Pro Arg Asp Thr
            180                 185                 190

Pro Pro Pro Arg Pro Pro Val Gly Ala Arg Arg His Pro Thr Thr Glu
```

```
                    195                 200                 205
Leu Asp Ile Thr His Leu His Asn Ala Ser Thr Thr Trp Leu Ala Thr
210                 215                 220

Arg Gly Leu Leu Arg Ser Pro Gly Arg Tyr Val Tyr Phe Ser Pro Ser
225                 230                 235                 240

Ala Ser Thr Trp Pro Val Gly Ile Trp Thr Thr Gly Glu Leu Val Leu
                245                 250                 255

Gly Cys Asp Ala Ala Leu Val Arg Ala Arg Tyr Gly Arg Glu Phe Met
                260                 265                 270

Gly Leu Val Ile Ser Met His Asp Ser Pro Val Glu Val Met Val
            275                 280                 285

Val Pro Ala Gly Gln Thr Leu Asp Arg Val Gly Asp Pro Ala Asp Glu
        290                 295                 300

Asn Pro Pro Gly Ala Leu Pro Gly Pro Gly Gly Pro Arg Tyr Arg
305                 310                 315                 320

Val Phe Val Leu Gly Ser Leu Thr Arg Ala Asp Asn Gly Ser Ala Leu
                325                 330                 335

Asp Ala Leu Arg Arg Val Gly Gly Tyr Pro Glu Glu Gly Thr Asn Tyr
            340                 345                 350

Ala Gln Phe Leu Ser Arg Ala Tyr Ala Glu Phe Phe Ser Gly Asp Ala
        355                 360                 365

Gly Ala Glu Gln Gly Pro Arg Pro Leu Phe Trp Arg Leu Thr Gly
370                 375                 380

Leu Leu Ala Thr Ser Gly Phe Ala Phe Val Asn Ala Ala His Ala Asn
385                 390                 395                 400

Gly Ala Val Cys Leu Ser Asp Leu Leu Gly Phe Leu Ala His Ser Arg
                405                 410                 415

Ala Leu Ala Gly Leu Ala Ala Arg Gly Ala Ala Gly Cys Ala Ala Asp
            420                 425                 430

Ser Val Phe Phe Asn Val Ser Val Leu Asp Pro Thr Ala Arg Leu Gln
        435                 440                 445

Leu Glu Ala Arg Leu Gln His Leu Val Ala Glu Ile Leu Glu Arg Glu
    450                 455                 460

Gln Ser Leu Ala Leu His Ala Leu Gly Tyr Gln Leu Ala Phe Val Leu
465                 470                 475                 480

Asp Ser Pro Ser Ala Tyr Asp Ala Val Ala Pro Ser Ala Ala His Leu
                485                 490                 495

Ile Asp Ala Leu Tyr Ala Glu Phe Leu Gly Gly Arg Val Leu Thr Thr
            500                 505                 510

Pro Val Val His Arg Ala Leu Phe Tyr Ala Ser Ala Val Leu Arg Gln
        515                 520                 525

Pro Phe Leu Ala Gly Val Pro Ser Ala Val Gln Arg Glu Arg Ala Arg
    530                 535                 540

Arg Ser Leu Leu Ile Ala Ser Ala Leu Cys Thr Ser Asp Val Ala Ala
545                 550                 555                 560

Ala Thr Asn Ala Asp Leu Arg Thr Ala Leu Ala Arg Ala Asp His Gln
                565                 570                 575

Lys Thr Leu Phe Trp Leu Pro Asp His Phe Ser Pro Cys Ala Ala Ser
            580                 585                 590

Leu Arg Phe Asp Leu Asp Glu Ser Val Phe Ile Leu Asp Ala Leu Ala
        595                 600                 605

Gln Ala Thr Arg Ser Glu Thr Pro Val Glu Val Leu Ala Gln Gln Thr
    610                 615                 620
```

His Gly Leu Ala Ser Thr Leu Thr Arg Trp Ala His Tyr Asn Ala Leu
625                 630                 635                 640

Ile Arg Ala Phe Val Pro Glu Ala Ser His Arg Cys Gly Gly Gln Ser
            645                 650                 655

Ala Asn Val Glu Pro Arg Ile Leu Val Pro Ile Thr His Asn Ala Ser
        660                 665                 670

Tyr Val Val Thr His Ser Pro Leu Pro Arg Gly Ile Gly Tyr Lys Leu
    675                 680                 685

Thr Gly Val Asp Val Arg Arg Pro Leu Phe Leu Thr Tyr Leu Thr Ala
690                 695                 700

Thr Cys Glu Gly Ser Thr Arg Asp Ile Glu Ser Lys Arg Leu Val Arg
705                 710                 715                 720

Thr Gln Asn Gln Arg Asp Leu Gly Leu Val Gly Ala Val Phe Met Arg
                725                 730                 735

Tyr Thr Pro Ala Gly Glu Val Met Ser Val Leu Leu Val Asp Thr Asp
            740                 745                 750

Asn Thr Gln Gln Gln Ile Ala Ala Gly Pro Thr Glu Gly Ala Pro Ser
        755                 760                 765

Val Phe Ser Ser Asp Val Pro Ser Thr Ala Leu Leu Phe Pro Asn
    770                 775                 780

Gly Thr Val Ile His Leu Leu Ala Phe Asp Thr Gln Pro Val Ala Ala
785                 790                 795                 800

Ile Ala Pro Gly Phe Leu Ala Ala Ser Ala Leu Gly Val Val Met Ile
                805                 810                 815

Thr Ala Ala Leu Ala Gly Ile Leu Lys Val Leu Arg Thr Ser Val Pro
            820                 825                 830

Phe Phe Trp Arg Arg Glu
        835

<210> SEQ ID NO 14
<211> LENGTH: 2517
<212> TYPE: DNA
<213> ORGANISM: Herpes simplex virus 1

<400> SEQUENCE: 14
ttattcgcgt ctccaaaaaa acgggacact tgtccggaga acctttagga tgccagccag      60
ggcggcggta atcataacca cgcccagcgc agaggcggcc agaaacccgg gcgcaattgc     120
ggccacgggc tgcgtgtcaa aggctagcaa atgaatgacg gttccgtttg gaaatagcaa     180
caaggccgtg gacggcacgt cgctcgaaaa cacgctcggg gcgccctccg tcggcccggc     240
ggcgatttgc tgctgtgtgt tgtccgtatc caccagcaac acagacatga cctccccggc     300
tggggtgtag cgcataaaca cggccccac gagcccagg tcgcgctggt tttgggtgcg     360
caccagccgc ttggactcga tatcccgggt ggagccttcg catgtcgcgg tgaggtaggt     420
taggaacagt gggcgtcgga cgtcgacgcc ggtgagcttg tagccgatcc cccgggcag      480
aggggagtgg gtgacgacgt agctggcgtt gtgggtgatg ggtaccagga tccgtggctc     540
gacgttggca gactgccccc cgcaccgatg tgaggcctca gggacgaagg cgcggatcag     600
ggcgttgtag tgtgcccagc gcgtcagggt cgaggcgagg ccgtgggtct gctgggccag     660
gacttcgacc ggggtctcgg atcgggtggc ttgagccagc gcgtccagga taaacacgct     720
ctcgtctaga tcaaagcgca gggaggccgc gcatggcgaa aagtggtccg gaagccaaaa     780
gagggttttc tggtggtcgg cccgggccag cgcggtccgg aggtcggcgt tggtcgctgc     840

-continued

```
ggcgacgtcg gacgtacaca gggccgatgc tatcagaagg ctccggcggg cgcgttcccg    900
ctgcaccgcc gaggggacgc ccgccaagaa cggctgccgg aggacagccg aggcgtaaaa    960
tagcgcccgg tggacgaccg gggtggtcag cacgcggccc cctagaaact cggcatacag   1020
ggcgtcgatg agatgggctg cgctgggcgc cactgcgtcg tacgccgagg gctatccag   1080
cacgaaggcc agctgatagc ccagcgcgtg taatgccaag ctctgttcgc gctccagaat   1140
ctcggccacc aggtgctgga gccgagcctc tagctgcagg cgggccgtgg gatccaagac   1200
tgacacatta aaaacacag aatccgcggc acagcccgcg gccccgcggg cggccaaccc   1260
ggcaagcgcg cgcgagtggg ccaaaaagcc tagcaggtcg gagaggcaga ccgcgccgtt   1320
tgcgtgggcg gcgttcacga aagcaaaacc cgacgtcgcg agcagccccg ttaggcgcca   1380
gaagagaggg gggcgcgggc cctgctcggc gcccgcgtcc cccgagaaaa actccgcgta   1440
tgcccgcgac aggaactggg cgtagttcgt gccctcctcc gggtagccgc ccacgcggcg   1500
gagggcgtcc agcgcggagc cgttgtcggc ccgcgtcagg gaccctagga caaagacccg   1560
ataccggggg ccgcccgggg gcccgggaag agccccgggg gggttttcgt ccgcgggtc   1620
cccgacccga tctagcgtct ggcccgcggg gaccaccatc acttccaccg gagggctgtc   1680
gtgcatggat atcacgagcc ccatgaattc ccgcccgtag cgcgcgcgca ccagcgcggc   1740
atcgcacccg agcaccagct ccccgtcgt ccagatgccc acgggccacg tcgaggccga   1800
cggggagaaa tacacgtacc tacctgggga tctcaacagg ccccgggtgg ccaaccaggt   1860
cgtggacgcg ttgtgcaggt gcgtgatgtc cagctccgtc gtcgggtgcc gccgggcccc   1920
aaccggcggt cgggggggcg gtgtatcacg cggcccgctt gggtggctcg ccgtcgccac   1980
gttgtctccc cgcgggaacg tcagggcctc ggggtcaggg acggccgaaa acgttaccca   2040
ggcccgggaa cgcagcaaca cggaggcgac tggattgtac aagagaccct taaggggggc   2100
gaccgagggg ggaggctggg cggtcggctc gaccgtggtg ggggcgggca ggctcgcgtt   2160
cgggggccgg ccgagcaggt aggtcttcgg gatgtaaagc agctggccgg ggtcccgcgg   2220
aaactcggcc gtggtgacca atacaaaaca aaagcgctcc tcgtaccagc gaagaagggg   2280
cagagatgcc gtagtcaggt ttagttcgtc cggcggcgcc agaaatccgc gcggtggttt   2340
ttgggggtcg ggggtgtttg cagccacag acgcccggtg ttcgtgtcgc gccagtacat   2400
gcggtccatg cccaggccat ccaaaaaacca tgggtctgtc tgctcagtcc agtcgtggac   2460
ctgaccccac gcaacgccca aaataataac ccccacgaac cataaaccat tccccat     2517
```

<210> SEQ ID NO 15
<211> LENGTH: 224
<212> TYPE: PRT
<213> ORGANISM: Herpes simplex virus 1

<400> SEQUENCE: 15

```
Met Gly Ile Leu Gly Trp Val Gly Leu Ile Ala Val Gly Ile Leu Cys
 1               5                   10                  15

Val Arg Gly Gly Leu Pro Ser Thr Glu Tyr Val Ile Arg Ser Arg Val
                20                  25                  30

Ala Arg Glu Val Gly Asp Ile Leu Lys Val Pro Cys Val Pro Leu Pro
            35                  40                  45

Ser Asp Asp Leu Asp Trp Arg Tyr Glu Thr Pro Ser Ala Ile Asn Tyr
        50                  55                  60

Ala Leu Ile Asp Gly Ile Phe Leu Arg Tyr His Cys Pro Gly Leu Asp
65                  70                  75                  80
```

```
Thr Val Leu Trp Asp Arg His Ala Gln Arg Ala Tyr Trp Val Asn Pro
                85                  90                  95

Phe Leu Phe Gly Ala Gly Phe Leu Glu Asp Leu Ser His Pro Ala Phe
            100                 105                 110

Pro Ala Asp Thr Gln Glu Thr Glu Thr Arg Leu Ala Leu Tyr Lys Glu
            115                 120                 125

Ile Arg Gln Ala Leu Asp Ser Arg Lys Gln Ala Ala Ser His Thr Pro
        130                 135                 140

Val Lys Ala Gly Cys Val Asn Phe Asp Tyr Ser Arg Thr Arg Arg Cys
145                 150                 155                 160

Val Gly Arg Gln Asp Leu Gly Leu Thr Asn Arg Thr Ser Gly Arg Thr
                165                 170                 175

Pro Val Leu Pro Ser Asp Asp Glu Ala Gly Leu Gln Pro Lys Pro Leu
            180                 185                 190

Thr Thr Pro Ser Pro Ile Ile Ala Thr Ser Asp Pro Thr Pro Arg Arg
            195                 200                 205

Asp Ala Ala Thr Lys Ser Arg Arg Arg Pro His Phe Arg Gly Leu
        210                 215                 220
```

```
<210> SEQ ID NO 16
<211> LENGTH: 675
<212> TYPE: DNA
<213> ORGANISM: Herpes simplex virus 1

<400> SEQUENCE: 16
atggggattt tgggttgggt cgggcttatt gccgttggga ttttgtgtgt gcggggggc       60 ttgccttcaa ccgaatatgt tattcggagt cgggtggctc gagaggtggg ggatatatta    120
aaggtgcctt gtgtgccgct cccgtctgac gatcttgatt ggcgctacga gaccccctcg    180
gctataaact atgctttgat agacggtata ttttttgcgt atcactgtcc cggattggac    240
acggtcttgt gggataggca cgcccagagg gcgtattggg ttaaccccctt tttgtttggg    300 gcgggttttt tggaggactt gagtcatccc gcgtttcctg ccgacaccca ggaaacagaa    360
acgcgcttgg ccctttataa agagatacgc caggcgctgg acagtcgcaa gcaggccgcc    420
agccacacac ctgtgaaggc tgggtgtgtg aactttgact attcgcgcac cgccgctgt    480 gtagggcgcc aggatttggg acttaccaac agaacgtctg gacggacccc ggttctgccg    540
tcggacgatg aagcgggcct gcagccgaag ccccctcacca cgccgtcgcc catcatcgcc    600
acgtcggacc ccaccccgcg acgggacgcc gccacaaaaa gcagacgccg acgaccccac    660
ttccggggcc tttaa                                                       675

<210> SEQ ID NO 17
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 17

His His His His His His
1               5
```